US009675576B2

(12) United States Patent
Golub et al.

(10) Patent No.: US 9,675,576 B2
(45) Date of Patent: *Jun. 13, 2017

(54) POLYENOLIC ZINC-BINDING AGENTS (PEZBINS) ACTIVELY PROMOTE INACTIVATION OF CANCER STEM CELLS AND POTENTIATE CYTOTOXIC ANTI-TUMOR DRUG SUBSTANCES

(71) Applicants: The Research Foundation for The State University of New York, Albany, NY (US); Chem-Master International, Inc., East Setauket, NY (US)

(72) Inventors: Lorne M. Golub, Smithtown, NY (US); Francis Johnson, Setauket, NY (US); Galina I. Botchkina, Stony Brook, NY (US); Iwao Ojima, Port Jefferson, NY (US)

(73) Assignees: THE RESEARCH FOUNDATION FOR THE STATE UNIVERSITY OF NEW YORK, Albany, NY (US); CHEM-MASTER INTERNATIONAL, INC., East Setauket, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/950,033

(22) Filed: Nov. 24, 2015

(65) Prior Publication Data

US 2016/0213638 A1 Jul. 28, 2016

Related U.S. Application Data

(63) Continuation of application No. 14/408,748, filed as application No. PCT/US2013/048710 on Jun. 28, 2013, now Pat. No. 9,220,695.

(60) Provisional application No. 61/666,504, filed on Jun. 29, 2012.

(51) Int. Cl.
| | |
|---|---|
| A61K 31/216 | (2006.01) |
| A61K 31/444 | (2006.01) |
| A61K 31/136 | (2006.01) |
| A61K 31/167 | (2006.01) |
| A61K 31/337 | (2006.01) |
| A61K 45/06 | (2006.01) |

(52) U.S. Cl.
CPC .......... *A61K 31/216* (2013.01); *A61K 31/136* (2013.01); *A61K 31/167* (2013.01); *A61K 31/337* (2013.01); *A61K 31/444* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,401,504 A | 3/1995 | Das et al. | |
| 7,579,486 B2 | 8/2009 | Puerta et al. | |
| 7,763,289 B2 | 7/2010 | Bommarito | |
| 8,236,852 B2 | 8/2012 | Shih et al. | |
| 9,187,406 B2 | 11/2015 | Johnson et al. | |
| 9,220,695 B2 * | 12/2015 | Golub ................. | A61K 31/337 |
| 2004/0253329 A1 | 12/2004 | Mae et al. | |
| 2005/0267221 A1 | 12/2005 | Wellem et al. | |
| 2006/0258752 A1 | 11/2006 | Vander Jagt et al. | |
| 2006/0276536 A1 | 12/2006 | Vander Jagt et al. | |
| 2007/0060644 A1 | 3/2007 | Vander Jagt et al. | |
| 2007/0231334 A1 | 10/2007 | Alibek et al. | |
| 2008/0161391 A1 | 7/2008 | Lee et al. | |
| 2008/0200478 A1 | 8/2008 | Robinson et al. | |
| 2009/0018209 A1 | 1/2009 | Arbiser | |
| 2010/0010232 A1 | 1/2010 | Neupert et al. | |
| 2010/0152493 A1 | 6/2010 | Shibata et al. | |
| 2011/0044895 A1 | 2/2011 | Berryal et al. | |
| 2011/0152382 A1 | 6/2011 | Hengal et al. | |
| 2012/0095051 A1 | 4/2012 | Johnson et al. | |
| 2015/0073021 A1 | 3/2015 | Antonelli et al. | |
| 2015/0150834 A1 | 6/2015 | Golub et al. | |

FOREIGN PATENT DOCUMENTS

| | | |
|---|---|---|
| DE | 25 01 220 A1 | 7/1976 |
| JP | 2008 137914 A | 6/2008 |
| KR | 2010-049929 | 5/2010 |
| WO | WO 00/70949 A1 | 11/2000 |

(Continued)

OTHER PUBLICATIONS

Extended European Search Report issued Feb. 3, 2015 in connection with European application No. 12841310.1.

(Continued)

*Primary Examiner* — Samantha Shterengarts

(74) *Attorney, Agent, or Firm* — Gary J. Gershik; Cooper & Dunham LLP

(57) ABSTRACT

The present invention provides a method of inhibiting the growth of or promoting differentiation and destruction of cancer stem cells (CSCs) comprising contacting the cancer stem cells with a compound having the structure:

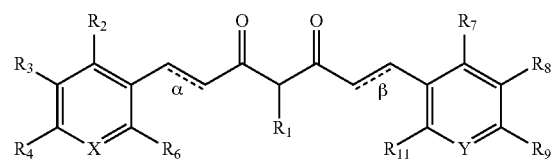

or a pharmaceutically acceptable salt thereof.

20 Claims, 30 Drawing Sheets

(56) References Cited

FOREIGN PATENT DOCUMENTS

| WO | WO 2013/059203 A1 | 4/2003 |
|---|---|---|
| WO | WO 03/063793 A2 | 8/2003 |
| WO | WO 03/088927 A2 | 10/2003 |
| WO | WO 2008/045534 A2 | 4/2008 |
| WO | WO 2008/048410 A2 | 4/2008 |
| WO | WO 2008/085984 A1 | 7/2008 |
| WO | WO 2010/121007 A1 | 10/2010 |
| WO | WO 2010/132815 A1 | 11/2010 |
| WO | WO 2011/142795 A1 | 11/2011 |
| WO | WO 2014/005089 A2 | 1/2014 |
| WO | WO 2016/145159 A1 | 9/2016 |

OTHER PUBLICATIONS

International Search Report issued Jan. 17, 2013 in connection with International Application No. PCT/US2012/060437.
Written Opinion of the International Search Authority issued Jan. 17, 2013 in connection with International Application No. PCT/US2012/060437.
International Preliminary Report on Patentability Chapter I issued Apr. 22, 2014 in connection with International Application No. PCT/US2012/060437.
International Search Report issued Feb. 14, 2014 in connection with International Application No. PCT/US2013/048710.
Written Opinion of the International Search Authority issued Feb. 14, 2014 in connection with International Application No. PCT/US2013/048710.
International Preliminary Report on Patentability Chapter I issued Feb. 14, 2014 in connection with International Application No. PCT/US2013/048710.
International Search Report issued Jul. 12, 2010 in connection with International Application No. PCT/2010/034971.
Written Opinion of the International Search Authority issued Jul. 12, 2010 in connection with International Application No. PCT/2010/034971.
International Preliminary Report on Patentability Chapter I issued Nov. 15, 2011 in connection with Internatonal Application No. PCT/2010/034971.
Office Action issued Dec. 16, 2014 in connection with U.S. Appl. No. 13/319,478.
European Search Report issued Oct. 18, 2012 in connection with European Application No. EP 10775624.9.
Communication Pursuant to Rules 70(2) and 70a(2) EPC issued Nov. 6, 2012 by the European Patent Office in connection with European Application No. EP 10775624.9.
Pill-Hoon Bong (1999) "Spectral and photophysical behaviours of curcumin and curcuminoids." Bull. Korean Chem. Soc., vol. 21, No. 1, pp. 81-86.
Jankun et al. (2006) "Synthetic curcuminoids modulate the arachidonic acid metabolism of human platelet 12-lipoxygenase and reduce sprout formation of human endothelial cells", Molecular Cancer Therapeutics, vol. 5, No. 5, pp. 1371-1382.
Matthes et al. (1980) "Cytotoxic components of Zingiber Zerumbet, Curcuma Zedoaria and C. Domestica", Phytochemistry, vol. 19, pp. 2643-2650.
Shao Wy et al. (2006) "Facile preparation of new unsymmetrical curcuma derivatives by solid-phase synthesis strategy" Tetrahedron Letters, vol. 47, No. 24, pp. 4085-4089.
Weber W.M. et al. (2006) "Activation of NFkappaB is inhibited by curcumin and related enones" Bioorganic & Medicinal Chemistry, vol. 14, No. 7, pp. 2450-2461.
Zhang et al. (2008) "Synthesis and cytotoxic activity of novel curcumin analogues" Chinese Chemical Letters, vol. 19, No. 3, pp. 281-285.
Office Action issued Mar. 12, 2015 in connection with U.S. Appl. No. 14/352,277.
Third-Party Submission Under 37 CFR 1.290 dated Mar. 10, 2015 in connection with U.S. Appl. No. 14/352,277.
Notice of Allowance issued Jul. 17, 2015 in connection with U.S. Appl. No. 13/319,478.
Antonelli et al. "Inhibition of anthrax lethal factor by curcumin and chemically modified curcumin derivatives" J Enzyme Inhib Med Chem, 2014; 29(5): 663-669.
Notification of Transmittal of the International Search Report and the Written Opinion of the International Searching Authority, or the Declaration, including an International Search Report and Written Opinion of the International Searching Authority, mailed Feb. 14, 2014 in connections with PCT International Application No. PCT/US2013/048710, filed Jun. 28, 2013.
Office Action issued Oct. 22, 2015 in connection with U.S. Appl. No. 14/478,886.
Notice of Allowance issued Aug. 13, 2015 in connection with U.S. Appl. No. 14/408,748.
Office Action issued Sep. 9, 2015 in connection with U.S. Appl. No. 14/352,277.
Final Office Action issued May 18, 2016 in connection with U.S. Appl. No. 14/352,277.
Office Action issued Feb. 11, 2016 in connection with European application No. 12841310.1.
Extended European Search Report issued Jan. 8, 2016 in connection with European application No. 13808853.9.
Final Office Action issued May 4, 2016 in connection with U.S. Appl. No. 14/478,886.
Bin Bao et al. (2011) "Anti-Tumor Activity of a Novel Compound-CDF Is Mediated by Regulating miR-21, miR-200, and PTEN in Pancreatic Cancer" PLOS ONE, 6, e17850.
Botchkina, et al. (2010) "New-generation taxoid SB-T-1214 inhibits stem cell-related gene expression in 3D cancer spheroids induced by purified colon tumor-initiating cells" Molecular Cancer, 9, 192.
Botchkina, et al. (2013) "Prostate Cancer Stem Cell-Targeted Efficacy of a New-Generation Taxoid, SBT-1214 and Novel Polyenolic Zinc-Binding Curcuminoid, CMC2.24" PLOS ONE, 9, e69884.
Lorencini, M et al. (2009) "Changes in MMPs and inflammatory cells in experimental gingivitis" Histol Histopathol 24, 157-166 (Summary).
Zhou et al. (2008) "NF-kappaB pathway inhibitors preferentially inhibit breast cancer stem-like cells" Breast Cancer Res Treat, 111, 419.
Aug. 5, 2016 Response to Communication Pursuant to R. 70(2)and 70a(2) EPC filed with European Patent Office in connection with European Patent Application No. 13808853.9.
Jiangbing Zhou et al. (2008) "Pathway Inhibitors Preferentially Inhibit Breast Cancer Stem-like Cells" Breast Cancer Research and Treatment, Kluwer Academic Publishers, BO, vol. 111, No. 3, pp. 419-427.
Bin Bao et al. (2011) "Anti-Tumor Activity of a Novel Compound-CDF is Mediated by Regulating miR-21, miR-200, and PTEN in Pancreatic Cancer", PLoS ONE, vol. 6, No. 3, p. e17850.
Botchkina Galina I et al. (2010) "New-generation Taxoid SB-T-1214 Inhibits Stem Cell-Related Gene Expression in 3D Cancer Spheroids Induced by Purified Colon Tumor-initiating Cells", Molecular Cancer, Biomed Central, London, GB, vol. 9, No. 1, p. 192.
Galina I. Botchkina et al. (2013) "Prostate Cancer Stem Cell-Targeted Efficacy of a New-Generation Taxoid, SBT-1214 and Novel Polyenolic Zinc-Binding Curcuminoid, CMC2.24", PLoS, vol. 8, No. 9, p. e69884.
Jan. 8, 2016 European Search Report issued in connection with the European Patent Application No. 13808853.9.
Feb. 11, 2016 Communication Pursuant to Article 94(3)EPC issued in connection with the European Patent Application No. 12841310.1.
Notice of Allowance issued Oct. 11, 2016 in connection with U.S. Appl. No. 14/883,074.
Aug. 5, 2016 Amendment filed in connection with European application No. 13808853.9.
Office Action issued Nov. 7, 2016 in connection with U.S. Appl. No. 14/478,886.
International Search Report issued Aug. 18, 2016 in connection with International Application No. PCT/US2016/021723.

(56) References Cited

OTHER PUBLICATIONS

Written Opinion of the International Search Authority issued Aug. 18, 2016 in connection with International Application No. PCT/US2016/021723.

Venkatesan, N. et al. (2007) Protection from acute and chronic lung diseases by curcumin. Adv Exp Med Biol, 595, pp. 379-405.

Bansal, S. et al. (2010) Curcumin alone and in combination with augmentin protects against pulmonary inflammation and acute lung injury generated during Klebsiella pneumoniae B5055-induced lung infection in BALB/c mice. J Med Microbiol, 59 (Pt 4), pp. 429-437.

Bonnans C. et al. (2007) Lipid mediators as agonists for the resolution of acute lung inflammation and injury. Am J Respir Cell Mol Biol, 36(2), pp. 201-205.

Seki, H. et al. (2010) The anti-inflammatory and proresolving mediator resolvin El protects mice from bacterial pneumonia and acutre lung injury. J Immunol, 184(2), pp. 836-843.

* cited by examiner

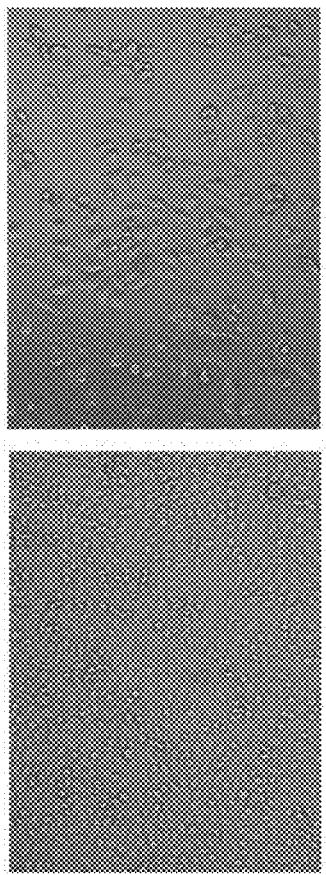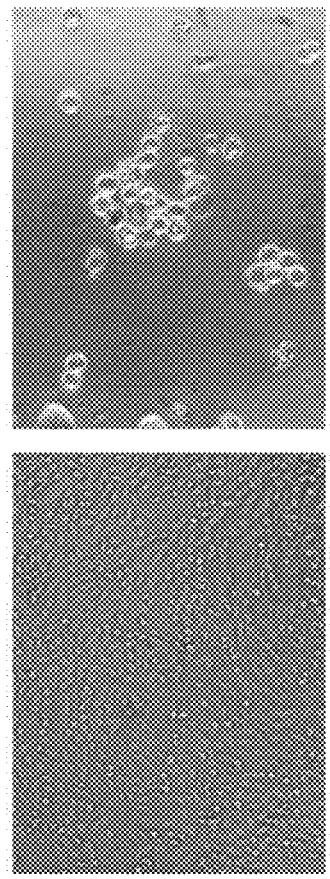
Fig. 5C

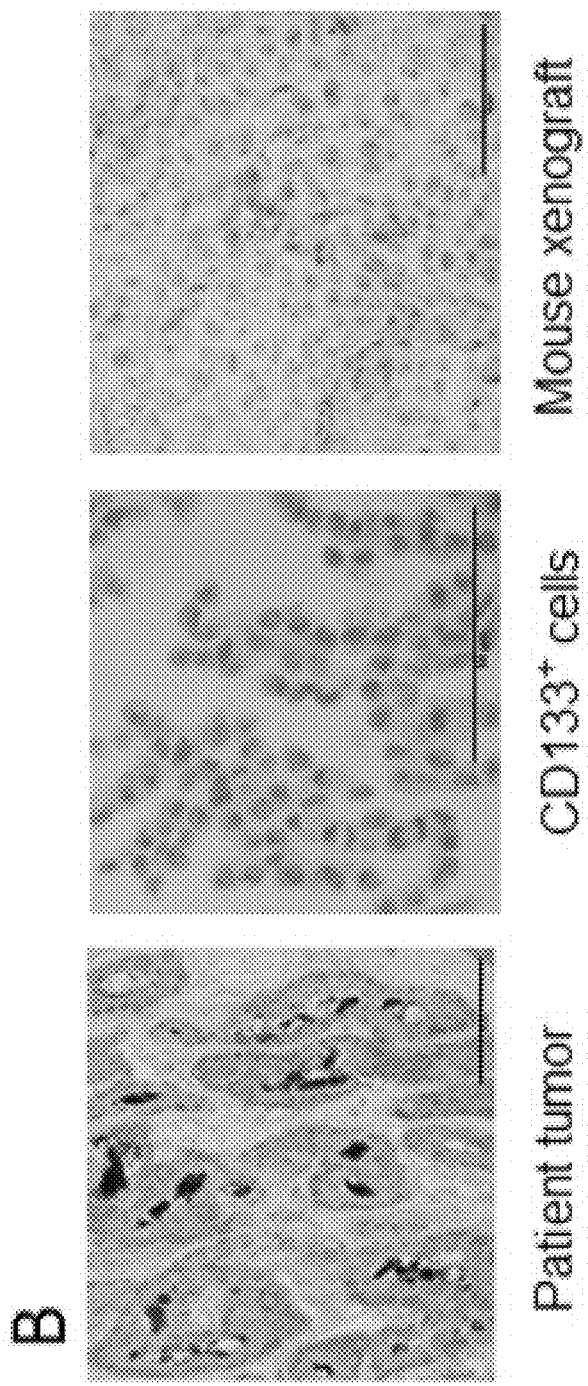

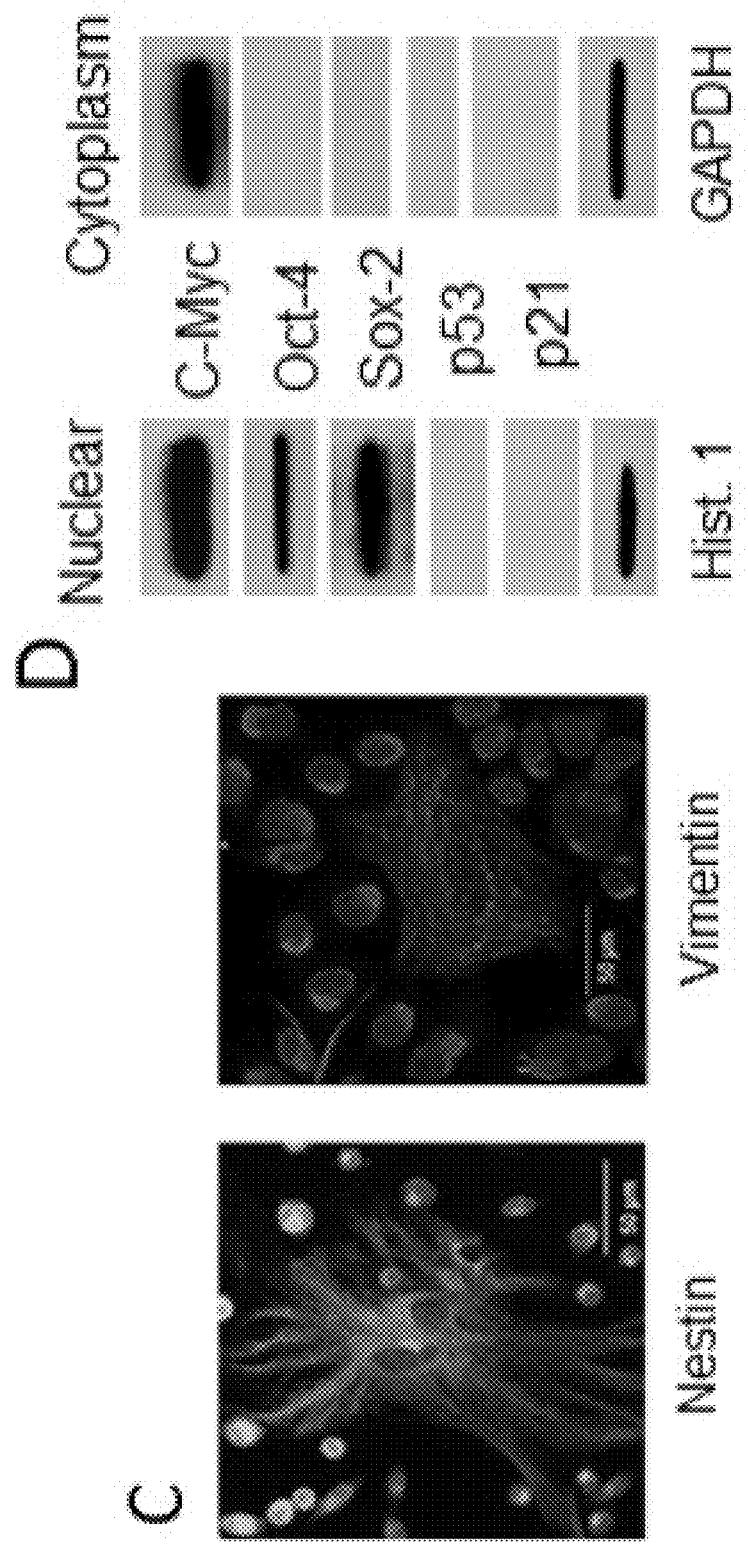
Fig. 7C-D

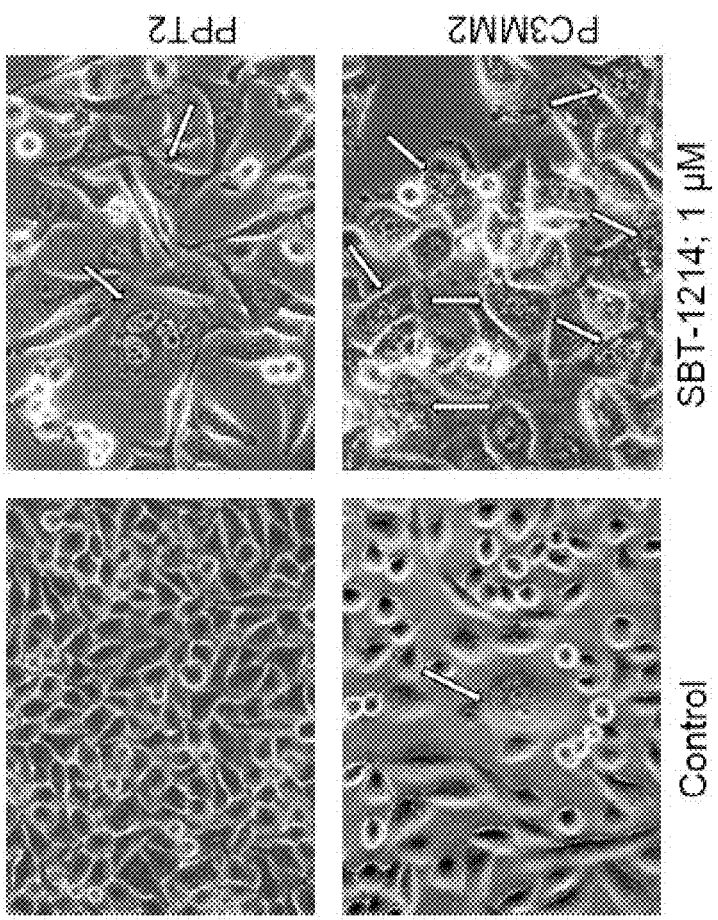
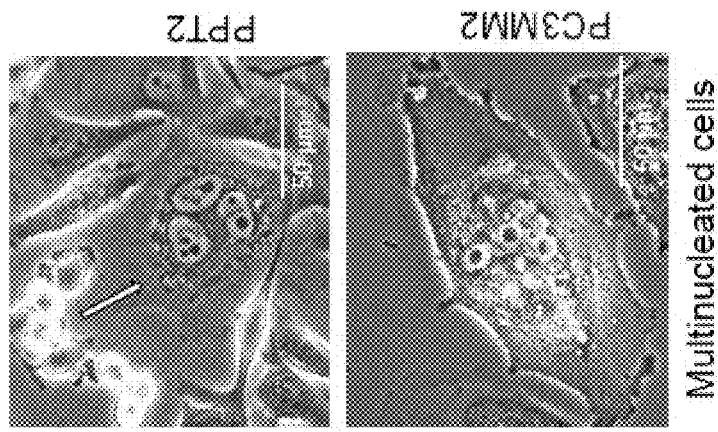
Fig. 9A-B

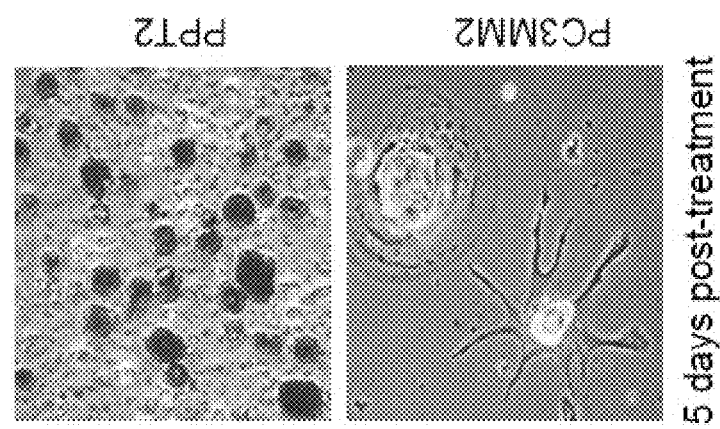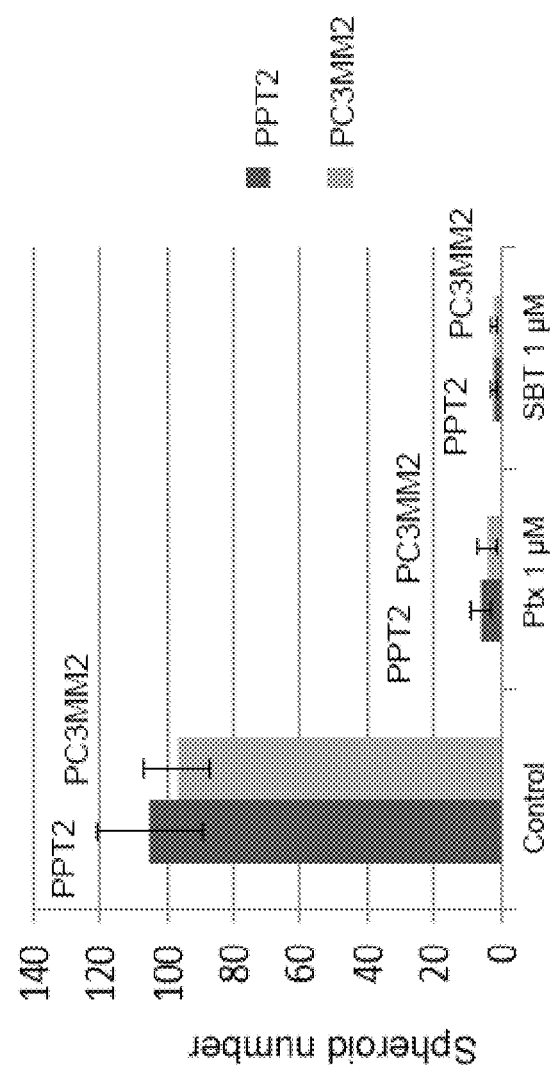
Fig. 9C-D

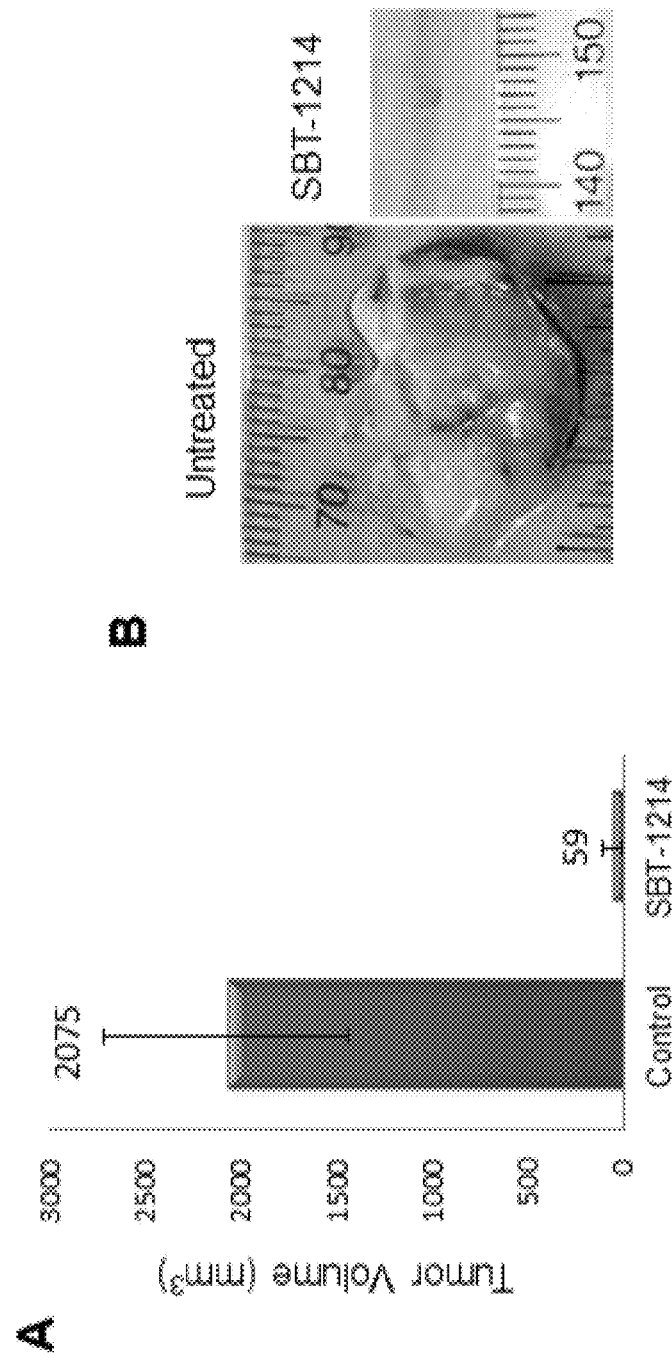
Fig. 10A-B

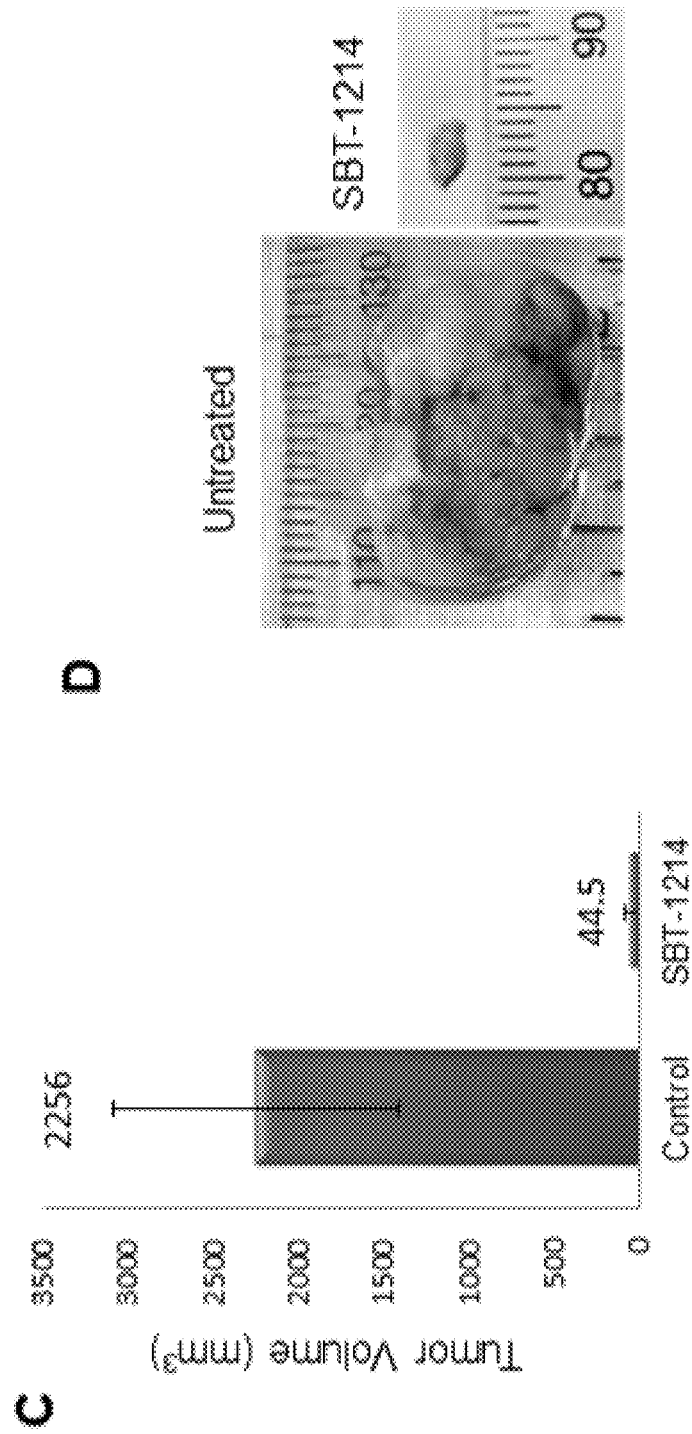
Fig. 10C-D

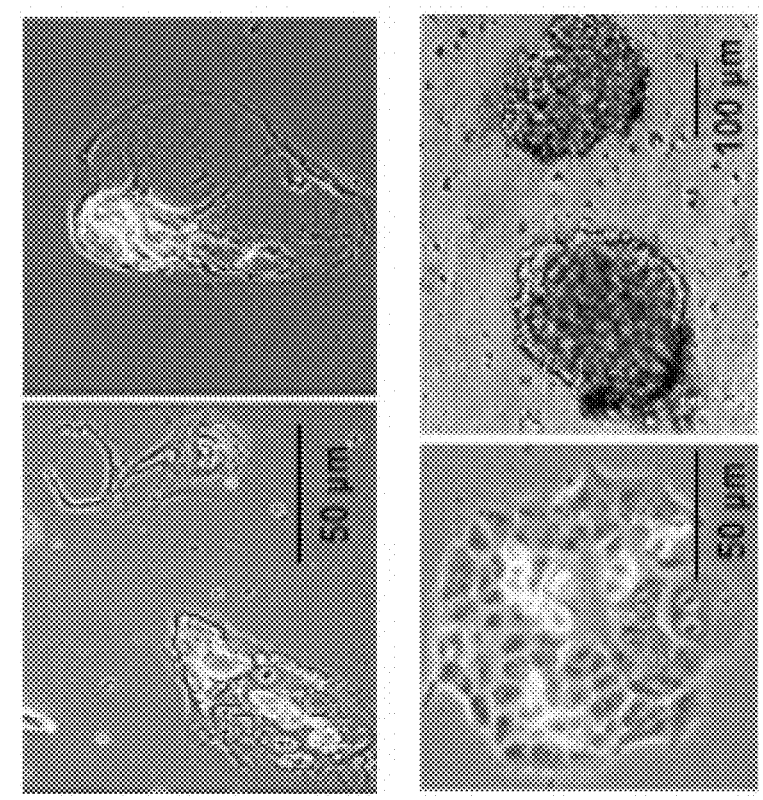
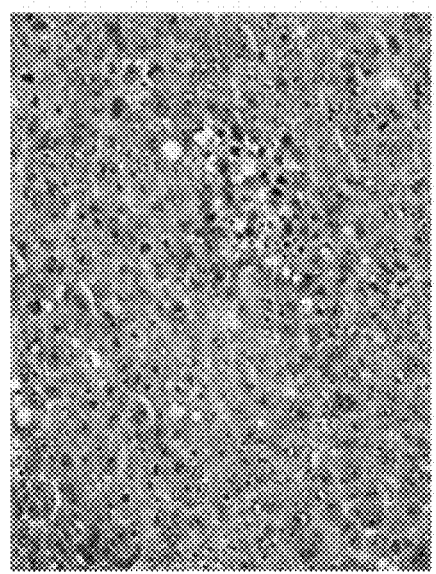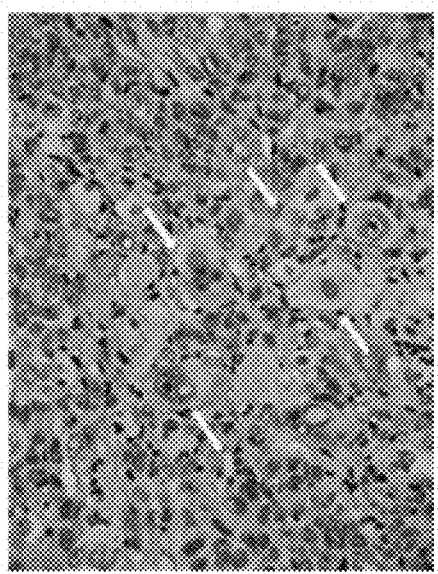
Fig. 10E-H

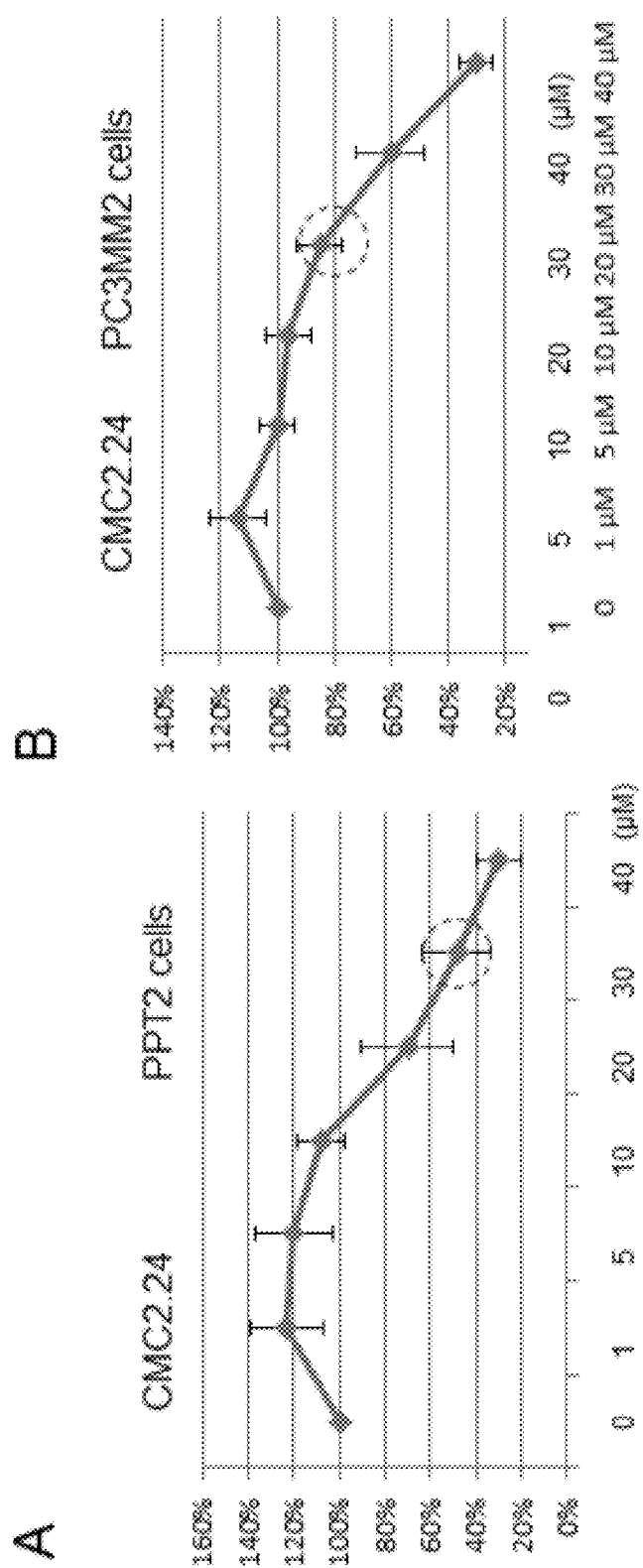
Fig. 11A-B

POLYENOLIC ZINC-BINDING AGENTS (PEZBINS) ACTIVELY PROMOTE INACTIVATION OF CANCER STEM CELLS AND POTENTIATE CYTOTOXIC ANTI-TUMOR DRUG SUBSTANCES

The invention was made with government support under Grant numbers CA150085 and CA103314 awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Despite advances in screening and surgical treatment, metastatic epithelial cancers, which represent about 90% of human cancers, have no known cure. Tumor regression induced by standard anti-cancer therapies does not correlate with patient survival (Brekelmans et al., 2007). Such ineffectiveness of conventional therapies has been attributed to the existence of rare malignant stem cells possessing tumor-initiating potential and maintaining tumor growth, spread, and resistance to treatment (Reya et al., 2001; Clarke et al, 2006). The existence of these cancer stem cells (CSCs) was firmly confirmed in the majority of human cancers, including those of the prostate (Collins et al., 2005; Patrawala et al., 2006; 2007; Miki et al, 2007; Rowehl et al., 2008; Klarmann et al., 2009) and colon (O'Brien et al. 2007; Ricchi-Vitiani, 2007; Todaro et al., 2007) cancers. CSCs are not only highly resistant to conventional therapies, but may actually promote cancer progression by stimulating quiescent CSCs to self-renew and repopulate the tumor with undifferentiated drug resistant cells, thereby promoting cancer progression (FIG. 1) (Bao et al., 2006; Dirks, 2006; Eramo et al., 2006; Todaro et al., 2007; Bleau et al., 2009; Tortoreto et al., 2009; Yu et al., 2012). It was recently demonstrated that treatment with 5-FU and oxaliplatin, a standard therapy for metastatic colon cancer, induced up to 30-fold enrichment of CD133$^+$ and up to 2-fold enrichment of CD44$^+$ cells in HT29 cell line (Dallas et al., 2009).

In many cancers, the ratio of the stem-like cells to other cancer cell types correlates with tumor aggressiveness, histologic grade and clinical outcome (Mimeault & Batra, 2010). Although metastatic progression depends on multiple factors, several CSC features make them very likely candidates to be the cause and driving force of metastasis (Visvader & Lindeman, 2009; Shen & Abate-Shen, 2011). If CSCs are the only cell population with tumorigenic potential, it is conceivable that metastases-initiating cells could have CSC capabilities, and only multipotent CSCs have inherent plasticity to survive in a foreign environment and to propagate into a heterogeneous metastatic tumor. Moreover, the most recent data shows that CSCs can differentiate to or directly participate functionally as endothelial cells, thereby directly generating the necessary vasculature for secondary tumors (Hutchinson, 2011). Stem-like cells with metastatic activity were detected recently in several types of primary and metastatic tumors and metastatic cell lines (Brabletz et al., 2005; Balic et al., 2006; Patrawala et al., 2006; 2007; Hermann et al., 2007; Aktas et al., 2009; rev. Kelly & Yin, 2008; Mimeault & Batra, 2010). Therefore, due to the extreme clinical and biological significance of the CSCs, novel strategies must be targeted to the elimination of CSCs and/or the promotion of their differentiation.

Prostate cancer (PrC) is the second leading cause of cancer death among men in Western society (Jemal, A. 2011). It is initially sensitive to androgen deprivation therapy, but more than 70% of patients face post-treatment recurrence and transition of the disease to an incurable state (van Brussel, J. P. 2003). For patients diagnosed with androgen-independent PrC, microtubule stabilizers such as Paclitaxel (Ptx; Taxol) are a first-line treatment strategy that is initially effective. However, approaches to treating chemoresistant PrC are currently lacking (Zivi, A. 2010). After the initial discovery of cancer stem cells, CSCs (Zivi, A. 2010), it became increasingly evident that tumors are organized hierarchically, containing a relatively minor (but varying) population of tumor-initiating cells and a heterogeneous majority of bulk tumor cells at different stages of maturation. In support of the CSC concept of carcinogenesis, a recent study demonstrated that the expression of several commonly used CSC markers, i.e. CD44, CD166 and ALDH-1, as well as the proportion of cells that express these markers, increases with aging (Nautiyal, J. 2012). It is an established phenomenon that aging correlates with a sharp increase in the incidence of prostate and many other cancers (Jemal, A. 2011). Accumulated knowledge clearly indicates that CSCs are responsible for tumor development, maintenance and resistance to standard treatment modalities. Thus, it has been shown for many cancer types that the tumorigenic cells expressing common CSC markers, in particular CD133 and CD44, are exceptionally resistant to conventional anti-cancer drugs (such as 5-FU, oxaliplatin, irinotecan, docetaxel and others). Moreover, the number of such cells can be significantly propagated after therapy (Bao, S. 2006; Dirks P. B. 2006; Todaro, M. 2007; Woodward, W. A. 2007; Dylla, S. J. 2008; Tortoreto, M. 2009; Bleau, A. M. 2009; Mimeault, M. 2010), which usually manifests as more drug-resistant and more aggressive recurrent and metastatic disease. It is conceivable that CSCs represent the most crucial target in the development of a new generation of anti-cancer drugs.

Therefore, due to the extreme clinical and biological significance of the CSCs, novel strategies must be targeted to the elimination of CSCs and/or the promotion of their differentiation.

SUMMARY OF THE INVENTION

The present invention provides a method of inhibiting the growth of or promoting differentiation of cancer stem cells (CSCs) comprising contacting the cancer stem cells with a compound having the structure:

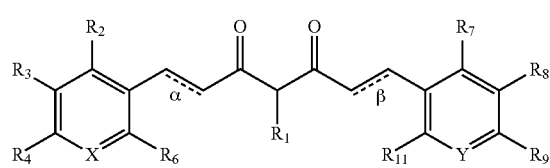

wherein
bond α and β are each, independently, present or absent;
X is $CR_5$ or N; Y is $CR_{10}$ or N;
$R_1$ is H, $CF_3$, halogen, $-NO_2$, $-OCF_3$, $-OR_{12}$, $-NHCOR_{12}$, $-CONR_{12}R_{13}$, $-CSNR_{12}R_{13}$, $-C(=NH)$ $NR_{12}R_{13}$, $-SR_{12}$, $-SO_2R_{13}$, $-COR_{14}$, $-CSR_{14}$, $-C(=NR_{12})R_{14}$, $-C(=NR_{12})NR_{13}R_{14}$, $-SOR_{12}$, $-SONR_{12}R_{13}$, $-SO_2NR_{12}R_{13}$, $-P(O)R_{12}$, $-PH(=O)OR_{12}$, $-P(=O)(OR_{12})(OR_{13})$, or $-P(OR_{12})(OR_{13})$, wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-12}$ alkyl, $C_{2-10}$ alkenyl, $C_{2-10}$ alkynyl, heteroaryl, heterocyclyl, methoxy, $-OR_{15}$, $-NR_{16}R_{17}$, or

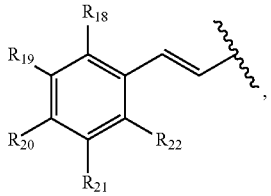

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $-SOR_{23}$, $-POR_{23}$, $-C(=S)R_{23}$, $-C(=NH)R_{23}$, $-C(=N)R_{23}$, $-P(=O)(OR_{23})(OR_{24})$, $-P(OR_{23})(OR_{24})$, $-C(=S)R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-20}$ alkenyl, $C_{2-10}$ alkynyl, aryl, heteroaryl, or heterocyclyl;

$R_{20}$ is halogen, $-NO_2$, $-CN$, $-NR_{26}R_{27}$, $CF_3$, $C_{1-10}$ alkyl, $C_{2-20}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}^+$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein when $R_1$ is H, then $R_3$, $R_4$, $R_5$, $R_8$, $R_9$, or $R_{10}$, is halogen, $-NO_2$, $-CN$, $-NR_{28}R_{29}$, $-NHR_{28}R_{29}^+$, $-SR_{28}$, $-SO_2R_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein each occurrence of alkyl, alkenyl, or alkynyl is branched or unbranched, unsubstituted or substituted;

or a pharmaceutically acceptable salt thereof.

The present invention provides a method of down-regulating cancer stem cell-relevant transcription factors comprising contacting the cancer stem cell with a compound having the structure:

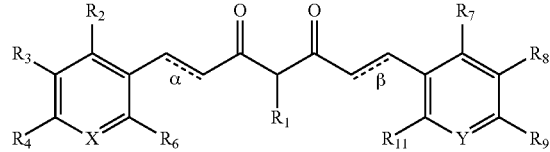

wherein
bond α and β are each, independently, present or absent;
X is $CR_5$ or N; Y is $CR_{10}$ or N;
$R_1$ is H, $CF_3$, halogen, $-NO_2$, $-OCF_3$, $-OR_{12}$, $-NHCOR_{12}$, $-CONR_{12}R_{13}$, $-CSNR_{12}R_{13}$, $-C(=NH)NR_{12}R_{13}$, $-SR_{12}$, $-SO_2R_{13}$, $-COR_{14}$, $-CSR_{14}$, $-C(=NR_{12})R_{14}$, $-C(=NR_{12})NR_{13}R_{14}$, $-SOR_{12}$, $-SONR_{12}R_{13}$, $-SO_2NR_{12}R_{13}$, $-P(O)R_{12}$, $-PH(=O)OR_{12}$, $-P(=O)(OR_{12})(OR_{13})$, or $-P(OR_{12})(OR_{13})$, wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

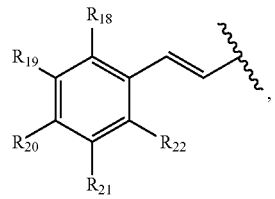

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $-SOR_{23}$, $-POR_{23}$, $-C(=S)R_{23}$, $-C(=NH)R_{23}$, $-C(=N)R_{23}$, $-P(=O)(OR_{23})(OR_{24})$, $-P(OR_{23})(OR_{24})$, $-C(=S)R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, $-NO_2$, $-CN$, $-NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{2-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}^+$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein when $R_1$ is H, then $R_3$, $R_4$, $R_5$, $R_8$, $R_9$, or $R_{10}$, is halogen, $-NO_2$, $-CN$, $-NR_{28}R_{29}$, $-NHR_{28}R_{29}^+$, $-SR_{28}$, $-SO_2R_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein each occurrence of alkyl, alkenyl, or alkynyl is branched or unbranched, unsubstituted or substituted;

or a pharmaceutically acceptable salt thereof.

The present invention provides a method of inhibiting the growth of a tumor comprising cancer stem cells (CSCs) by contacting the tumor with a compound having the structure:

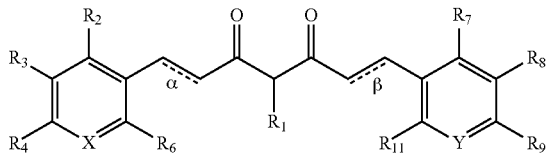

wherein bond α and β are each, independently, present or absent;

X is $CR_5$ or N; Y is $CR_{10}$ or N;

$R_1$ is H, $CF_3$, halogen, $-NO_2$, $-OCF_3$, $-OR_{12}$, $-NHCOR_{12}$, $-CONR_{12}R_{13}$, $-CSNR_{12}R_{13}$, $-C(=NH)NR_{12}R_{13}$ $-SR_{12}$, $-SO_2R_{13}$, $-COR_{14}$, $-CSR_{14}$, $-C(=NR_{12})R_{14}$, $-C(=NR_{12})NR_{13}R_{14}$, $-SOR_{12}$, $-SONR_{12}R_{13}$, $-SO_2NR_{12}R_{13}$, $-P(O)R_{12}$, $-PH(=O)OR_{12}$ $-P(=O)(OR_{12})(OR_{13})$, or $-P(OR_{12})(OR_{13})$, wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

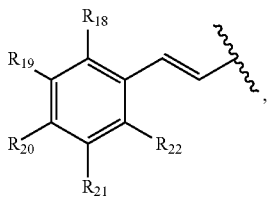

wherein $R_{15}$ is H, $C_{3-10}$ alkyl, $C_{2-10}$ alkenyl, $C_{2-20}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $-SOR_{23}$, $-POR_{23}$, $-C(=S)R_{23}$, $-C(=NH)R_{23}$, $-C(=N)R_{23}$, $-P(=O)(OR_{23})(OR_{24})$, $-P(OR_{23})(OR_{24})$, $-C(=S)R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, $-NO_2$, $-CN$, $-NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}^+$, $-SR_{28}$, $-SO_2R_{28}$, $-OR_{21}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein when $R_1$ is H, then $R_3$, $R_4$, $R_5$, $R_8$, $R_9$, or $R_{10}$, is halogen, $-NO_2$, $-CN$, $-NR_{28}R_{29}$, $-NHR_{28}R_{29}^+$, $-SR_{28}$, $-SO_2R_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein each occurrence of alkyl, alkenyl, or alkynyl is branched or unbranched, unsubstituted or substituted;

or a pharmaceutically acceptable salt thereof.

The present invention provides a method of treating a patient suffering from cancer comprising administering to the patient a compound having the structure:

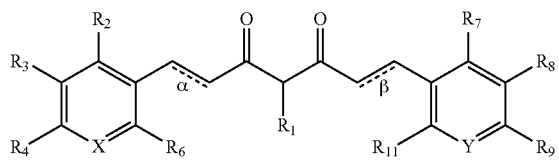

wherein bond α and β are each, independently, present or absent;

X is $CR_5$ or N; Y is $CR_{10}$ or N;

$R_1$ is H, $CF_3$, halogen, $-NO_2$, $-OCF_3$, $-OR_{12}$, $-NHCOR_{12}$, $-CONR_{12}R_{13}$, $-CSNR_{12}R_{13}$, $-C(=NH)NR_{12}R_{13}$ $-SR_{12}$, $-SO_2R_{13}$, $-COR_{14}$, $-CSR_{14}$, $-C(=NR_{12})R_{14}$, $-C(=NR_{12})NR_{13}R_{14}$, $-SOR_{12}$, $-SONR_{12}R_{13}$, $-SO_2NR_{12}R_{13}$, $-P(O)R_{12}$, $-PH(=O)OR_{12}$ $-P(=O)(OR_{12})(OR_{13})$, or $-P(OR_{12})(OR_{13})$, wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

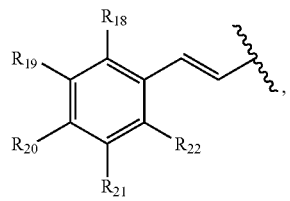

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $-SOR_{23}$, $-POR_{23}$, $-C(=S)R_{23}$, $-C(=NH)R_{23}$, $-C(=N)R_{23}$, $-P(=O)(OR_{23})(OR_{24})$, $-P(OR_{23})(OR_{24})$, $-C(=S)R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, $-NO_2$, $-CN$, $-NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein when $R_1$ is H, then $R_3$, $R_4$, $R_5$, $R_8$, $R_9$, or $R_{10}$, is halogen, —$NO_2$, —CN, —$NR_{28}R_{29}$, —$NHR_{28}R_{29}^+$, —$SR_{28}$, —$SO_2R_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein each occurrence of alkyl, alkenyl, or alkynyl is branched or unbranched, unsubstituted or substituted;

or a pharmaceutically acceptable salt thereof.

The present invention provides a compound for use in inhibiting the growth of or promoting differentiation of cancer stem cells (CSCs), down-regulating cancer stem cell relevant transcription factors in a cancer stem cell, or the treatment of cancer in a subject afflicted with cancer, the compound having the structure:

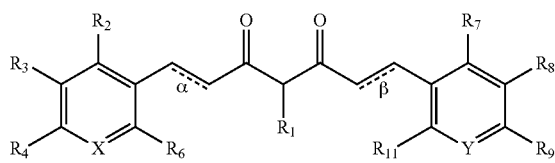

wherein bond α and β are each, independently, present or absent;

X is $CR_5$ or N; Y is $CR_{10}$ or N;

$R_1$ is H, $CF_3$, halogen, —$NO_2$, —$OCF_3$, —$OR_{12}$, —NHCOR$_{12}$, —$CONR_{12}R_{13}$, —$CSNR_{12}R_{13}$, —C(=NH)NR$_{12}R_{13}$ —$SR_{12}$, —$SO_2R_{13}$, —$COR_{14}$, —C(=NR$_{12}$)R$_{14}$, —C(=NR$_{12}$)NR$_{13}R_{14}$, —$SOR_{12}$, —$SONR_{12}R_{13}$, —$SO_2NR_{12}R_{13}$, —P(O)R$_{12}$, —PH(=O)OR$_{12}$ —P(=O)(OR$_{12}$)(OR$_{13}$), or —P(OR$_{12}$)(OR$_{13}$), wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, —$OR_{15}$, —$NR_{16}R_{17}$, or

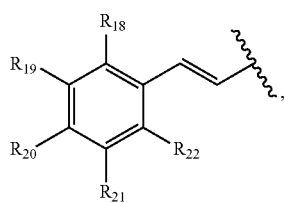

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, —$SOR_{23}$, —$POR_{23}$, —C(=S)R$_{23}$, —C(=NH)R$_{23}$, —C(=N)R$_{23}$, —P(=O)(OR$_{23}$)(OR$_{24}$), —P(OR$_{23}$)(OR$_{24}$), —C(=S)R$_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein when $R_1$ is H, then $R_3$, $R_4$, $R_5$, $R_8$, $R_9$, or $R_{10}$, is halogen, —$NO_2$, —CN, —$NR_{28}R_{29}$, —$NHR_{28}R_{29}^+$, —$SR_{28}$, —$SO_2R_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein each occurrence of alkyl, alkenyl, or alkynyl is branched or unbranched, unsubstituted or substituted;

or a pharmaceutically acceptable salt thereof.

The present invention provides CMC2.24 for use in combination with a chemotherapeutic agent in inhibiting the growth of or promoting differentiation of cancer stem cells (CSCs), down-regulating cancer stem cell relevant transcription factors in a cancer stem cell, or the treatment of cancer in a subject afflicted with cancer.

The present invention provides a pharmaceutical composition comprising an amount of CMC2.24 for use in combination with a chemotherapeutic agent in inhibiting the growth of or promoting differentiation of cancer stem cells (CSCs), down-regulating cancer stem cell relevant transcription factors in a cancer stem cell, or the treatment of cancer in a subject afflicted with cancer.

BRIEF DESCRIPTION OF THE FIGURES

FIG. 5C: CSC-targeted cytotoxicity of the CMC/SBT combination. Pre-treatment of prostate CSCs (grown under stemness-promoting conditions) with CMC2.24/SBT-1214 combination for 24 hours (induction of the expression of p53 and p21) led to more profound cell death after second treatment with the same combination of drugs (lower panel).

FIG. 7B: Immunohistochemical analysis shows that, in contrast to parental tumor tissue, purified CD133$^+$ PPT2 cells do not express PSA in vitro; however, PPT2-induced NOD/SCID tumor xenografts are weakly PSA-positive.

FIG. 7C: Immunocytochemical analysis shows uniform expression of vimentin and nestin, with especially high levels of these markers of neural stem cells in large MNCs.

FIG. 7D: Western blot analysis shows expression of the pluripotency markers in nuclear and cytoplasmic fractions of the CD133$^+$ PPT2 cells. Both the nuclear and cytoplasmic fractions expressed c-Myc and were negative for p53 and p21; only the nuclear fraction expressed Oct-4 and Sox-2.

FIG. 9A: Treatment with SBT-1214 visualized the presence of large multinucleated cells, abolished the sphere-forming capacity of survivor-cells and induced delayed cell death in CD133$^+$ prostate cancer cells. Phase contrast microphotographs show that a single treatment with 1 μM SBT-1214 for 48 hr induced death of the PPT2 and PC3MM2 cells with enrichment of the large multinucleated cells (arrows).

FIG. 9B: Treatment with SBT-1214 visualized the presence of large multinucleated cells, abolished the sphere-forming capacity of survivor-cells and induced delayed cell death in CD133$^+$ prostate cancer cells. Phase contrast microphotographs show that a single treatment with 1 μM SBT-1214 for 48 hr induced death of the PPT2 and PC3MM2 cells with enrichment of the large multinucleated cells (arrows).

FIG. 9C: Post-treatment loss of the sphere-forming capacity of survivor-cells compared to untreated ones. Values are the means±SD based on 3 independent repeats.

FIG. 9D: Profound death of treated PPT2 and PC3MM2 cells during the next several days in culture.

FIG. 10A: Anti-tumor effects of SBT-1214 in vivo. NOD/SCID mice were ectopically implanted with 3,000 of CD133$^+$ PPT2 cells on the flanks. Three weeks after injection, mice were treated with weekly i.v. injections of SBT-1214 (×4: 40, 20, 20, 20 mg/kg). This treatment modality induced dramatic reduction in tumor size in the majority of the PPT2- and PC3MM2-induced tumors. Values are the means±SD; $p \leq 0.0009$ for PPT2-induced tumors (SBT-treated versus untreated controls; n=6), and $p \leq 0.0018$ for PC3MM2-induced tumors (n=6).

FIG. 10B: Anti-tumor effects of SBT-1214 in vivo. NOD/SCID mice were ectopically implanted with 3,000 of CD133$^+$ PPT2 cells on the flanks. Three weeks after injection, mice were treated with weekly i.v. injections of SBT-1214 (×4: 40, 20, 20, 20 mg/kg). This treatment modality induced dramatic reduction in tumor size in the majority of the PPT2- and PC3MM2-induced tumors. Values are the means±SD; p≤0.0009 for PPT2-induced tumors (SBT-treated versus untreated controls; n=6), and p≤0.0018 for PC3MM2-induced tumors (n=6).

FIG. 10C: Anti-tumor effects of SBT-1214 in vivo. NOD/SCID mice were ectopically implanted with 3,000 of CD133$^+$ PC3MM2 cells on the flanks. Three weeks after injection, mice were treated with weekly i.v. injections of SBT-1214 (×4: 40, 20, 20, 20 mg/kg). This treatment modality induced dramatic reduction in tumor size in the majority of the PPT2- and PC3MM2-induced tumors. Values are the means±SD; p≤0.0009 for PPT2-induced tumors (SBT-treated versus untreated controls; n=6), and p≤0.0018 for PC3MM2-induced tumors (n=6).

FIG. 10D: Anti-tumor effects of SBT-1214 in vivo. NOD/SCID mice were ectopically implanted with 3,000 of CD133$^+$ PC3MM2 cells on the flanks. Three weeks after injection, mice were treated with weekly i.v. injections of SBT-1214 (×4: 40, 20, 20, 20 mg/kg). This treatment modality induced dramatic reduction in tumor size in the majority of the PPT2- and PC3MM2-induced tumors. Values are the means±SD; p≤0.0009 for PPT2-induced tumors (SBT-treated versus untreated controls; n=6), and p≤0.0018 for PC3MM2-induced tumors (n=6).

FIG. 10E: Histopathological analysis of the residual tumors showed the presence of viable cells and accumulation of large multinucleated cells in 2 of 6 PPT2 tumors and 3 of 6 PC3MM2 tumors (representative H&E staining of untreated and SBT-1214-treated PPT2 tumor tissues is shown on E).

FIG. 10F: Histopathological analysis of the residual tumors showed the presence of viable cells and accumulation of large multinucleated cells in 3 of 6 PC3MM2 tumors (representative H&E staining of untreated and SBT-1214-treated PPT2 tumor tissues is shown on F).

FIG. 10G: Ex vivo death of the drug-treated cells in culture.

FIG. 10H: Control untreated tumor cells retained profound clonogenic and sphere-forming capacities during serial passaging.

FIG. 11A: Cytotoxic effects of the SBT-1214/CMC2.24 combination against prostate CD133$^+$ PPT2 cells. The CMC2.24 as a single agent induced bi-phasic effects on prostate cancer cell proliferation: lower concentrations of it promoted proliferation, whereas higher ones were cytotoxic. Data were obtained with standard MMT assay. Values are the means±SD of the three independent experiments with 4 repeats for each drug concentration.

FIG. 11B: Cytotoxic effects of the SBT-1214/CMC2.24 combination against prostate CD133$^+$ PC3MM2 cells. The CMC2.24 as a single agent induced bi-phasic effects on prostate cancer cell proliferation: lower concentrations of it promoted proliferation, whereas higher ones were cytotoxic. Data were obtained with standard MMT assay. Values are the means±SD of the three independent experiments with 4 repeats for each drug concentration.

DETAILED DESCRIPTION OF THE INVENTION

Figure 1:
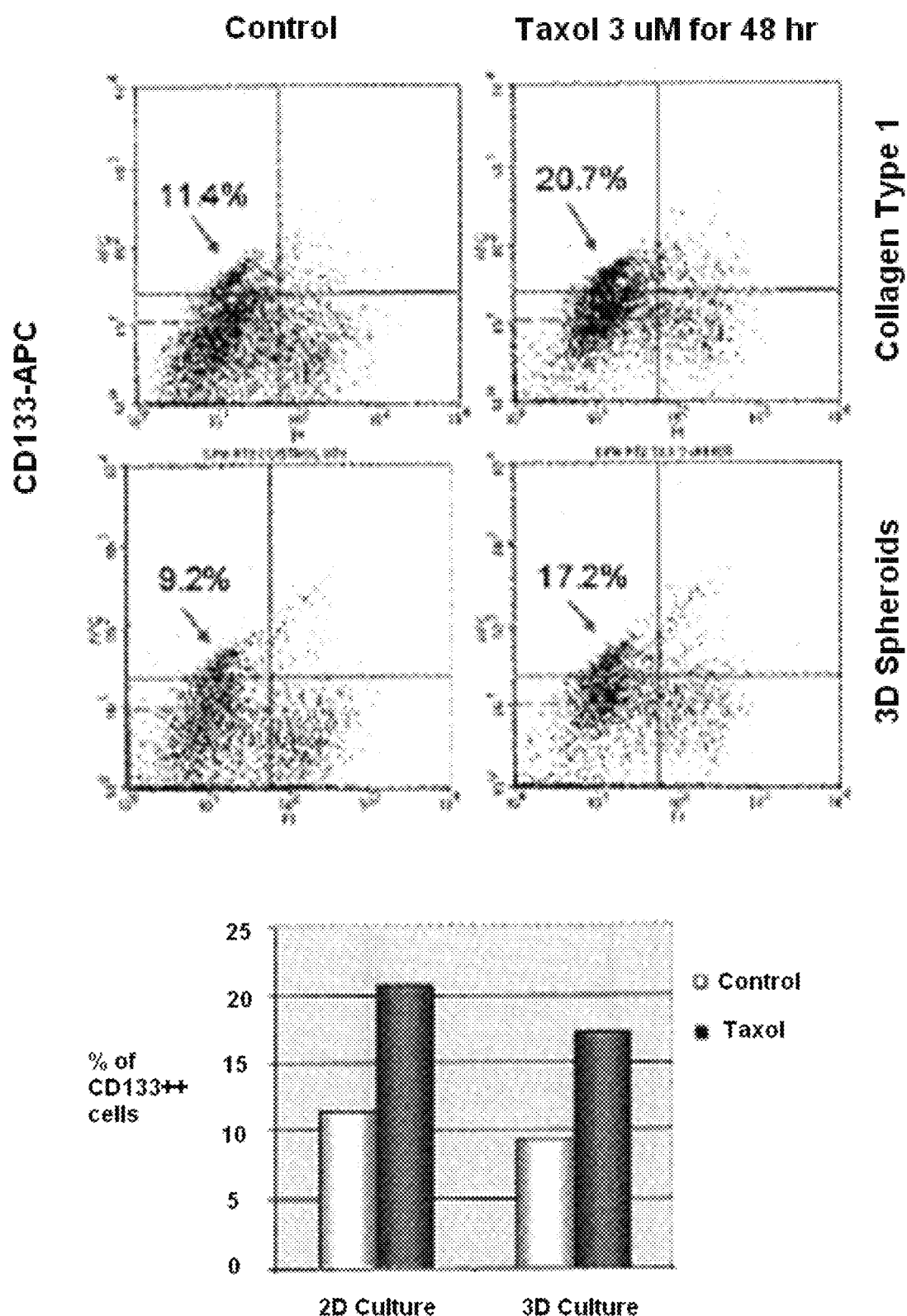
FIG. 1: The standard anti-cancer drug Taxol increases the ratios (shown by FACS analyses of cells with high expression of CD133) and actual number of CSCs (shown at right graph). CSC-enriched cell populations were cultured and treated in vitro under stemness-promoting condition, i.e. adherent to type I collagen (upper left panels) and as floating 3D spheroids (low left panels) in serum-free stem cell medium (MSCBM, Lonza).
Figure 2A:
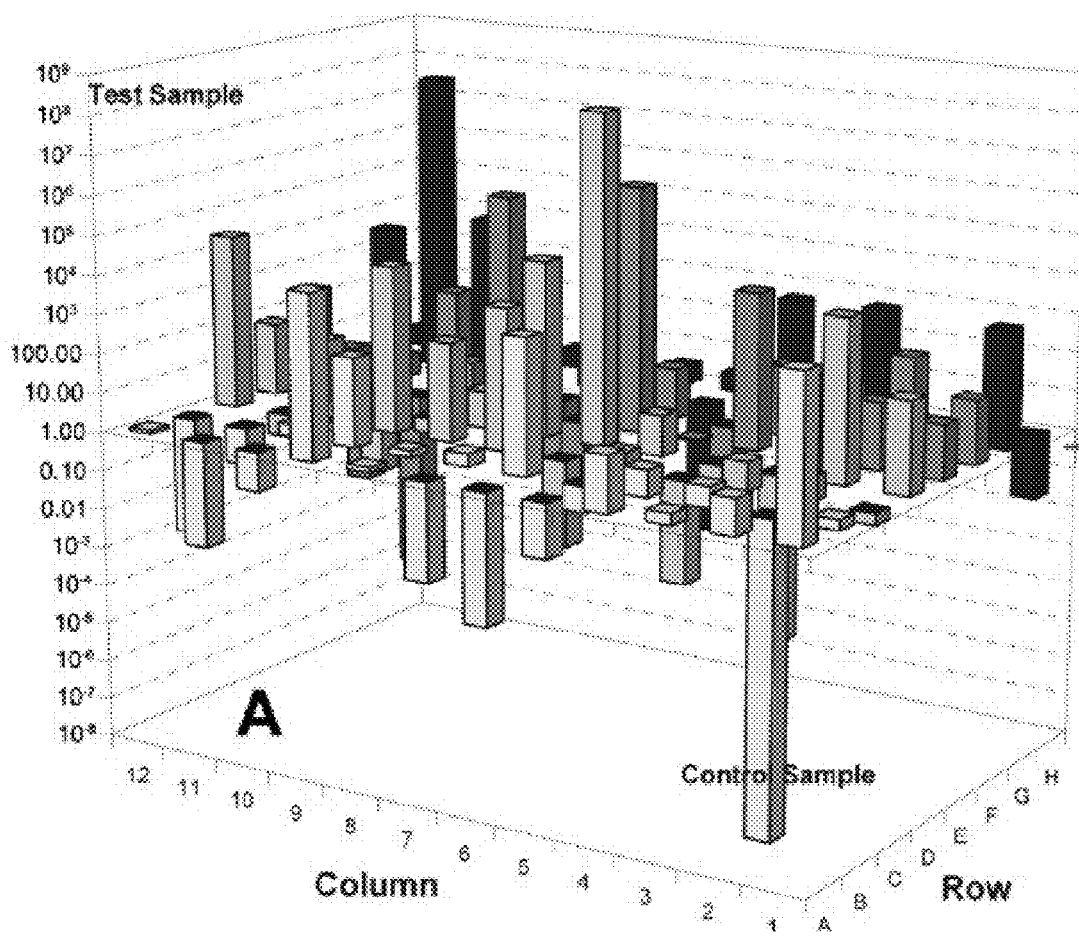
FIG. 2A: Over-expression of the majority of the analyzed 84 stem cell-related genes in the population of the patient-derived prostate cancer cells with high expression of CD133 (presumably cancer stem cells; above the base line) compared to the bulk differentiated tumor cells (below the base line). PCR Array assay (SABiosciences; PAHS-405).
Figure 2B:
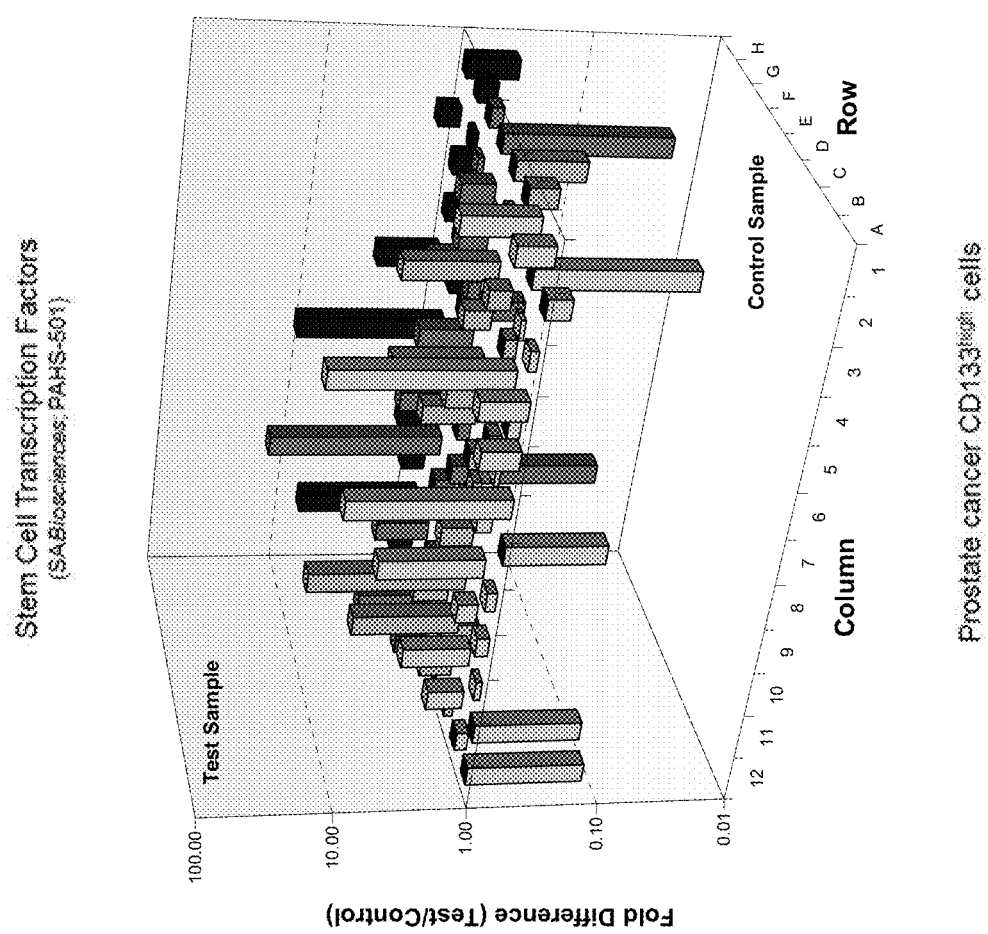
FIG. 2B: Over-expression of the stem-cell-related transcription factors in the population of the patient-derived prostate cancer cells with high expression of CD133 compared to the bulk differentiated tumor cells (below the base line). PCR Array assay (SABiosciences; PAHS-501).
Figure 2C:
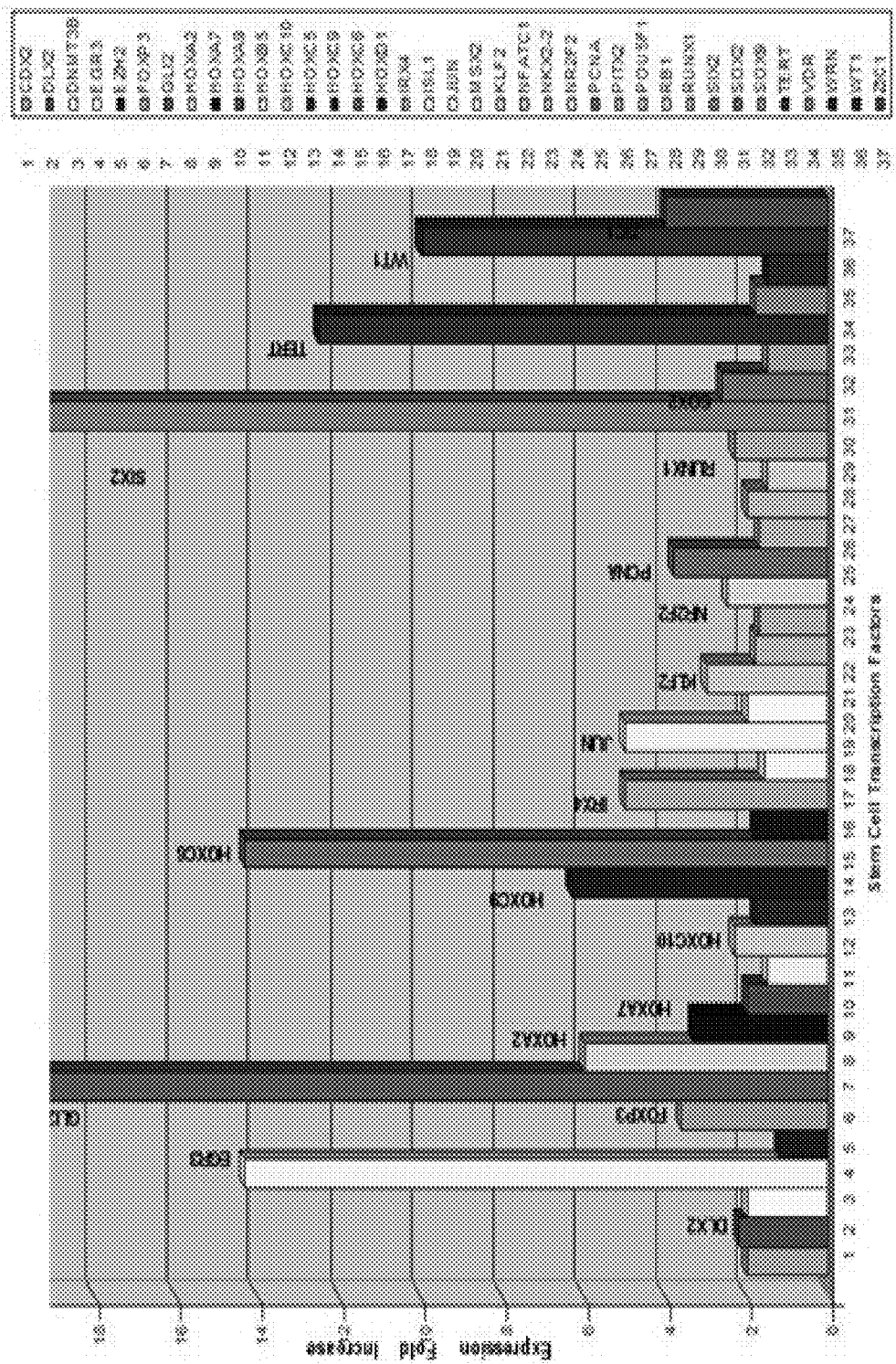
FIG. 2C: List of genes and multiple of the up-regulation of the stem cell-related transcription factors in the population of prostate CSCs with high expression of CD133 (from PCR Array analysis shown on FIG. 2B; SABiosciences; PAHS-501).
Figure 2D:
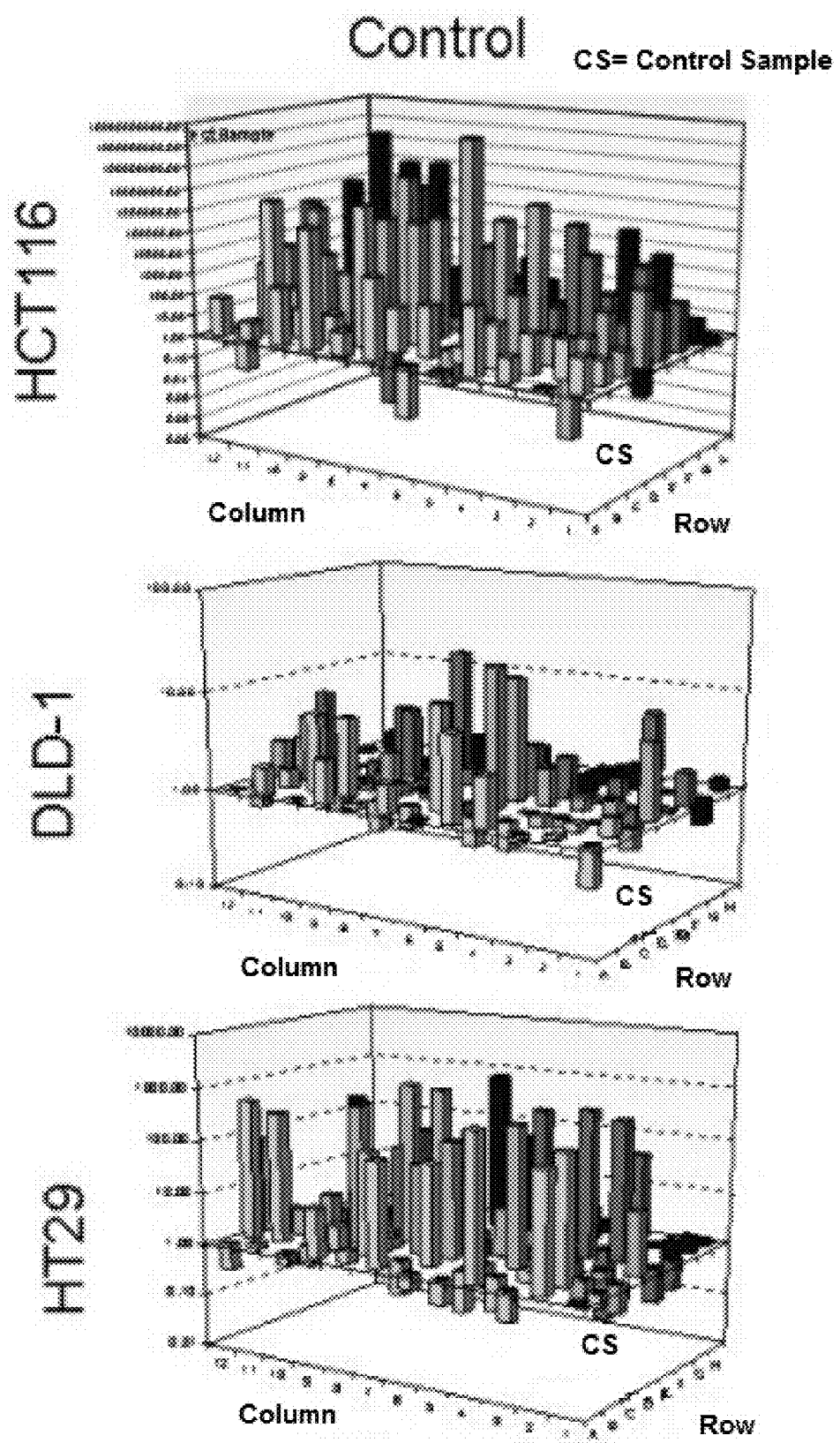
FIG. 2D: Up-regulation of stemness genes in CSCs isolated from 3 established colon cancer cell lines, HCT116, DLD-1 and HT29. Note that the most aggressive, highly metastatic HCT116 cells shows several orders of magnitude higher expression of the stemness genes compared to non-invasive DLD-1.

The present invention provides a method of inhibiting the growth of, or promoting differentiation of cancer stem cells (CSCs) comprising contacting the cancer stem cells with a compound having the structure (Formula 1):

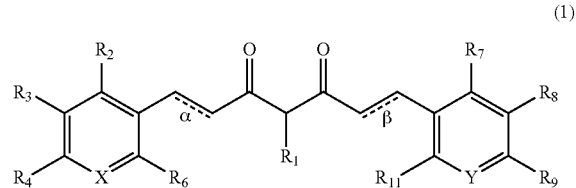

wherein
bond α and β are each, independently, present or absent;
X is $CR_5$ or N; Y is $CR_{10}$ or N;
$R_1$ is H, $CF_3$, halogen, $-NO_2$, $-OCF_3$, $-OR_{12}$, $-NHCOR_{12}$, $-CONR_{12}R_{13}$, $-CSNR_{12}R_{13}$, $-C(=NH)NR_{12}R_{13}$ $-SR_{12}$, $-SO_2R_{13}$, $-COR_{14}$, $-CSR_{14}$, $-C(=NR_{12})R_{14}$, $(=NR_{12})NR_{13}R_{14}$, $-SOR_{12}$, $-SONR_{12}R_{13}$, $-SO_2NR_{12}R_{13}$, $-P(O)R_{12}$, $-PH(=O)OR_{12}$ $-P(=O)(OR_{12})(OR_{13})$, or $-P(OR_{12})(OR_{13})$
  wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;
$R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

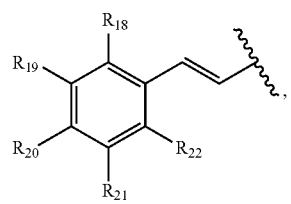

wherein $R_{15}$ is H, $C_{3-10}$ alkyl, $C_{2-10}$ alkenyl, $C_{2-10}$ alkynyl;
  $R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, —$SOR_{23}$, —$POR_{23}$, —C(=S)$R_{23}$, —C(=NH)$R_{23}$, —C(=N)$R_{23}$, —P(=O)($OR_{23}$)($OR_{24}$), —P($OR_{23}$)($OR_{24}$), —C(=S)$R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein when $R_1$ is H, then $R_3$, $R_4$, $R_5$, $R_8$, $R_9$, or $R_{10}$, is halogen, —$NO_2$, —CN, —$NR_{28}R_{29}$, —$NHR_{28}R_{29}^+$, —$SR_{28}$, —$SO_2R_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein each occurrence of alkyl, alkenyl, or alkynyl is branched or unbranched, unsubstituted or substituted;

or a pharmaceutically acceptable salt thereof.

The present invention provides a method of down-regulating cancer stem cell-relevant transcription factors comprising contacting the cancer stem cell with a compound having the structure:

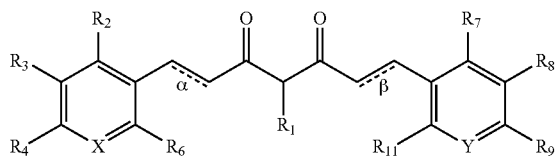

wherein bond α and β are each, independently, present or absent;

X is $CR_5$ or N; Y is $CR_{10}$ or N;

$R_1$ is H, $CF_3$, halogen, —$NO_2$, —$OCF_3$, —$OR_{12}$, —NH-$COR_{12}$, —$CONR_{12}R_{13}$, —$CSNR_{12}R_{13}$, —C(=NH)$NR_{12}R_{13}$ —$SR_{12}$, —$SO_2R_{13}$, —$COR_{14}$, —$CSR_{14}$, —C(=$NR_{12}$)$R_{14}$, —C(=$NR_{12}$)$NR_{12}R_{14}$, —$SOR_{12}$, —$SONR_{12}R_{13}$, —$SO_2NR_{12}R_{13}$, —P(O)$R_{12}$, —PH(=O)$OR_{12}$ —P(=O)($OR_{12}$)($OR_{13}$), or —P($OR_{12}$)($OR_{12}$), wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, —$OR_{15}$, —$NR_{16}R_{17}$, or

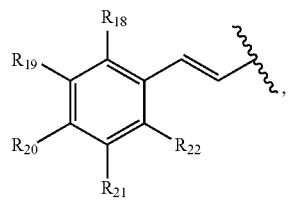

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, —$SOR_{23}$, —$POR_{23}$, —C(=S)$R_{23}$, —C(=NH)$R_{23}$, —C(=N)$R_{23}$, —P(=O)($OR_{23}$)($OR_{24}$), —P($OR_{23}$)($OR_{24}$), —C(=S)$R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein when $R_1$ is H, then $R_3$, $R_4$, $R_5$, $R_8$, $R_9$, or $R_{10}$, is halogen, —$NO_2$, —CN, —$NR_{28}R_{29}$, —$NHR_{28}R_{29}^+$, —$SR_{28}$, —$SO_2R_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein each occurrence of alkyl, alkenyl, or alkynyl is branched or unbranched, unsubstituted or substituted;

or a pharmaceutically acceptable salt thereof.

In some embodiments, the method further comprising contacting the cancer stem cell with a chemotherapeutic agent.

In some embodiments, the method wherein the cancer stem cell-relevant transcription factor is, but not limited to, CDX2, DLX2, EGR3, FOXP3, GLI2, HOXA2, HOXA7, HOXB3, HOXB8, HOXC10, HOXC9, HOXC6, HOXC4, HOXC5, IRX4, JUN, KLF2, NFATC1, NR2F2, PITX3, POU5F1, RUNX1, WT1, c-MYC, or SOX-2.

In some embodiments, the method wherein the cancer stem cell-relevant transcription factor is each of CDX2, DLX2, EGR3, FOXP3, GLI2, HOXA2, HOXA7, HOXB3, HOXB8, HOXC10, HOXC9, HOXC6, HOXC4, HOXC5, IRX4, JUN, KLF2, NFATC1, NR2F2, PITX3, POU5F1, RUNX1, WT1, c-MYC, and SOX-2.

In some embodiments, the method wherein the cancer stem cell-relevant transcription factors are at least five (5) transcription factors selected from the group consisting of CDX2, DLX2, EGR3, FOXP3, GLI2, HOXA2, HOXA7, HOXB3, HOXB8, HOXC10, HOXC9, HOXC6, HOXC4, HOXC5, IRX4, JUN, KLF2, NFATC1, NR2F2, PITX3, POU5F1, RUNX1, WT1, c-MYC, and SOX-2.

The present invention provides a method of inhibiting the growth of a tumor comprising cancer stem cells (CSCs) by contacting the tumor with a compound having the structure:

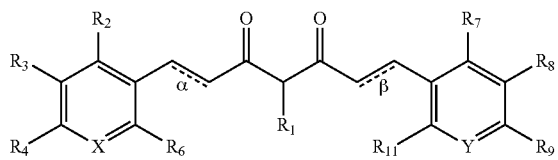

wherein bond α and β are each, independently, present or absent;
X is $CR_5$ or N; Y is $CR_{40}$ or N;
$R_1$ is H, $CF_3$, halogen, $-NO_2$, $-OCF_3$, $-OR_{12}$, $-NH-COR_{12}$, $-CONR_{12}R_{13}$, $-CSNR_{12}R_{13}$, $-C(=NH)NR_{12}R_{13}$, $-SR_{12}$, $-SO_2R_{13}$, $-COR_{14}$, $-CSR_{14}$, $-C(=NR_{12})R_{14}$, $-C(=NR_{12})NR_{13}R_{14}$, $-SOR_{12}$, $-SONR_{12}R_{13}$, $-SO_2NR_{12}R_{13}$, $-P(O)R_{12}$, $-PH(=O)OR_{12}$ $-P(=O)(OR_{12})(OR_{13})$, or $-P(OR_{12})(OR_{13})$, wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

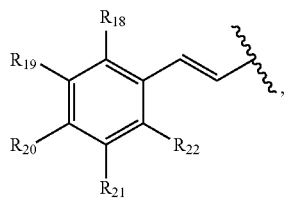

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $-SOR_{23}$, $-POR_{23}$, $-C(=S)R_{23}$, $-C(=NH)R_{23}$, $-C(=N)R_{23}$, $-P(=O)(OR_{23})(OR_{24})$, $-P(OR_{23})(OR_{24})$, $-C(=S)R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, $-NO_2$, $-CN$, $-NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}^+$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein when $R_1$ is H, then $R_3$, $R_4$, $R_5$, $R_8$, $R_9$, or $R_{10}$, is halogen, $-NO_2$, $-CN$, $-NR_{28}R_{29}$, $-NHR_{28}R_{29}^+$, $-SR_{28}$, $-SO_2R_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein each occurrence of alkyl, alkenyl, or alkynyl is branched or unbranched, unsubstituted or substituted;

or a pharmaceutically acceptable salt thereof.

In some embodiments of the method, the compound having the structure

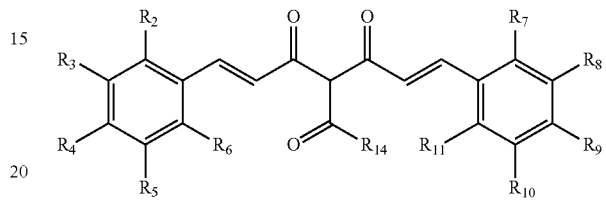

wherein $R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

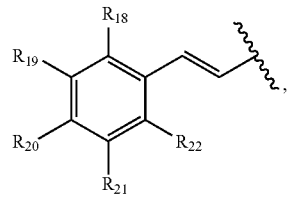

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, $-NO_2$, $-CN$, $-NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, or $C_{2-10}$ alkynyl; and wherein each occurrence of alkyl, alkenyl, or alkynyl is branched or unbranched, unsubstituted or substituted; and or a salt thereof.

In some embodiments of the method, the compound wherein at least one of $R_2$, $R_3$, $R_4$, $R_5$, and $R_6$ and at least one of $R_7$, $R_8$, $R_9$, $R_{10}$, and $R_{11}$, are each, independently, $-OR_{28}$.

In some embodiments of the method, the compound wherein $R_{14}$ is methoxy, $-OR_{15}$ or $-NR_{16}R_{17}$, wherein $R_{15}$ is H, $C_{3-10}$ alkyl, $C_{2-10}$ alkenyl, or $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

or a salt thereof.

In some embodiments of the method, the compound wherein $R_{14}$ is methoxy or —$NR_{16}R_{17}$, wherein $R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

or a salt thereof.

In some embodiments of the method, the compound wherein wherein $R_{14}$ is —$OR_{15}$, wherein $R_{15}$ is H, $C_{3-10}$ alkyl, $C_{2-10}$ alkenyl, or $C_{2-10}$ alkynyl;

or a salt thereof.

In some embodiments of the method, the compound wherein $R_{14}$ is —$NR_{16}R_{17}$, wherein $R_{16}$ and $R_{17}$ are each, independently, H or aryl;

$R_2$, $R_3$, $R_4$, $R_5$, $R_6$, $R_7$, $R_8$, $R_9$, $R_{10}$, and $R_{11}$ are each independently, H, —$NR_{28}R_{29}$, or —$OR_{28}$, wherein $R_{28}$ and $R_{29}$ are each, H or $C_{1-10}$ alkyl;

or a salt thereof.

In some embodiments of the method, wherein $R_{14}$ is —NH-phenyl;

$R_2$, $R_5$, $R_6$, $R_7$, $R_{10}$, and $R_{11}$ are each H;

$R_3$, $R_4$, $R_8$, and $R_9$ are each, independently, H, —OH, or —$OCH_3$;

or a salt thereof.

In some embodiments, the method wherein the compound inhibits the growth of cancer stem cells.

In some embodiments, the method wherein the compound promotes the differentiation of cancer stem cells.

In some embodiments, the method wherein the compound inhibits cancer stem cell-relevant transcription factors.

In some embodiments, the method wherein the compound stimulates the formation of pro-apoptotic proteins such as P21 and P53.

In some embodiments, the method wherein the compound up-regulates pro-apoptotic proteins such as P21 and P53.

In some embodiments, the method wherein the compound induces expression of P21 and/or P53 in the cancer stem cells.

In some embodiments, the method wherein the compound induces expression of P21 and/or P53 in the cancer cells.

In some embodiments, the method further comprising contacting the tumor with a chemotherapeutic agent.

In some embodiments, the method wherein the growth of cancer stem cells fails to be inhibited by, or the differentiation of cancer stem cells is not promoted by, or the cancer stem cell-relevant transcription factors are not inhibited by, the chemotherapeutic agent.

In some embodiments, the method wherein the tumor growth is resistant to a chemotherapeutic agent, due to the presence of cancer stem cells in the tumor.

In some embodiments, a method of inhibiting the growth of or promoting differentiation and destruction of cancer stem cells (CSCs).

In some embodiments, the method wherein the compound is CMC2.24, which has the structure (ketonic form)

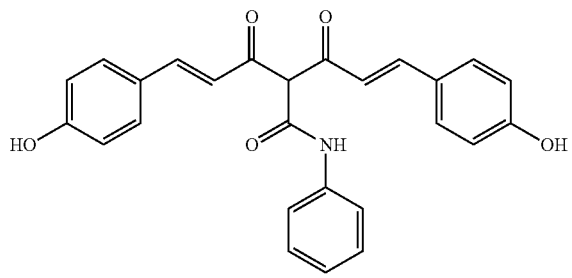 [SMILES: O=C(/C=C/c1ccc(O)cc1)C(C(=O)/C=C/c1ccc(O)cc1)C(=O)Nc1ccccc1]

or a pharmaceutically acceptable salt thereof.

Figure 6:
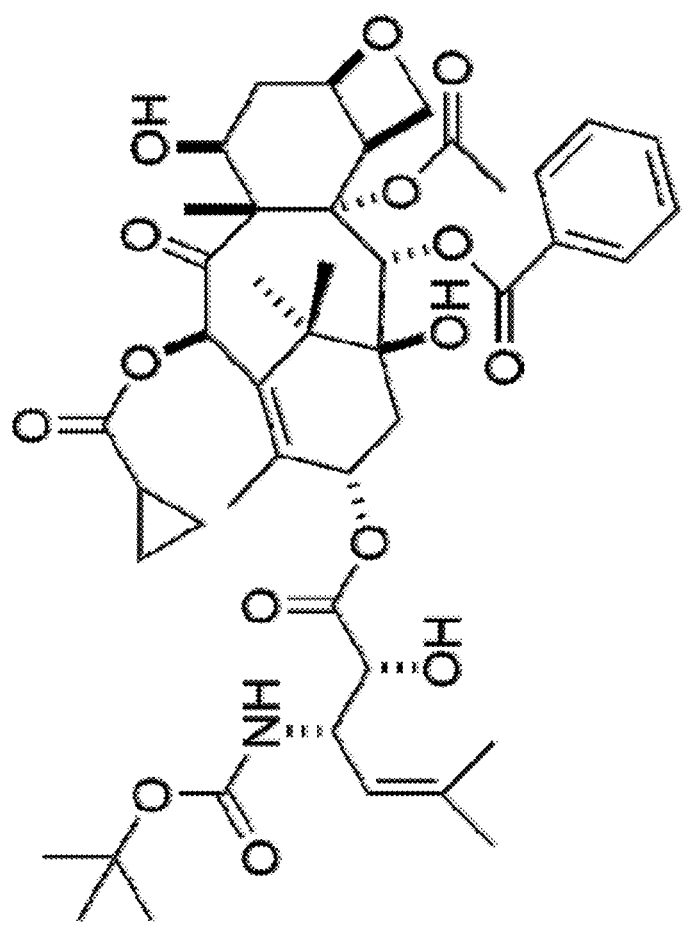
FIG. 6: Structure of SBT-1214.

In some embodiments, the method wherein the chemotherapeutic agent is SBT-1214, which has the structure shown in FIG. 6.

In some embodiments, the method wherein the chemotherapeutic agent is LB100, which is also known as compound LB1, disclosed in U.S. Pat. No. 7,998,957 B2 and Lu, J, et al. *J. Neurosurg.* 2010, 113, 225-233.

In some embodiments, the method wherein the chemotherapeutic agent is puromycin, 5-fluorocytidine, 2'-deoxy-5-fluorocytidine, 5'-deoxy-5-fluorocytidine, 5'-deoxy-5-fluorocytidine, gemcitabine, cytarabine, cladribine, troxacitabine, abiraterone acetate, abraxane, adriamycin, afinitor, alimta, aloxi, amboclorin, aminolevulinic acid, anastrozole, aprepitant, aromasin, axitinib, azacitidine, bendamustine hydrochloride, bexarotene, bleomycin, bortezomib, cabazitaxel, capecitabine, cerubidine, clofarabine, clofarex, crizotinib, dacarbazine, dasatinib, daunorubicin hydrochloride, decitabine, degarelix, dexrazoxane hydrochloride, docetaxel, doxil, deoxorubicin, ellence, epirubicin hydrochloride, eribulin mesylate, erlotinib hydrochloride, etoposide, evacet, everolimus, fludara, fludarabine phosphate, fluorouracil, fulvestrant, gefitinib, gemcitabine hydrochloride, imatinib mesylate, imiquimod, irinotecan hydrochloride, ixabepilone, lapatinib ditosylate, lenalidomide, letrozole, leucovorin calcium, leuprorelin, levulan, lomustine, lupron, matulane, methotrexate, mitomycin C, navelbine, nelarabine, nexavar, nilotinib, nolvadex, palonosetron hydrochloride, pazopanib hydrochloride, pemetrexed disodium, pralatrexate, prednisone, procarbazine hydrochloride, raloxifene hydrochloride, ruxolitinib phosphate, sorafenib tosylate, sunitinib malate, tamoxifen citrate, taxol, taxotere, temozolomide, temsirolimus, topotecan hydrochloride, toremifene, vandetanib, vemurafenib, vinblastine sulfate, vincristine sulfate, vinorelbine tartrate, vismodegib, wellcovorin, xalkori, zevalin, zinecard, zoledronic acid, paclitaxel, anthracendione, cyclophosphamide, etoposide, LB100, cisplatin, or oxaliplatin.

In some embodiments of the method, wherein the compound has the structure

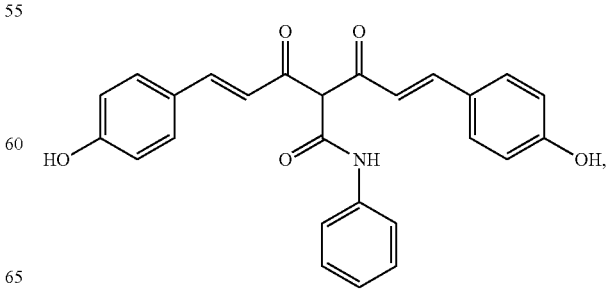

and the chemotherapeutic agent is SBT-1214.

In some embodiments of the method, wherein the compound has the structure

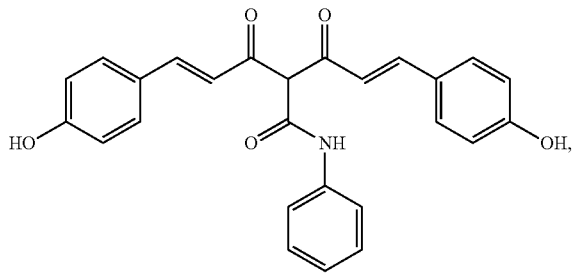 [SMILES: O=C(/C=C/c1ccc(O)cc1)C(C(=O)/C=C/c1ccc(O)cc1)C(=O)Nc1ccccc1]

and the chemotherapeutic agent is puromycin, 5-fluorocytidine, 2'-deoxy-5-fluorocytidine, 5'-deoxy-5-fluorocytidine, 5'-deoxy-5-fluorocytidine, gemcitabine, cytarabine, cladribine, troxacitabine, abiraterone acetate, abraxane, adriamycin, afinitor, alimta, aloxi, amboclorin, aminolevulinic acid, anastrozole, aprepitant, aromasin, axitinib, azacitidine, bendamustine hydrochloride, bexarotene, bleomycin, bortezomib, cabazitaxel, capecitabine, cerubidine, clofarabine, clofarex, crizotinib, dacarbazine, dasatinib, daunorubicin hydrochloride, decitabine, degarelix, dexrazoxane hydrochloride, docetaxel, doxil, deoxorubicin, ellence, epirubicin hydrochloride, eribulin mesylate, erlotinib hydrochloride, etoposide, evacet, everolimus, fludara, fludarabine phosphate, fluorouracil, fulvestrant, gefitinib, gemcitabine hydrochloride, imatinib mesylate, imiquimod, irinotecan hydrochloride, ixabepilone, lapatinib ditosylate, lenalidomide, letrozole, leucovorin calcium, leuprorelin, levulan, lomustine, lupron, matulane, methotrexate, mitomycin C, navelbine, nelarabine, nexavar, nilotinib, nolvadex, palonosetron hydrochloride, pazopanib hydrochloride, pemetrexed disodium, pralatrexate, prednisone, procarbazine hydrochloride, raloxifene hydrochloride, ruxolitinib phosphate, sorafenib tosylate, sunitinib malate, tamoxifen citrate, taxol, taxotere, temozolomide, temsirolimus, topotecan hydrochloride, toremifene, vandetanib, vemurafenib, vinblastine sulfate, vincristine sulfate, vinorelbine tartrate, vismodegib, wellcovorin, xalkori, zevalin, zinecard, zoledronic acid, paclitaxel, anthracendione, cyclophosphamide, etoposide, LB100, cisplatin, or oxaliplatin.

In some embodiments, the method wherein the cancer stem cells are colon cancer stem cells or prostate cancer stem cells.

The present invention provides a method of cancer treatment by inhibition of the stemness state of CSCs and/or promotion of differentiation and/or the inhibition of angiogenesis and/or the induction of apoptosis by contacting the cancerous growth either systemically or topically, with a compound having the structure:

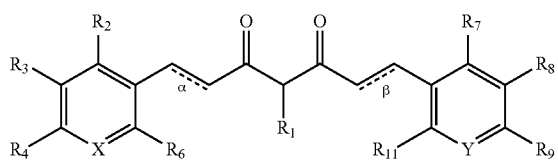

wherein
bond α and β are each, independently, present or absent;
X is $CR_5$ or N; Y is $CR_{10}$ or N;

$R_1$ is H, $CF_3$, halogen, $-NO_2$, $-OCF_3$, $-OR_{12}$, $-NHCOR_{12}$, $CONR_{12}R_{13}$, $-CSHR_{12}R_{13}$, $-C(=NH)NR_{12}R_{13}$ $-SR_{12}$, $-SO_2R_{13}$, $-COR_{14}$, $-CSR_{14}$, $-C(=NR_{12})R_{14}$, $-C(=NR_{12})NR_{13}R_{14}$, $-SOR_{12}$, $-SONR_{12}R_{13}$, $-SO_2NR_{12}R_{13}$ $P(O)R_{12}$, $-PH(=O)OR_{12}$ $-P(=O)(OR_{12})(OR_{13})$, or $-P(OR_{12})(OR_{13})$, wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;

$R_{14}$ is $C_{2-10}$ alkyl, $C_{2-10}$ alkenyl, $C_{2-10}$ alkynyl, heteroaryl, heterocyclyl, methoxy, $-OR_{15}$, $-NR_{16}R_{17}$, or

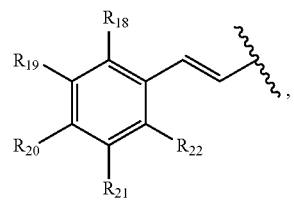

wherein $R_{15}$ is H, $C_{3-10}$ alkyl, $C_{2-10}$ alkenyl, $C_{2-20}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, $-NO_2$, $-CN$, $-NR_{23}R_{24}$, $-SR_{23}$, $-SO_2R_{23}$, $-CO_2R_{23}$, $-OR_{25}$, $CF_3$, $-SOR_{23}$, $-POR_{23}$, $-C(=S)R_{23}$, $-C(=NH)R_{23}$, $-C(=N)R_{23}$, $-P(=O)(OR_{23})(OR_{24})$, $-P(OR_{23})(OR_{24})$, $-C(=S)R_{23}$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, $-NO_2$, $-CN$, $-NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, $-NO_2$, $-CN$, $-NR_{28}R_{29}$, $-NHR_{28}R_{29}^+$, $-SR_{28}$, $-SO_2R_{28}$, $-OR_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein when $R_1$ is H, then $R_3$, $R_4$, $R_5$, $R_8$, $R_9$, or $R_{10}$, is halogen, $-NO_2$, $-CN$, $-NR_{28}R_{29}$, $-NHR_{28}R_{29}^+$, $-SR_{28}$, $-SO_2R_{28}$, $-CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, $C_{2-10}$ alkynyl, or $-C(=O)$-heterocyclyl; and wherein each occurrence of alkyl, alkenyl, or alkynyl is branched or unbranched, unsubstituted or substituted;

or a pharmaceutically acceptable salt thereof.

The present invention provides a method of treating a patient suffering from cancer comprising administering to the patient a compound having the structure:

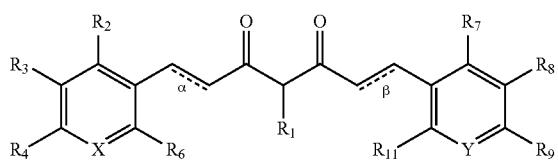

wherein
bond α and β are each, independently, present or absent;
X is $CR_5$ or N; Y is $CR_{10}$ or N;
$R_1$ is H, $CF_3$, halogen, —$NO_2$, —$OCF_3$, —$OR_{12}$, —NH-$COR_{12}$, —$CONR_{12}R_{13}$, —$CSNR_{12}R_{13}$, —C(=NH)$NR_{12}R_{13}$ —$SR_{12}$, —$SO_2R_{13}$, —$COR_{14}$, —$CSR_{14}$, —C(=$NR_{12}$)$R_{14}$, —C(=$NR_{12}$)$NR_{13}R_{14}$, —$SOR_{12}$, —$SONR_{12}R_{13}$, —$SO_2NR_{12}R_{13}$, —P(O)$R_{12}$, —PH(=O)$OR_{12}$ —P(=O)($OR_{12}$)($OR_{13}$), or —P($OR_{12}$)($OR_{13}$),
  wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;
  $R_{14}$ is $C_{2-10}$ alkyl, $C_{2-10}$ alkenyl, $C_{2-10}$ alkynyl, heteroaryl, heterocyclyl, methoxy, —$OR_{15}$, —$NR_{16}R_{17}$, or

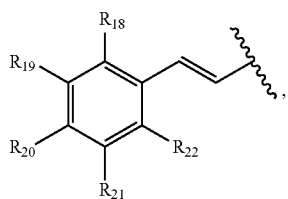

wherein $R_{15}$ is H, $C_{3-10}$ alkyl, $C_{2-10}$ alkenyl, $C_{2-10}$ alkynyl;
  $R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;
  $R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, —$SOR_{23}$, —$POR_{23}$, —C(=S)$R_{23}$, —C(=NH)$R_{23}$, —C(=N)$R_{23}$, —P(=O)($OR_{23}$)($OR_{24}$), —P($OR_{23}$)($OR_{24}$), —C(=S)$R_{23}$, $C_{1-10}$ alkyl, $C_{2-10}$ alkenyl, $C_{2-10}$ alkynyl, aryl, heteroaryl, or heterocyclyl;
    wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;
  $R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;
    wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;
  $R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$NHR_{28}R_{29}^+$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;
    wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and
    wherein when $R_1$ is H, then $R_3$, $R_4$, $R_5$, $R_8$, $R_9$, or $R_{10}$, is halogen, —$NO_2$, —CN, —$NR_{28}R_{29}$, —$NHR_{28}R_{29}^+$, —$SR_{28}$, —$SO_2R_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;
  wherein $R_{28}$ and $R_{29}$ are each, H, $CF_3$, $C_{1-10}$ alkyl, $C_{2-10}$ alkenyl, $C_{2-10}$ alkynyl, or —C(=O)-heterocyclyl; and wherein each occurrence of alkyl, alkenyl, or alkynyl is branched or unbranched, unsubstituted or substituted;
or a pharmaceutically acceptable salt thereof.

In some embodiments, the method further comprising treating the patient with a chemotherapeutic agent.

In some embodiments, a method of treating a patient suffering from prostate cancer or colon cancer comprising administering to the patient a compound having the structure:

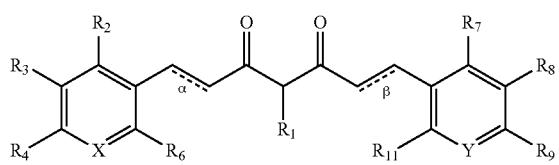

wherein
bond α and β are each, independently, present or absent;
X is $CR_5$ or N; Y is $CR_{10}$ or N;
$R_1$ is H, $CF_3$, halogen, —$NO_2$, —$OCF_3$, —$OR_{12}$, —NH-$COR_{12}$, —$CONR_{12}R_{13}$, —$CSNR_{12}R_{13}$, —C(=NH)$NR_{12}R_{13}$ —$SR_{12}$, —$SO_2R_{13}$, —$COR_{14}$, —$CSR_{14}$, —C(=$NR_{12}$)$R_{14}$, —C(=$NR_{12}$)$NR_{13}R_{14}$, —$SOR_{12}$, —$SONR_{12}R_{13}$, —$SO_2NR_{12}R_{13}$, —P(O)$R_{12}$, —PH(=O)$OR_{12}$ —P(=O)($OR_{12}$)($OR_{13}$), or —P($OR_{12}$)($OR_{13}$),
  wherein $R_{12}$ and $R_{13}$ are each, independently, H, $C_{1-10}$ alkyl, $C_{2-10}$ alkenyl, $C_{2-10}$ alkynyl, aryl, heteroaryl, or heterocyclyl;
  $R_{14}$ is $C_{2-10}$ alkyl, $C_{2-10}$ alkenyl, alkynyl, heteroaryl, heterocyclyl, methoxy, —$OR_{15}$, —$NR_{16}R_{17}$, or

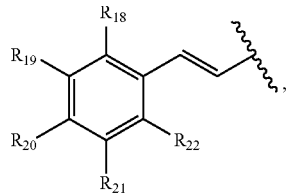

wherein $R_{15}$ is H, $C_{3-10}$ alkyl, $C_{2-10}$ alkenyl, $C_{2-10}$ alkynyl; $R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;
  $R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, —$SOR_{23}$, —$POR_{23}$, —C(=S)$R_{23}$, —C(=NH)$R_{23}$, —C(=N)$R_{23}$, —P(=O)($OR_{23}$)($OR_{24}$), —P($OR_{23}$)($OR_{24}$), —C(=S)$R_{23}$, $C_{1-10}$ alkyl, $C_{2-10}$ alkenyl, $C_{2-10}$ alkynyl, aryl, heteroaryl, or heterocyclyl;
    wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;
  $R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;
    wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;
  $R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —NHR$_{28}$R$_{29}^+$, —SR$_{28}$, —SO$_2$R$_{28}$, —OR$_{28}$, —CO$_2$R$_{28}$, CF$_3$, C$_{1-10}$ alkyl, C$_{2-10}$ alkenyl, C$_{2-10}$ alkynyl, aryl, heteroaryl, or heterocyclyl;

wherein R$_{28}$ and R$_{29}$ are each, H, CF$_3$, C$_{1-10}$ alkyl, C$_{2-10}$ alkenyl, C$_{2-10}$ alkynyl, or —C(=O)-heterocyclyl; and wherein when R$_1$ is H, then R$_3$, R$_4$, R$_5$, R$_8$, R$_9$, or R$_{10}$, is halogen, —NO$_2$, —CN, —NR$_{28}$R$_{29}$, —NHR$_{28}$R$_{29}^+$, —SR$_{28}$, —SO$_2$R$_{28}$, —CO$_2$R$_{28}$, CF$_3$, C$_{1-10}$ alkyl, C$_{2-10}$ alkenyl, C$_{2-10}$ alkynyl, aryl, heteroaryl, or heterocyclyl;

wherein R$_{28}$ and R$_{29}$ are each, H, CF$_3$, C$_{1-10}$ alkyl, C$_{2-10}$ alkenyl, C$_{2-10}$ alkynyl, or —C(=O)-heterocyclyl; and wherein each occurrence of alkyl, alkenyl, or alkynyl is branched or unbranched, unsubstituted or substituted;

or a pharmaceutically acceptable salt thereof.

The present invention provides a compound for use in inhibiting the growth of or promoting differentiation of cancer stem cells (CSCs), down-regulating cancer stem cell relevant transcription factors in a cancer stem cell, or the treatment of cancer in a subject afflicted with cancer, the compound having the structure:

wherein bond α and β are each, independently, present or absent;

X is CR$_5$ or N; Y is CR$_{10}$ or N;

R$_1$ is H, CF$_3$, halogen, —NO$_2$, —OCF$_3$, —OR$_{12}$, —NH-COR$_{12}$, —CONR$_{12}$R$_{13}$, —CSNR$_{12}$R$_{13}$, —C(=NH)NR$_{12}$R$_{13}$ —SR$_{12}$, —SO$_2$R$_{13}$, —COR$_{14}$, —CSR$_{14}$, —C(=NR$_{12}$)R$_{14}$, —C(=NR$_{12}$)NR$_{13}$R$_{14}$, —SOR$_{12}$, —SONR$_{12}$R$_{13}$, —SO$_2$NR$_{12}$R$_{13}$, —P(O)R$_{12}$, —PH(=O)OR$_{12}$ —P(=O)(OR$_{12}$)(OR$_{13}$), or —P(OR$_{12}$)(OR$_{13}$), wherein R$_{12}$ and R$_{13}$ are each, independently, H, C$_{1-10}$ alkyl, C$_{2-10}$ alkenyl, C$_{2-10}$ alkynyl, aryl, heteroaryl, or heterocyclyl;

R$_{14}$ is C$_{2-10}$ alkyl, C$_{2-10}$ alkenyl, C$_{2-10}$ alkynyl, heteroaryl, heterocyclyl, methoxy, —OR$_{15}$, —NR$_{16}$R$_{17}$, or wherein R$_{15}$ is H, C$_{3-10}$ alkyl, C$_{2-10}$ alkenyl, C$_{2-10}$ alkynyl;

R$_{16}$ and R$_{17}$ are each, independently, H, C$_{1-10}$ alkyl, C$_{2-10}$ alkenyl, C$_{2-10}$ alkynyl, aryl, heteroaryl, or heterocyclyl;

R$_{18}$, R$_{19}$, R$_{21}$, and R$_{22}$ are each independently H, halogen, —NO$_2$, —CN, —NR$_{23}$R$_{24}$, —SR$_{23}$, —SO$_2$R$_{23}$, —CO$_2$R$_{23}$, —OR$_{25}$, CF$_3$, —SOR$_{23}$, —POR$_{23}$, —C(=S)R$_{23}$, —C(=NH)R$_{23}$, —C(=N)R$_{23}$, —P(=O)(OR$_{23}$)(OR$_{24}$), —P(OR$_{23}$)(OR$_{24}$), —C(=S)R$_{23}$, C$_{1-10}$ alkyl, C$_{2-10}$ alkenyl, C$_{2-10}$ alkynyl, aryl, heteroaryl, or heterocyclyl;

wherein R$_{23}$, R$_{24}$, and R$_{25}$ are each, independently, H, C$_{1-10}$ alkyl, C$_{2-10}$ alkenyl, C$_{2-10}$ alkynyl, aryl, heteroaryl, or heterocyclyl;

R$_{20}$ is halogen, —NO$_2$, —CN, —NR$_{26}$R$_{27}$, CF$_3$, C$_{1-10}$ alkyl, C$_{2-10}$ alkenyl, C$_{2-10}$ alkynyl, aryl, heteroaryl, or heterocyclyl;

wherein R$_{26}$ and R$_{27}$ are each, independently, H, C$_{1-10}$ alkyl, C$_{2-10}$ alkenyl, C$_{2-10}$ alkynyl, aryl, heteroaryl, or heterocyclyl;

R$_2$, R$_3$, R$_4$, R$_5$, R$_6$, R$_7$, R$_8$, R$_9$, R$_{10}$, and R$_{11}$ are each independently, H, halogen, —NO$_2$, —CN, —NR$_{28}$R$_{29}$, —NHR$_{28}$R$_{29}^+$, —SR$_{28}$, —SO$_2$R$_{28}$, —OR$_{28}$, —CO$_2$R$_{28}$, CF$_3$, C$_{1-10}$ alkyl, C$_{2-10}$ alkenyl, C$_{2-10}$ alkynyl, aryl, heteroaryl, or heterocyclyl;

wherein R$_{28}$ and R$_{29}$ are each, H, CF$_3$, C$_{1-10}$ alkyl, C$_{2-10}$ alkenyl, C$_{2-10}$ alkynyl, or —C(=O)-heterocyclyl; and wherein when R$_1$ is H, then R$_3$, R$_4$, R$_5$, R$_8$, R$_9$, or R$_{10}$, is halogen, —NO$_2$, —CN, —NR$_{28}$R$_{29}$, —NHR$_{28}$R$_{29}^+$, —SR$_{28}$, —SO$_2$R$_{28}$, —CO$_2$R$_{28}$, CF$_3$, C$_{1-10}$ alkyl, C$_{2-10}$ alkenyl, C$_{2-10}$ alkynyl, aryl, heteroaryl, or heterocyclyl;

wherein R$_{28}$ and R$_{29}$ are each, H, CF$_3$, C$_{1-10}$ alkyl, C$_{2-10}$ alkenyl, C$_{2-10}$ alkynyl, or —C(=O)-heterocyclyl; and wherein each occurrence of alkyl, alkenyl, or alkynyl is branched or unbranched, unsubstituted or substituted;

or a pharmaceutically acceptable salt thereof.

The present invention provides CMC2.24 for use in combination with a chemotherapeutic agent in inhibiting the growth of or promoting differentiation of cancer stem cells (CSCs), down-regulating cancer stem cell relevant transcription factors in a cancer stem cell, or the treatment of cancer in a subject afflicted with cancer.

The present invention provides a pharmaceutical composition comprising an amount of CMC2.24 for use in combination with a chemotherapeutic agent in inhibiting the growth of or promoting differentiation of cancer stem cells (CSCs), down-regulating cancer stem cell relevant transcription factors in a cancer stem cell, or the treatment of cancer in a subject afflicted with cancer.

The present invention provides a pharmaceutical composition comprising an amount of CMC2.24 for use in treating cancer in a subject in combination with a chemotherapeutic agent by periodically administering the pharmaceutical composition and the chemotherapeutic agent to the subject.

In some embodiments, a method of treating a patient suffering from cancer comprising administering to the patient the compound in an amount effective to treat the patient.

As used herein, the term "therapeutic agent" refers to any agent used to treat a disease or that provides a beneficial therapeutic effect to a subject.

As used herein, the term "chemotherapeutic agent" refers to any agent used to treat cancer or that provides a beneficial therapeutic effect to a subject suffering from cancer.

Certain embodiments of the method of the present invention provide compositions or compounds containing therapeutic agents such as a cytotoxin, e.g., a cytostatic or cytocidal agent. A cytotoxin or cytotoxic agent includes any agent that is detrimental to cells. Examples include paclitaxel, cytochalasin B, gramicidin D, ethidium bromide, emetine, mitomycin, etoposide, tenoposide, vincristine, vinblastine, coichicin, doxorubicin, daunorubicin, dihydroxy anthracen dione, mitoxantrone, mithramycin, actinomycin D, I-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II), (DDP) cisplatin, anthracyclines (e.g., daunorubicin (formerly daunomycin) and doxorubicin), protein phosphatase inhibitors such as LB100, phosphoNSAIDs, antibiotics (e.g., dactinomycin (formerly actinomycin), bleomycin, mithramycin, and anthramycin), anti-mitotic agents (e.g., vincristine, vinblastine and etoposide), cisplatin and oxaliplatin.

Certain embodiments of the method of the present invention provide compositions or compounds containing chemotherapeutic agents, which are any agents detrimental to cancer cells. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mito-xantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively).

Other chemotherapeutic agents are also within the scope of this invention, including puromycin, 5-fluorocytidine, 2'-deoxy-5-fluorocytidine, 5'-deoxy-5-fluorocytidine, 5'-deoxy-5-fluorocytidine, gemcitabine, cytarabine, cladribine, troxacitabine, abiraterone acetate, abraxane, adriamycin, afinitor, alimta, aloxi, amboclorin, aminolevulinic acid, anastrozole, aprepitant, aromasin, axitinib, azacitidine, bendamustine hydrochloride, bexarotene, bleomycin, bortezomib, cabazitaxel, capecitabine, cerubidine, clofarabine, clofarex, crizotinib, dacarbazine, dasatinib, daunorubicin hydrochloride, decitabine, degarelix, dexrazoxane hydrochloride, docetaxel, doxil, deoxorubicin, ellence, epirubicin hydrochloride, eribulin mesylate, erlotinib hydrochloride, etoposide, evacet, everolimus, fludara, fludarabine phosphate, fluorouracil, fulvestrant, gefitinib, gemcitabine hydrochloride, imatinib mesylate, imiquimod, irinotecan hydrochloride, ixabepilone, lapatinib ditosylate, lenalidomide, letrozole, leucovorin calcium, leuprorelin, levulan, lomustine, lupron, matulane, methotrexate, mitomycin C, navelbine, nelarabine, nexavar, nilotinib, nolvadex, palonosetron hydrochloride, pazopanib hydrochloride, pemetrexed disodium, pralatrexate, prednisone, procarbazine hydrochloride, raloxifene hydrochloride, ruxolitinib phosphate, sorafenib tosylate, sunitinib malate, tamoxifen citrate, taxol, taxotere, temozolomide, temsirolimus, topotecan hydrochloride, toremifene, vandetanib, vemurafenib, vinblastine sulfate, vincristine sulfate, vinorelbine tartrate, vismodegib, wellcovorin, xalkori, zevalin, zinecard, zoledronic acid, paclitaxel, anthracendione, cyclophosphamide, etoposide, LB100, cisplatin, and oxaliplatin. Two or more combined compounds may be used together or sequentially.

The therapeutic or chemotherapeutic agent is not to be construed as limited to classical chemical therapeutic or chemotherapeutic agents. For example, the agent may be a protein or polypeptide possessing a desired biological activity.

As used herein, the term "activity" refers to the activation, production, expression, synthesis, intercellular effect, and/or pathological or aberrant effect of the referenced molecule, either inside and/or outside of a cell. Such molecules include, but are not limited to, cytokines, enzymes, growth factors, pro-growth factors, active growth factors, and pro-enzymes. Molecules such as cytokines, enzymes, growth factors, pro-growth factors, active growth factors, and pro-enzymes may be produced, expressed, or synthesized within a cell where they may exert an effect. Such molecules may also be transported outside of the cell to the extracellular matrix where they may induce an effect on the extracellular matrix or on a neighboring cell. It is understood that activation of inactive cytokines, enzymes and pro-enzymes may occur inside and/or outside of a cell and that both inactive and active forms may be present at any point inside and/or outside of a cell. It is also understood that cells may possess basal levels of such molecules for normal function and that abnormally high or low levels of such active molecules may lead to pathological or aberrant effects that may be corrected by pharmacological intervention.

As used herein, "treating" means reducing, slowing, stopping, or preventing the progression of a disease.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as a substituent on the alkyl group. Examples of alkylheteroaryl moieties include, but are not limited to, —CH$_2$—(C$_5$H$_4$N), —CH$_2$—CH$_2$—(C$_5$H$_4$N) and the like.

The term "heterocycle" or "heterocyclyl" refers to a mono- or polycyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or pluraly. By independently substituted, it is meant that the (two or more) substituents can be the same or different. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, asuitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The term "prodrug" as used herein refers to any compound that when administered to a biological system generates the compound of the invention, as a result of spontaneous chemical reaction(s), enzyme catalyzed chemical reaction(s), photolysis, and/or metabolic chemical reaction(s). A prodrug is thus a covalently modified analog or latent form of a compound of the invention.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

The compounds of the present invention can be synthesized according to methods described in PCT International Publication No. WO 2010/132815 A9. Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Materials and Methods

Before any assays, particular cells were isolated using immunomagnetic and FACS cell sorting, characterized with FACS analysis and cultured under the stemness-promoting conditions (repeated cell sorting; serum-free stem cell medium; Lonza; low cell density; type I collagen-coated surfaces; non-adherent culturing on ultra-low adherent plates; Corning).

Magnetic Cell Sorting (MACS) and Flow Cytometry (FACS)

Dissociated cells were centrifuged at 300 g for 6 min at 4° C., rinsed with sterile MACS buffer (Miltenyi Biotec, CA)

and labeled with CD133 Abs directly or indirectly conjugated with ferromagnetic beads (Miltenyi Biotec, CA) as recommended by manufacturer. For up to 10 min cells, 350 μl MACS buffer, 100 μl of the blocking reagent and 50 μl of the biotinylated CD133 were added, mixed well and incubated 15 min at 4° C. After two times wash with 7 ml MACS buffer cells were incubated for 20 min at 4° C. with 100 μl Anti-Biotin in 400 μl MACS buffer. Washed labeled cells were resuspended in 500 μl of buffer and sorted with MACS devices. Alternatively, cells were sorted with multiparametric flow cytometry with BD FACSAria cell sorter (Becton Dickinson, CA) at sterile conditions. Cells were prepared as described above and labeled with one or several markers conjugated with different fluorescent dyes, such as anti-human CD133/2-APC (clones 293C3; Miltenyi Biotec, CA), CD166-PE (clone 105902; R&D Systems, MN) and CD44-FITC (Biosource, CA). Antibodies were diluted in MACS buffer containing 5% BSA, 1 mM EDTA and 15-20% blocking reagent (Miltenyi Biotec, CA) to inhibit unspecific binding to nontarget cells. After 15-30 min incubation at 4° C., stained cells were washed, resuspended in 500 μl of MACS buffer and sorted.

Generation of Floating Multicellular Spheroids

Four hundred cells of particular phenotype were seeded in each well of the Ultra-Low Attachment (ULA) 6-well plate (Corning, Lowell, Mass.) in serum-free MSCB medium containing 10-25% Matrigel matrix (BD Biosciences) and examined after 1 week of culturing under standard conditions. Fresh medium was added after one week of culturing, every third day.

PCR Array Assay

Stem cell-specific gene expression profiles were studied with the PCR Array assay (SABiosciences, CA) in accordance with the manufacturer's recommendations. Briefly, total RNA was isolated from different cell populations (cancer stem cells expressing high levels of the CD133 and CD44, or whole floating spheroids that are enriched with CSCs) using PARIS kit (Ambion). Up to 1 μg of total RNA was treated with DNase and cDNA was prepared using $RT^2$ First Strand kit. For each analysis, pairs of the test and control cDNA samples were mixed with $RT^2$ qPCR Master mix and distributed across the PCR array 96-well plates, each of which contained 84 stem cell-related probes and control housekeeping genes. After cycling with real-time PCR (Opticon MJ Research or ABI 7300, Applied Biosystems), obtained amplification data (fold-changes in Ct values of all the genes) was analyzed with SABiosciences software.

Western Blot Assay

Cells were lysed using Active Motif Nuclear Co-ip kit according to manufacturer's protocol. 20 μg of enriched nuclear and cytoplasmic extracts was subjected to electrophoresis in 10% polyacrylamide gel. The proteins were then transferred to a nitrocellulose membrane and developed with appropriate antibodies. Mouse monoclonal antibody against Histone H1 (05-457) and GAPDH (MAB374) were purchased from Millipore and mouse monoclonal antibody against p21 was purchased from BD Pharmingen (556431). Rabbit antibody against p53 was purchased from Santa Cruz Biotechnology (sc-6243). Rabbit antibodies against Sox2 (2748), C-Myc (5605) were purchased from Cell Signaling.

Prostate Tissues, Cells and Cultures

Human prostate needle biopsies were taken from otherwise discarded surgical waste in accordance with the SBU IRB and NIH requirements, via a research protocol that was approved by Stony Brook University Committees on Research Involving Human Subjects (CORIHS). Informed written consent was obtained on all participants. The PPT2 prostate adenocarcinoma cell line was established in March 2011 from the stage pT2c pNX pMX prostate cancer patient as a part of routine care for prostate cancer. Needle biopsies were mechanically and enzymatically disaggregated into single cell suspension at sterile conditions, rinsed with Hank's balanced salt solution and incubated for 1.5 hours at 37° C. in serum-free RPMI medium 1640 containing 200 units/ml Collagenases type II and type IV (Sigma-Aldrich), 120 μg/ml penicillin and 100 μg/ml streptomycin. Cells were further disaggregated by pipetting and serial filtration through cell dissociation sieves (size 40 and 80 meshes; Sigma-Aldrich). Single cell suspensions were placed on type-I collagen-coated dishes (Biocoat; Becton Dickenson, Bedford, Mass.) in serum-free Mesenchymal Stem Cell Growth Medium (MSCGM; Lonza) or Stemline Pluripotent Culture Medium (SPCM; Sigma-Aldrich). Fast adherent cells (within the following 15-20 min) were either collected and placed on ultra-low-adherent (ULA) plates or flasks (Corning) to induce floating 3D spheroids, or remained on the type I collagen-coated dishes for further propagation. Penicillin, streptomycin and TrypLE were obtained from Invitrogen (Grand Island, N.Y., USA). The MSCGM and SPCM were changed twice weekly. All experiments were performed on primary prostate cancer patient-derived PPT2 cells and for comparison, on the established highly metastatic derivative of the androgen-independent PC-3 cell line, PC3MM2, originally purchased from the M. D. Andersen Cancer Center, TX.

Isolation, Purification and Characterization of the Tumor-Initiating Cells

To ensure more reliable isolation of CSCs, cells were labeled with one or several markers conjugated with different fluorescent dyes, including anti-human CD133/2-APC (clone 293C3; Miltenyi Biotec, CA, USA); CD166-PE (clone 105902; R&D Systems, MN, USA); CD44-FITC (clone F10-44-2), CD44-PE (clone F10-44-2; Invitrogen/Biosources, USA); CD44v6-FITC (clone 2F10; R&D Systems, USA), EpCAM-FITC (Biosource, CA, USA), Pan-Keratin (C11)-Alexa Fluor® 488 (Cell Signaling) and all the isotype controls (Chemicon). Antibodies were diluted in buffer containing 5% BSA, 1 mM EDTA and 15-20% blocking reagent (Miltenyi Biotec) to inhibit unspecific binding to non-target cells. After 15 min incubation at 4° C., stained cells were sorted and analyzed with multiparametric flow cytometer BD FACSAria (Becton Dickinson, CA). Alternatively, dissociated cells were centrifuged at 950 g for 5 min at 4° C., rinsed with sterile MACS buffer (Miltenyi Biotec, CA) and labeled with CD133 Abs directly or indirectly conjugated with ferromagnetic beads (Miltenyi Biotec, CA) as recommended by manufacturer.

Sphere Formation Assay

In order to obtain prostate cancer spheroids, MACS-CD133 and MACS-CD44 (Miltenyi Biotec, CA) or FACS sorted $CD133^{high}/CD44^{high}$ cells were seeded at low numbers on ULA plates (1,000 cells per 6-well plate or 5-10,000 cells per 75 mm flasks) in MSCGM or SPCM. For evaluation of the clonogenic/sphere-forming capacity, cells were counted with Cellometer Auto T4 (Nexcelom Bioscience LLC, MA), resuspended in 1:4 type I collagen/SPCM or 1:4 Matrigel/MSGM and known cell numbers were plated on ULA plates. One week after initiation plates were inspected for floating sphere growth and compact well-shaped spheroids were counted. Spheroids were serially passaged by gentle dissociation and mixing with a new Matrigel/MSGM or type I collagen/SPCM, or reseeded on 48-well plates for final count of 5-10 spheres per well for further propagation and analysis.

Mice Tumor Xenografts

All experiments involving the use of animals were carried out in strict accordance with the recommendations in the Guide for the Care and Use of Laboratory Animals of the National Institutes of Health, via a research protocol that was approved by Stony Brook University Institutional Animal Care and Use Committee (IACUC). NOD/SCID mice (Charles River Laboratories International, Inc., MA) were maintained under defined conditions at SBU animal facility. After sufficient propagation, CD133$^+$ cells were resuspended in 1:1 MSCGM/Matrigel and injected to the flanks of 6 weeks old NOD/SCID mice (3,000 cells per mice; subcutaneously). Tumor development was monitored starting from the second week. The primary tumor sizes were measured with a caliper on a weekly basis and approximate tumor weights determined using the formula $0.5ab^2$, where b is the smaller of the two perpendicular diameters. All mice were terminated after fourth week of treatment, if the tumor measured ~2 cm, or at the first sign of suffering.

Ability to induce the round colonies (holoclones) was also determined before and after drug treatment. Cells were counted and plated on 48-well plates at a final count of 300 cells per well. One week after initiation, the plates were inspected for colony growth and the number of colonies within each well was quantified by phase contrast microscopy. After drug treatment, one portion of cells which survived particular treatment regimen was placed at 3D and adherent culture conditions and analyzed. Another portion was used for analysis of the drug-induced alterations in expression of the stem cell markers with PCR array assay, western blotting and FACS.

Ability to induce the round colonies (holoclones) was also determined before and after drug treatment. Cells were counted and plated on 48-well plates at a final count of 300 cells per well. One week after initiation, the plates were inspected for colony growth and the number of colonies within each well was quantified by phase contrast microscopy. After drug treatment, one portion of cells which survived particular treatment regimen was placed at 3D and adherent culture conditions and analyzed. Another portion was used for analysis of the drug-induced alterations in expression of the stem cell markers with PCR array assay, western blotting and FACS.

Drugs

Paclitaxel (Ptx; Taxol) was provided by Indena (Milan, Italy). New-generation taxoid, SB-T-1214 was synthesized by Dr. Ojima's group (Stony Brook University, ICB&DD, NY, USA). Chemically modified curcumin, CMC-2.24 was synthesized by Dr. Johnson's group (ChemMaster International, Inc., Stony Brook, N.Y., USA). DMSO and MTT were purchased from Fisher Scientific (Pittsburgh, Pa., USA).

In Vivo Cytotoxicity of SBT-1214

Animals were handled according to protocols that have been approved by the Institutional Animal Care and Use committee of the Stony Brook University. The staff of veterinarians provided veterinary care. The SBT-1214 was administered intravenously (40, 20, 20, 20 mg/kg; weekly) to 6-weeks old NOD/SCID mice. Treatment was started 2-3 weeks after transplantation of the tumor cells, when tumor xenografts reached ~100 mm$^3$. Systemic toxicity in NOD/SCID mice was closely monitored and evaluated by standard criteria (motor activity, morbidity, appetite, posture and appearance). One week after the last treatment, all residual tumors were harvested and analyzed histopathologically and for ex vivo clonogenic capacity. One part of each mouse tumor xenograft was snap-frozen in embedding matrix (Lipshaw) and kept at −80° C. before immunohistochemical analysis at standard conditions. Another portion of each harvested tumor was mechanically and enzymatically disaggregated into single cell suspension as previously described (Hermann, P. C. 2007). Ability to induce the round colonies (holoclones) was also determined before and after drug treatment. Cells were counted and plated on 48-well plates at a final count of 300 cells per well. One week after initiation, the plates were inspected for colony growth and the number of colonies within each well was quantified by phase contrast microscopy. After drug treatment, one portion of cells which survived particular treatment regimen was placed at 3D and adherent culture conditions and analyzed. Another portion was used for analysis of the drug-induced alterations in expression of the stem cell markers with PCR array assay, western blotting and FACS.

In Vitro Cytotoxicity

The CSC-specific cytotoxic effects were studied in two different settings both of which are known to maintain/promote sternness phenotype: adherent to type I collagen cultures and 3D cultures of floating spheroids (Baretton, G. B. 1994; Miyoshi, Y. 2000; Koivisto, P. 1995). The CD133$^{high}$/CD44$^{high}$ cells ($1 \times 10^3$ cells/well) isolated either from PPT2 or PC3MM2 cell lines were seeded onto the type I collagen-coated 96-well plates, cultured in the MSCGM for 2 days, and the treatment was initiated upon 90% confluency. Paclitaxel, SBT-1214 and CMC2.24 were dissolved in sterile DMSO and then serially diluted in MSCGM. For testing the SBT-1214/CMC2.24 combination efficacy, the regular MSCGM was replaced with treatment medium containing SBT-1214 or Ptx at selected concentration range (from 10 nM to 10 μM) with 30 μM CMC2.24. Treatment medium was removed 24, 48 or 72 hr later, followed by return to the MSCGM. Cell death was analyzed on adherent type I collagen cell cultures with the MTT assay [MTT=3-(4,5-dimethylthiazol-2-yl)-2,5-diphenyltetrazolium bromide] as recommended by manufacturer (Invitrogen). Spheroids were cultured and treated on ULA plates.

Statistical Analysis

The dose-response cytotoxicity of SBT-1214, CMC2.24/ and their combination was evaluated by standard MTT assay (all of the in vitro experiments were repeated at least three times and each measurement for the MMT assay was performed in 4 repeats). The dose-response points were plotted as a percentage of the untreated control, the absorbance of which was considered as 100%. Data were expressed as means±SD for each drug concentration. The in vivo responses to drug treatment were evaluated as changes in tumor volume of drug-treated versus untreated control xenografts induced by particular type of cells. Data were expressed as means±SD for control and drug treated tumors. The statistical significance of differences was determined using Student's t-test. The parameters used were the two-tailed distribution and the paired test. P<0.05 was considered statistically significant.

Example 1. TF Expression Profiling for Human Prostate and Colon CSCs

A discrete subpopulation of highly tumorigenic cells that, according to current criteria of sternness and our functional genomics and proteomics studies, are cancer stem cells (CMCs) that have been identified and characterized (Rowehl et al, 2008; Botchkina et al, 2009; 2010; Botchkina & Ojima, 2011). In such cells isolated either from primary prostate and colon tumors or from highly metastatic cancer cell lines, overexpression of a large number of stemness-related genes and transcription factors (TFs) involved in stem-cell (SC) regulation and functioning, cancer development, metastasis and drug resistance, have been found (FIG. 2).

In particular, genome-wide and pathway-specific studies have demonstrated that such cells possess many other stem-cell characteristics, in particular, over-activated tumorigenic and developmental cascades, such as Hedgehog, EGFR, Wnt/β-catenin and Notch linked with the stem cell regulation and metastasis. Many genes responsible for SC self-renewal (C-Myc, SOX1, SOX2, MYST1, MYST2, NEUROG2, HSPA9), regulation of symmetrical cell division (NOTCH1, NOTCH2, PARD6A), as well as those related to prostate stem cell regulation (HhF and TGFβ) and high resistance to drugs were significantly up-regulated in CSC-enriched cell populations compared to the bulk counterparts.

The PCR Array data showed that the metastatic colon cancer and prostate cancer patient-derived CD133$^{hi}$ cells and 3D spheroids induced by such cells over-expressed a majority of the 84 studied stem cell-related genes and 84 studied stem-cell-related TFs (FIG. 2 shows this data for both prostate and colon cancers). Thus, the most up-regulated genes in CSCs versus differentiated prostate cancer cells (41 of 84=45% genes) includes CDX2, DLX2, DNMT3B, EGR, 3EZH2, FOXP3, GLI2, HOXA1O, HOXA11, HOXA2, HOXA3, HOXA7, HOXB3, HOXB8, HOXB5, HOXC1O, HOXC9, HOXC6, HOXC4, HOXC5, IRX4, ISL1, JUN, KLF2, NFATC1, NKX2-2, NR2F2, PAX9, PCNA, PITX2, PITX3, POU4F1, POU5F1, RUNX1, SIX2, SOX2, SOX9, TERT, VDR, WRN, WT1.

The large representation of the over-expressed HOX TF family (FIG. 2C), which have a potent anti-apoptotic function among others, can explain the high drug resistance of the CD133$^{hi}$/CD44$^{hi}$ cells. In addition, common markers of stemness (CD133, CD44, ALDH1), and FGF1 and FGF3 were also up-regulated. These changes are associated with activation of STAT TF family, resistance to treatment, enhanced proliferation, resistance to cell death, increased invasiveness and metastasis (rev. Kwabi-Addo et al, 2004). Among the up-regulated genes were several key TFs responsible for self-renewal and induction of pluripotency, including c-Myc, Sox-2, Oct-4 and Nanog, which was confirmed with FACS and western blot analyses.

In addition, the CD133$^{hi}$/CD44$^{hi}$ cells cultured under sternness-promoting conditions (as 3D spheroids or adherent to type I collagen in serum-free stem cell medium) over-expressed many anti-apoptotic and drug resistance-related genes, and showed profoundly low sensitivity to taxol, paclitaxel, 5FU and other standard anti-cancer drugs. Importantly, not only the ratio but the actual number of such cells significantly increases after drug administration. Thus, treatment with taxol increased the number of CD133$^{hi}$ cells to 160% in type I collagen cultures, and to 149% in 3D spheroids, whereas only CD133-negative cells were partially killed by the drug (FIG. 1).

It has been demonstrated that prostate and colon cancer cells that have the CD 133$^{hi}$/CD44$^{hi}$ phenotype, represent a CSC-enriched population of highly tumorigenic and highly drug-resistant cells, which expressed large number of TFs involved in stem-cell regulation and functioning, cancer development and progression, drug resistance and metastasis. Therefore, both CSCs and CSC-relevant TFs represent a critically important and logical target for therapeutic intervention, because abrogation of the key cell-signaling pathways that are over-represented in the CSC population should lead to disruption of self-renewal and consequently tumor regression.

Example 2. CMC2.24 Down-Regulates CSC Relevant TFs

Figure 3A:
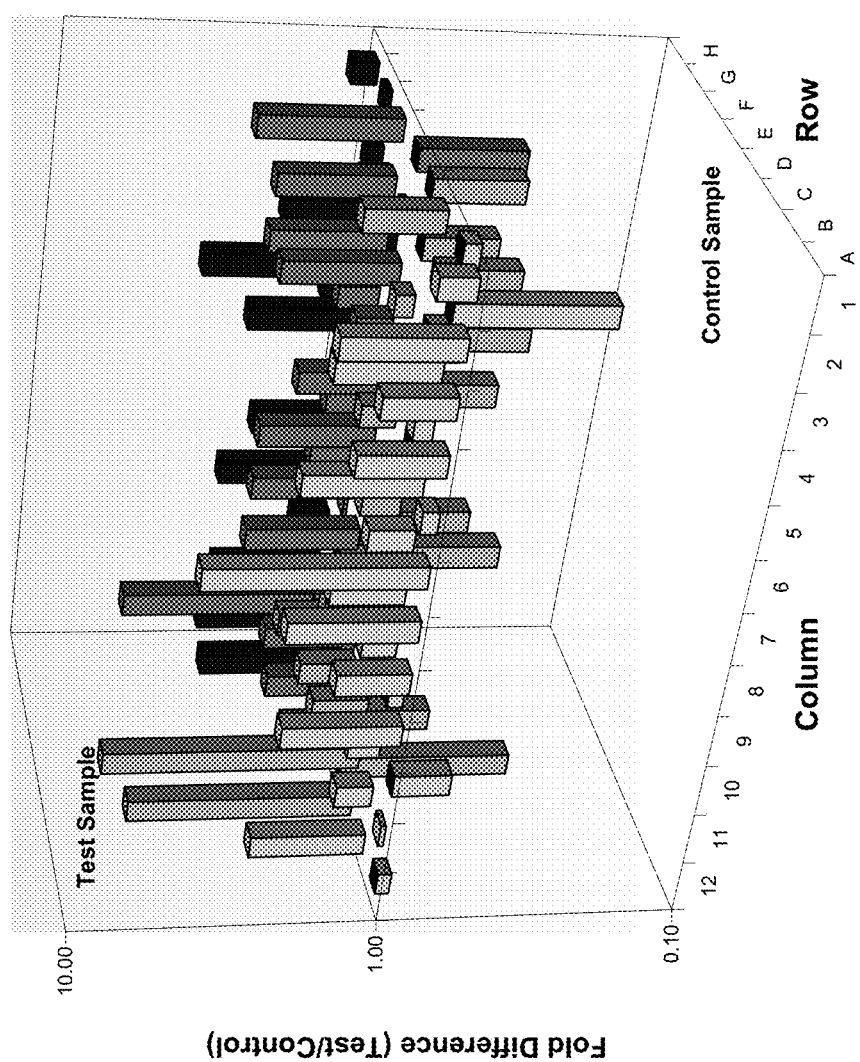
FIG. 3A: PCR Array of Stem Cell-Related Transcription Factors (TFs). Colon Cancer HCT116 CD133+ cells. Untreated Control (CSCs CD133$^+$ vs. differentiated) (SABiosciences; PAHS-501).
Figure 3B:
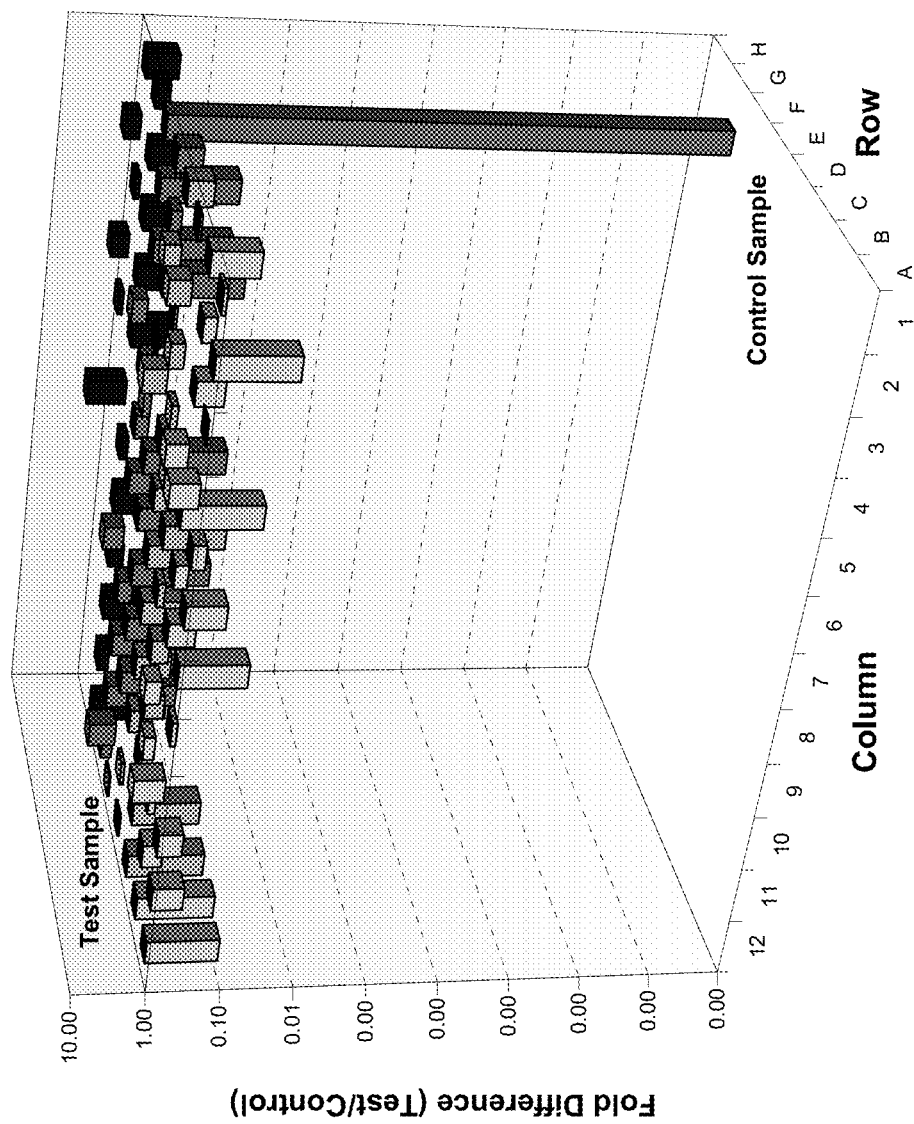
FIG. 3B: PCR Array of Stem Cell-Related TFs. Colon cancer HCT116 CD133$^+$ cells. Treated (Combination of CMC2.24 (5 μM)/SB-1214 (1 μM) vs. untreated) (SABiosciences; PAHS-501). Post-treatment down-regulation of the over-represented colon, sternness-relevant, transcription-relevant, transcription factors after administration of CMC2.24 (5 μM)/SB-1214 (1 μM)/combination for 24 hrs.

CMC2.24 induces profound inhibition of the majority of CSC-relevant transcription factors in highly aggressive colon cancer HCT116 CD133+ and prostate xPT2 CD133+ cells. Importantly, majority of the overactivated TFs were suppressed, including CDX2, DLX2, EGR3, FOXP3, GLI2, HOXA2, HOXA7, HOXB3, HOXB8, HOXC1O, HOXC9, HOXC6, HOXC4, HOXC5, IRX4, JUN, KLF2, NFATC1, NR2F2, PITX3, POU5F1, RUNX1 and WT1 (FIG. 3).

Effects of CMC2.24 on several key TFs were tested with the western blot assay, which has confirmed PCR array data, showing dramatic inhibition of these proteins in both nuclear and cytoplasmic fractions (FIG. 5).

Example 3. CMC2.24 in Combination with SBT1-1214 Down-Regulates CSC Relevant TFs FIGS. 3 and 4 demonstrate that CMC2.24 in combination with other anti-cancer drugs, such as the new generation taxoid, SBT-1214 (FIG. 6), can induce profound inhibition of the majority of CSC-relevant transcription factors in colon cancer HCT116 CD133+ and prostate xPT2 CD133+ cells. Importantly, 56% of the overactivated TFs were suppressed, including CDX2, DLX2, EGR3, FOXP3, GLI2, HOXA2, HOXA7, HOXB3, HOXB8, HOXC1O, HOXC9, HOXC6, HOXC4, HOXC5, IRX4, JUN, KLF2, NFATC1, NR2F2, PITX3, POU5F1, RUNX1 and WT1.

It was determined that SBT-1214/CMC2.24 combination induces profound inhibition of the CSC-enriched prostate and colon cancer cell populations, including highly tumorigenic and clonogenic patient-derived CSCs. Although shortly after drugs removal we have observed enrichment of the large multinucleated cells-treatment survivors, these drug resistant cells became quiescent, expressed multiple morphological abnormalities and died during the succeeding 1-2 weeks of culture follow-up. Importantly, post-treatment cell-survivors lost their ability to form 3D cancer spheroids, which is one of the major functional criteria of stemness.

Effects of CMC2.24 in combination with SBT-1214 on several key TFs were tested with the western blot assay, which has confirmed PCR array data, showing dramatic inhibition of these proteins in nuclear fraction of both CSCs and their differentiated counterparts (FIG. 5).

Thorough molecular analyses of such cell-treatment survivors revealed that majority of the CSC-relevant genes and transcription factors were significantly down-regulated (FIGS. 2-4). Among them were several key TFs responsible for self-renewal and pluripotency induction, including c-Myc, Sox-2, Oct-4 and Nanog, which was confirmed with FACS and western blotting. The large representation of the over-expressed HOX TF family, which have a potent anti-apoptotic function among others, can explain the high drug resistance of the CSCs. Therefore the significant inhibition of their expression is very promising.

The synergistic action of these tissue-specific transcription factors is a pivotal mechanism for determining cellular phenotypes and self-renewal of embryonic stem cells. Thus, the introduction of four genes (Oct-3/4, SOX2, cMyc, and Klf4) into adult fibroblasts can transform them into pluripotent stem cells. Expression of Oct3/4 and Sox2 has also been associated with an unfavorable clinical outcome.

Therefore, significantly decreased levels of expression of stem cell-related genes in general, and shut-down of several major players, including Oct-4, Sox-2, c-Myc and Lin-28 after treatment with SBT-1214/CMC2.24 combination is promising, because most likely it means that treated CSCs were promoted to the more differentiated state.

As mentioned hereinabove, this data is important in the light of growing evidence which indicates that standard anti-cancer therapies promote self-renewal of tumor-initiating cells and further increased resistance to treatment.

Importantly, it was found that simultaneously with the inhibition of the key pluripotency transcription factors and other sternness- and drug resistance-related genes, the SBT 1214/CMC2.24 combination induced the previously lacking expression of the pro-apoptotic proteins p53 and its regulator, p21. In other words, this drug combination exerted p53 and p21 "gene arousal" activities, which means that this treatment modality can also induce sensitivity of CSCs to other drugs.

Example 4. Establishment and Characterization of the Spontaneously Immortalized Primary Prostate Cancer Cell Line, PPT2

Dissociated cells of needle biopsies from 22 resected prostate carcinomas of various histological grades were tested for clonogenic and tumorigenic potential in vivo and in vitro as described in the Methods section. Twenty specimens contained a subpopulation of the fast-adherent cells (FA) to the type I collagen, which initially proliferated in serum-free stem cell medium. Fourteen of the 22 specimens induced floating multicellular aggregates, and only three specimens were able to induce dense 3D spheroids characteristic of CSCs. However, the majority of the primary cells lost their clonogenic and sphere-forming capacities after several passages, which is in line with numerous observations that primary prostate cancer cells have a finite lifespan (5-6 passages) (Peehl, D. M. 2004). In contrast, tumor cells isolated from the patient with stage pT2c pNX pMX PrC were spontaneously immortalized and continued long-term in vitro and in vivo growth (>28 passages, currently). With serial rounds of transplantation and passaging in a stem cell medium, three different cell populations became evident: the major population of elongated cells, numerous round holoclones containing small cells, and rare, very large multinuclear cells (which we often observe in several established and primary prostate and colon cancer cell lines). Subcloning of these small-cell-containing holoclones led to dramatic enrichment of cells expressing high levels of CD133, CD44, CD44v6, EpCAM, CD49f and CD166 (FIG. 1A). This cell line (called PPT2) was serially propagated as NOD/SCID mice tumor xenografts, floating 3D spheroids and type I collagen-adherent cultures. According to the ATCC report (ID number 002872), the PPT2 cells are unique human cells with no match to any profile in the ATCC STR database, which means that they are not contaminated with any known established cell lines.

Figure 7A:
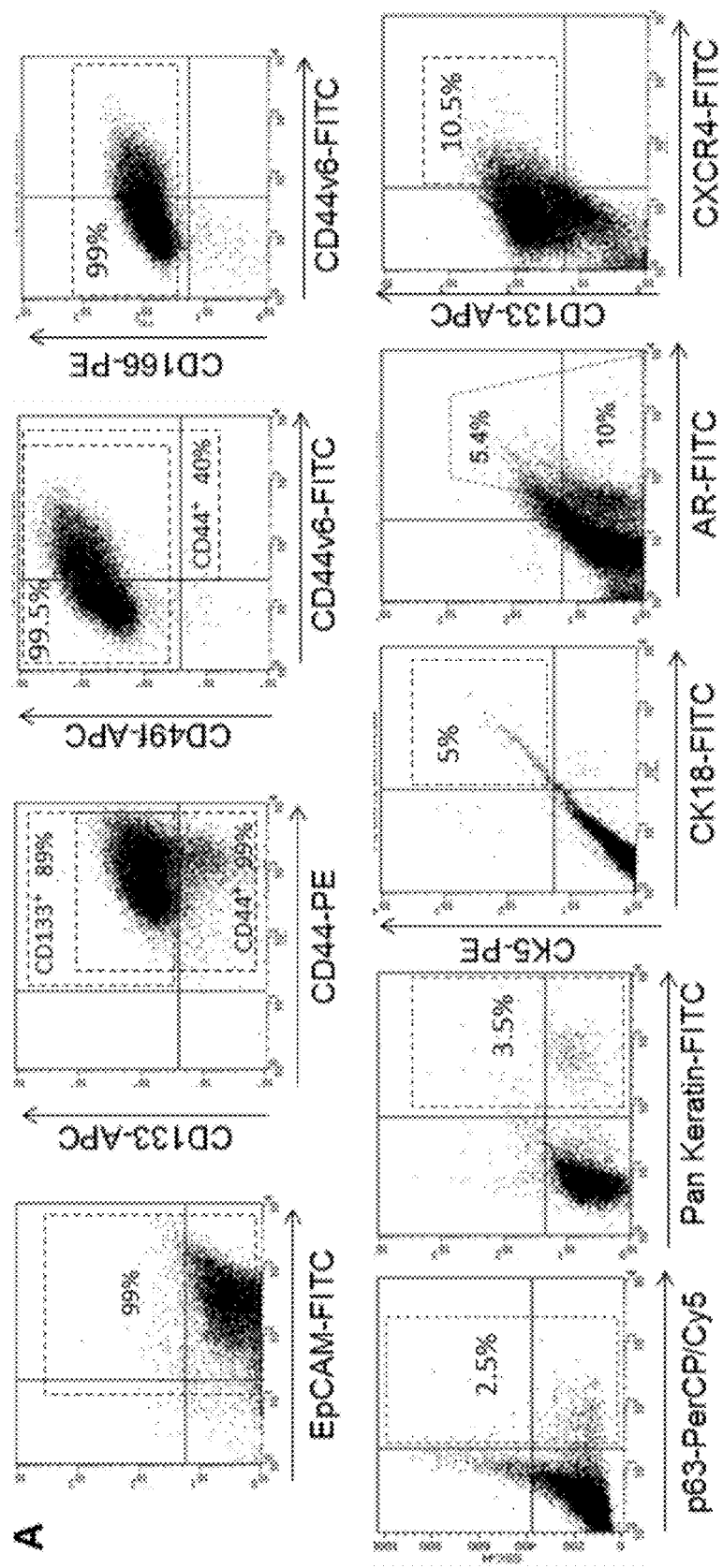
FIG. 7A: Molecular characterization of the primary prostate PPT2 cell line. Representative FACS analyses of the different cell surface markers expression in unsorted PPT2 cells grown for 4 weeks on type I collagen in MSGB medium. Each dotted square represents the population of cells expressing moderate/high levels of a particular marker conjugated with different fluorescent tags. Note a long-term retention of the CD133-APC, standard (CD44-PE) and variant (CD44v6-FITC) CD44 and CD49f-APC. In contrast, only small fractions of the PPT2 cells expressed a marker of basal cells, p63, a marker of differentiated cells, pan-keratin, CK18, AR and CXCR4.

Although phenotype of the CSC-enriched cultures is dynamic due to the dual nature of the CSCs (i.e., ability to self-renew and to generate committed progenitors), the PPT2 cells retain relatively stable phenotypes even up to 8 weeks after the last MACS-CD133$^+$ cell sorting and culturing on type I collagen-coated surfaces in serum-free Mesenchymal Stem Cell Growth medium, MSCGM (Lonza; FIG. 7 and Table 1). Thus, virtually the entire population of PPT2 cells was undifferentiated (only 3-5% expressed marker of differentiated cells, pan-keratin), positive for EpCAM, CD49f, standard isoform of the CD44 (98-99%; clone MEM-85; Invitrogen), and up to 72% express variant isoform, CD44v6 (clone 2F10; R&D). After >27 passages, about 90% of PPT2 cells still express moderate-to-high levels of CD133 and possess very high sphere-forming capacity in 3D culture containing 1:4 collagen type I/Stem-line Pluripotent Culture Medium (SPCM; Sigma-Aldrich). Twelve-sixteen percent of the PPT2 cells were positive for androgen receptor (AR$^+$), and 8-10% were positive for CXCR4 (FIG. 7A). In contrast to the original tumor tissue, purified CD133$^+$ cells did not express PSA, which appeared again in the NOD/SCID mice tumors after transplantation of the CD133$^+$ cells (FIG. 7B). The vast majority of the CD133+ PPT2 cells expressed high cytoplasmic levels of vimentin and nestin, characteristic of neural and embryonic stem cells. The expression of these two markers was highest in gigantic multinucleated cells (MNCs; FIG. 7C). Both nuclear and cytoplasmic fractions of the PPT2 cells expressed c-Myc, whereas other pluripotency markers (Oct-4 and Sox-2) were detected only in nuclear fraction (FIG. 7D). Importantly, PPT2 cells were negative for pro-apoptotic/tumor suppressor proteins, p53 and p21, and extremely resistant to standard anti-cancer drugs. By present time, after about 2.5 year of maintenance, the vast majority of the PPT2 cells remains at an immature state, continues to express high ratios and high levels of commonly used sternness and pluripotency markers mentioned above and retains very high tumor-initiating, clonogenic and sphere-forming capacities during serial transplantations of the relatively low cell numbers. All of the above motivated our team to test the two proprietary drugs, SBT-1214 and CMC2.24 against this highly drug resistant, CSC-enriched primary prostate cancer cell line and for comparison, against established a highly metastatic derivative of the PC-3 cell line, PC3MM2 cells, which were characterized in our previous study (Rowehl, R. H. 2008).

TABLE 1

Phenotypic profiling of the PPT2 and PC3MM2 cells with FACS analysis*

| Marker | Source | PPT2 cells** Levels of expression | PPT2 cells** % of total cell # | PC3MM2 cells*** Levels of expression | PC3MM2 cells*** % of total cell # |
|---|---|---|---|---|---|
| CD133 | Miltenyi Bio | +++ | 75 ± 15 | ++/+++ | 3 ± 1 |
| CD44 | Invitrogen Clone# MEM-85 | +++ | 99.5 ± 0.5 | ++/+++ | 7.5 ± 2.5 |
| CD44v6 | R&D Clone# 2F10 | +++ | 56 ± 16 | | |
| CD49f | BioLegends | +++ | 99.5 ± 0.5 | +++ | 94 ± 2 |
| CD166 | BD Biosci. | +++ | 99.3 ± 0.5 | ++/+++ | 86 ± 8 |
| EpCAM | Miltenyi Bio | +++ | 98 ± 0.5 | ++/+++ | 83 ± 5 |
| Pan-Kerat | Cell Signal. | ++ | 4 ± 1 | | |
| CK5 | Santa Cruz | + | 7 ± 1 | + | 3 ± 1 |
| CK18 | Santa Cruz | + | 5.5 ± 2.5 | + | 3.5 ± 0.5 |
| CK5/CK18 | | + | 4.5 ± 0.5 | + | 2.5 ± 0.5 |
| p63 | Santa Cruz | + | 5 ± 2.5 | + | 7 ± 1 |
| AR | Santa Cruz | + | 14 ± 2 | ++/+++ | 5 ± 2 |
| CXCR4 | R&D | ++ | 10.5 ± 1 | +++ | 12 ± 2 |

*Mean percentage of cells expressing particular cell surface marker was calculated based on the three independent FACS analyses.
**PPT2 cells (unsorted before analysis, but established by previous repeated MACS-CD133$^+$ cell sorting) were cultured on type I collagen-coated dishes in MSCB medium for 2, 4 and 8 weeks.
***Unsorted PC3MM2 cells were cultured on type I collagen-coated dishes in MSCB medium for 1-2 weeks.
+, ++ and +++ represents low, moderate and high expression.

Figure 8A:
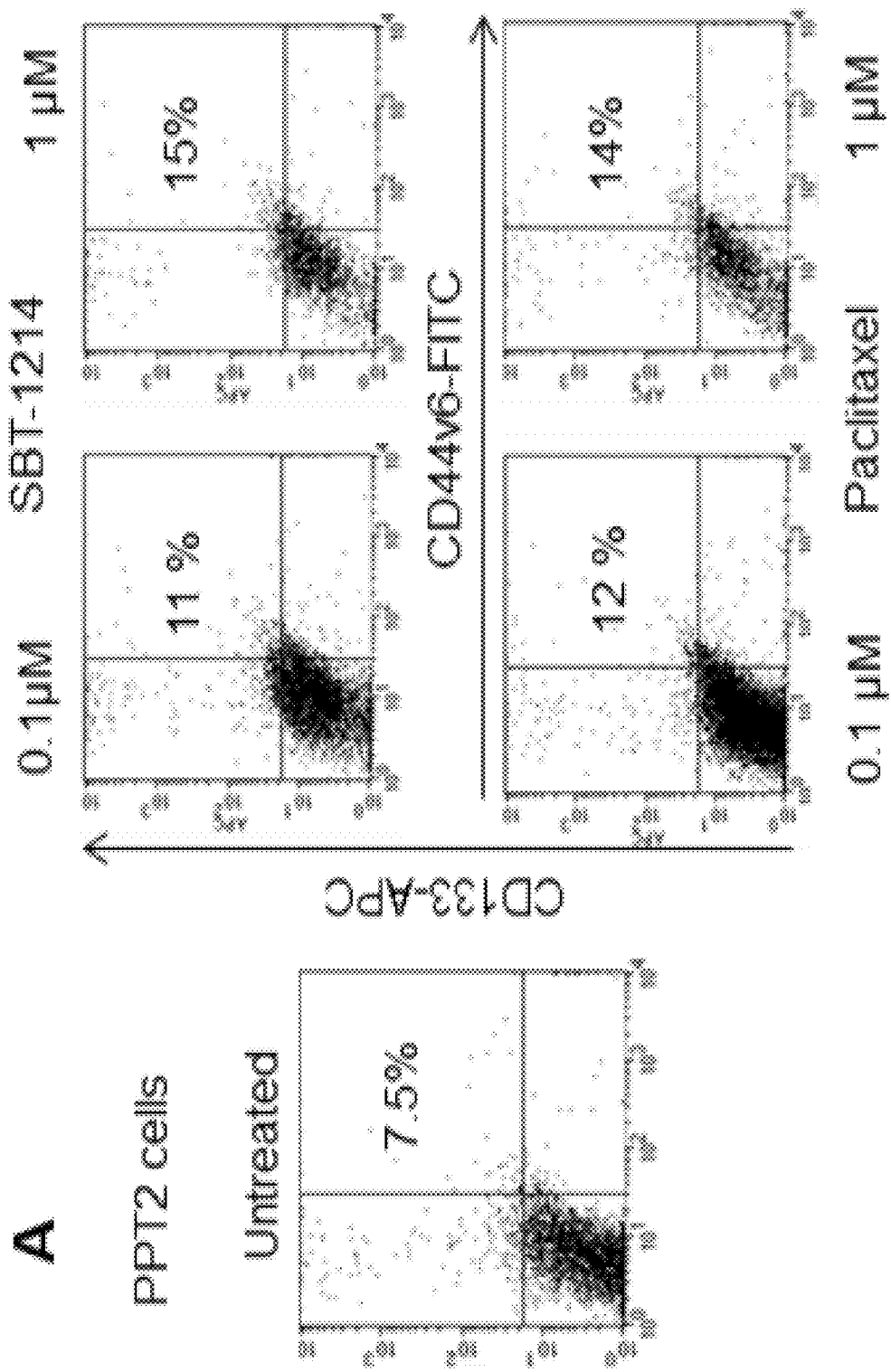
FIG. 8A: In vitro cytotoxicity of SBT-1214 and paclitaxel against prostate CSC-enriched cell populations. Representative FACS analysis shows a dose-dependent increase in the ratios of CD133$^{high}$ PPT2 (A) cells 24 hours after treatment with SBT-1214 and Ptx.
Figure 8B:
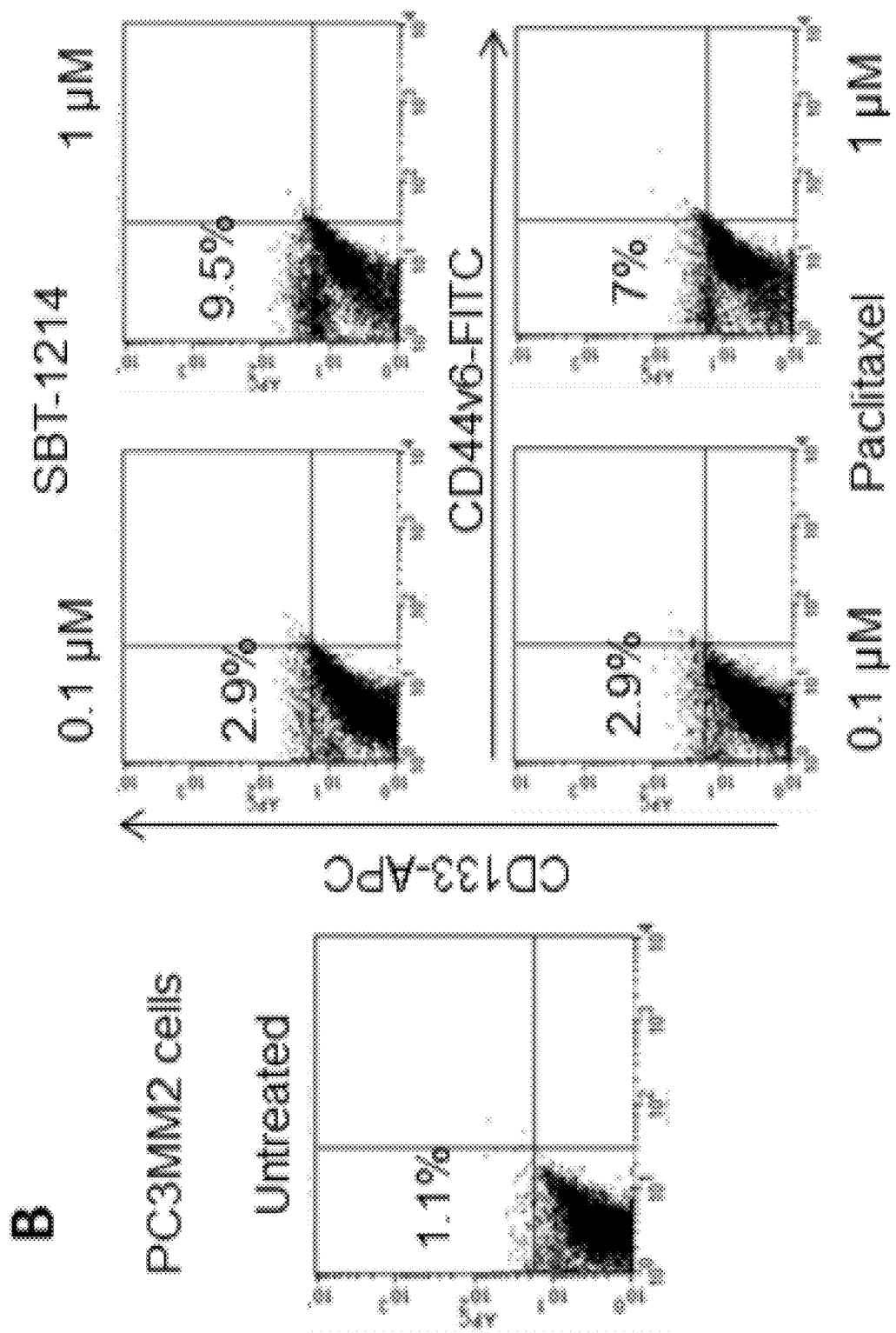
FIG. 8B: In vitro cytotoxicity of SBT-1214 and paclitaxel against prostate CSC-enriched cell populations. Representative FACS analysis shows a dose-dependent increase in the ratios of PC3MM2 (B) cells 24 hours after treatment with SBT-1214 and Ptx.
Figure 8C:
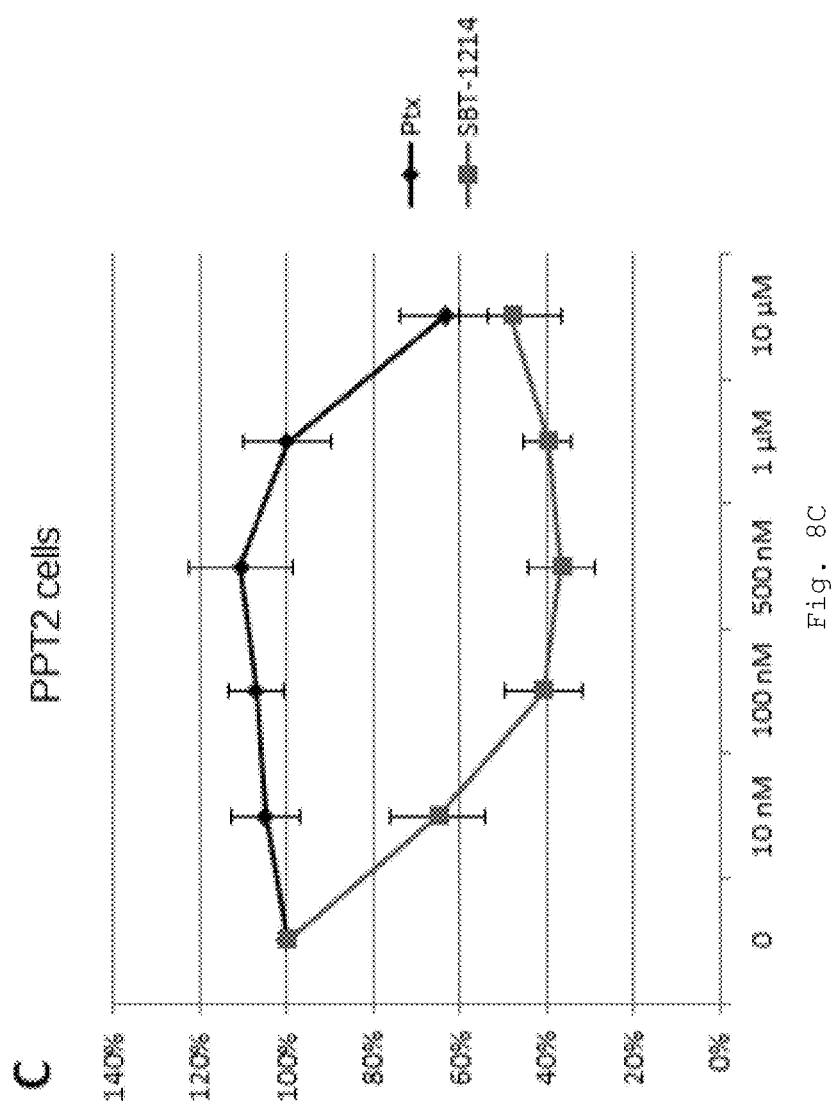
FIG. 8C: Longer treatment (for 72 hours) with SBT-1214 (10 nM-10 μM) induced up to 65% cell death in PPT2 cells. In contrast, treatment with the same doses of Ptx did not suppress proliferation of the tumorigenic prostate cancer cells (upper line). Cells were incubated with indicated drug concentrations, and data was obtained with standard MMT assay based on three independent experiments with four repeats in each treatment group. Values are the means±SD.
Figure 8D:
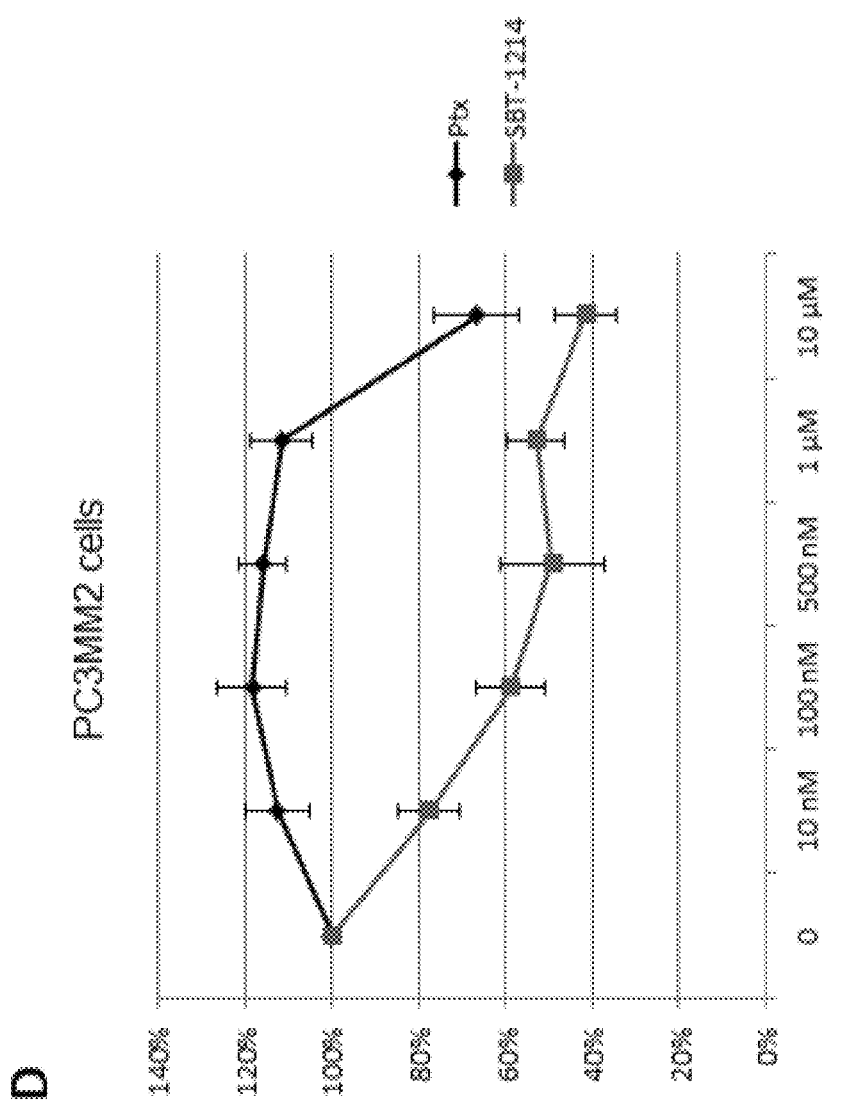
FIG. 8D: Longer treatment (for 72 hours) with SBT-1214 (10 nM-10 μM) induced up to 60% in PC3MM2 cells (D; lower line). In contrast, treatment with the same doses of Ptx did not suppress proliferation of the tumorigenic prostate cancer cells (upper line). Cells were incubated with indicated drug concentrations, and data was obtained with standard MMT assay based on three independent experiments with four repeats in each treatment group. Values are the means±SD.

Example 5. Cytotoxic Effects of SBT-1214 Against CSC-Enriched Prostate Cancer Cells In Vitro Treatment with SBT-1214 and, for comparison, with the commonly used microtubule stabilizing agent paclitaxel (Ptx; Taxol) increased the ratios of cells with highest expression of CD133 in a concentration-dependent manner (from 10 nM to 10 µM; for 24 hours) in both PPT2 and PC3MM2 cell lines (representative FACS is shown on FIG. 8A-B). This data suggests that both drugs preferentially affected cells with low CD133 expression, and initially did not affect or even stimulate proliferation of the CD133$^{high}$ cells. However, a longer treatment (for 48-72 hours) revealed a profound difference between the cytotoxic effects of SBT-1214 and Ptx: while Ptx-treated cells retained viability and the number of viable cells was still increased, up to 60% of the SBT-1214-treated CD133$^+$ cells were killed with the same concentrations of the drug (the MTT assay data are shown on FIG. 8C-D; FIG. 9A). Surprisingly, lower concentrations of SBT-1214 (100 nM-1 µM) induced higher cytotoxicity in PPT2 cells compared to 10 µM drug concentration. Paclitaxel at 10 µM was cytotoxic and induced about 40% cell death (FIG. 8C-D). At this time point, an increased ratio of very large MNCs (often ≥200 µm) was obvious in both PPT2 and PC3MM2 cells (FIG. 9A-B). To test whether or not treatment with SBT-1214 affects the clonogenic potential of the CD133$^+$ cells, PPT2 and PC3MM2 floating spheroids were treated with 1 µM of the drug for 24 hours in order to induce alterations, but avoid profound cell death. We have found that in contrast to control untreated spheroids, SBT-1214 treated cells lost their ability to induce both secondary 3D spheroids (FIG. 9C) or collagen-adherent colonies. Both PPT2 and PC3MM2 cells-treatment-survivors exerted profound cell death at 2-5 days post-treatment with SBT-1214 (FIG. 9D).

Example 6. In Vivo Efficacy of SBT-1214 Against Prostate Tumor Xenografts Induced by CD133$^+$ Cell Populations After transplantation of the CD133$^+$ PPT2 and PC3MM2 cells, NOD/SCID mice were randomly divided into 3 groups for each cell type: one as an untreated control (n=4), a second group for SBT-1214 treatment with 40, 40, 40 mg/kg weekly regimen (n=4), and a third group for treatment with 40, 20, 20, 20 mg/kg weekly regimen (n=6). Treatment was started 2-3 weeks after transplantation of the tumor cells, when tumor xenografts reached >100 mm$^3$; tumor development was monitored weekly. Although all four tumors treated with 40, 40, 40 mg/kg weekly regimen had dramatically shrunk by the third treatment, all mice expressed common signs of systemic toxicity and were euthanized (data are not shown). The treatment with 40, 20, 20, 20 mg/kg weekly regimen induced more significant tumor regression (FIG. 10A-D), with much lower systemic toxicity. One week after the last treatment, all residual tumors were harvested and analyzed histopathologically and for ex vivo clonogenic capacity. Untreated control tumors were removed upon reaching ~2 cm in largest diameter in accordance with the IRB requirements.

By histopathological analysis, the hematoxylin and eosin stained tissue sections of the control untreated patient-derived CD133$^+$ cell-induced NOD/SCID mice tumor xenografts showed highly atypical epithelial cells forming nests and gland-like structures, consistent with poorly differentiated adenocarcinoma (FIG. 10E). Numerous atypical mitotic figures and central necrosis were usually present. The two larger PPT2-induced SBT-1214-treated residual tumors were also diagnostic of poorly differentiated adenocarcinoma, but possessed a greater degree of nuclear atypia, and only few mitotic figures. In addition, the SB-1214-treated tumor showed focal hyalinization but no evidence of necrosis. Smaller residual tumors (n=4) showed a higher level of hyalinization and a lack of viable cells.

Total cell suspensions from the control and SBT-1214-treated residual tumors were seeded on type I collagen-coated dishes and ULA plates to test for the presence of CSCs and their ability to induce secondary spheroids or adherent cell colonies. Four of six PPT2-induced and three of six PC3MM2-induced SBT-1214 treated residual tumors were composed of tan or dark red masses which did not show the presence of viable cells, and did not produce either adherent or floating colonies in culture. Two of the PPT2-induced post-treated residual tumors and three of the PC3MM2-induced tumors contained viable slowly proliferating cells. The two PPT2 residual tumors also showed clusters of gigantic multinucleated cells-treatment-survivors (arrows on FIG. 10F) similar to those commonly observed after treatment of the CSC-enriched populations with chemotherapeutic agents in vitro (FIG. 9B). However, these cells did not induce any compact spheroids in non-adherent culture conditions, producing only loose multicellular aggregates, which underwent profound cell death in several days of ex vivo culturing (FIG. 10G). In contrast, dissociated cells from untreated tumor xenografts were serially passaged in vivo and in vitro (FIG. 4H shows type I collagen-adherent holoclone and floating spheroids induced during serial passaging of the untreated PPT2 mice tumor xenograft cells).

Figure 11C:
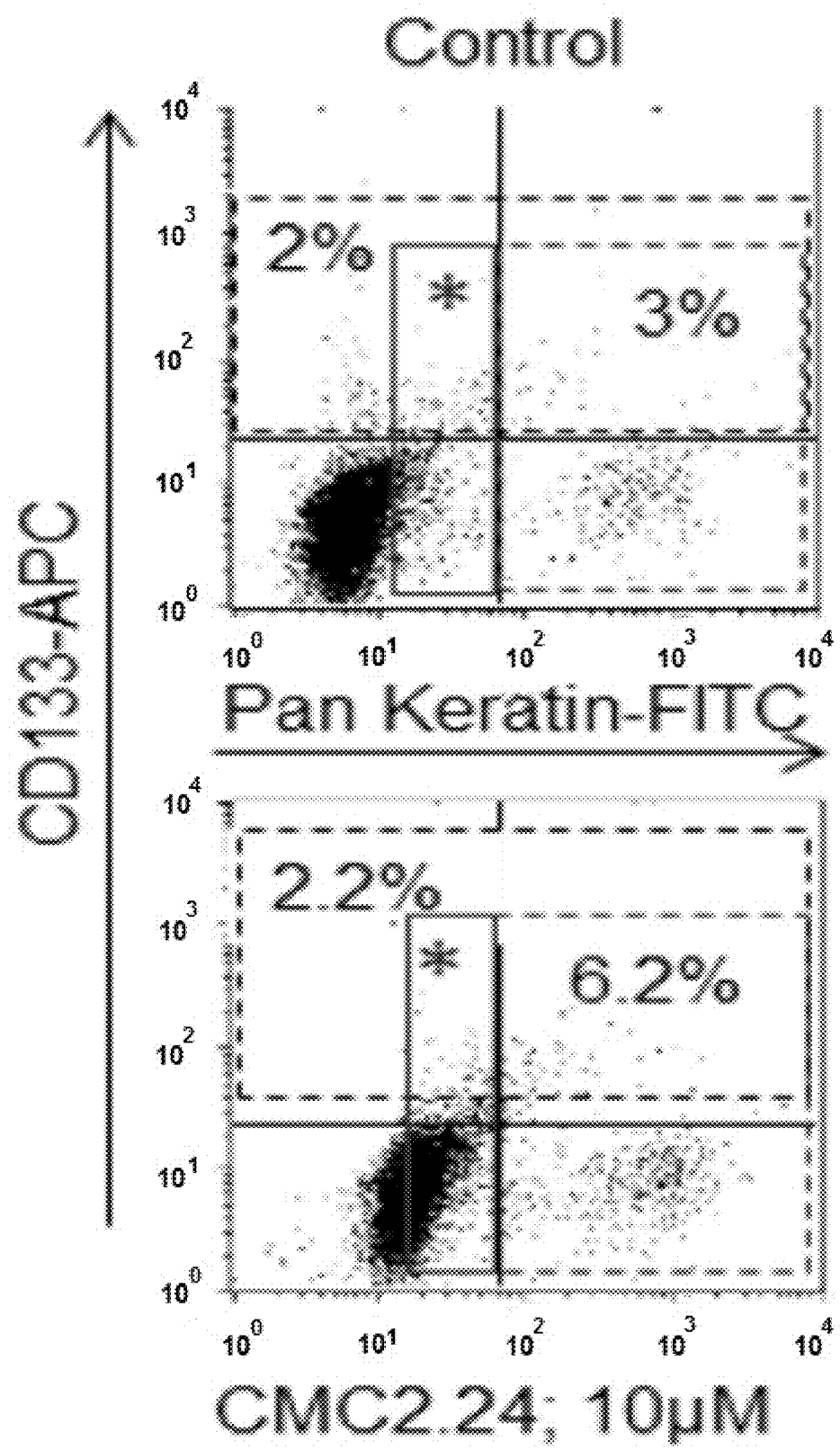
FIG. 11C: In contrast to SBT-1214, treatment with CMC2.24 did not induce an increase in the ratio of CD133$^+$ cells (black dotted areas), but similarly to SBT-1214, increased expression of the differentiation marker pan-keratin (gray dotted area adjacent to area with asterisk) and shifted the entire cell population toward differentiation (areas with asterisks).
Figure 11D:
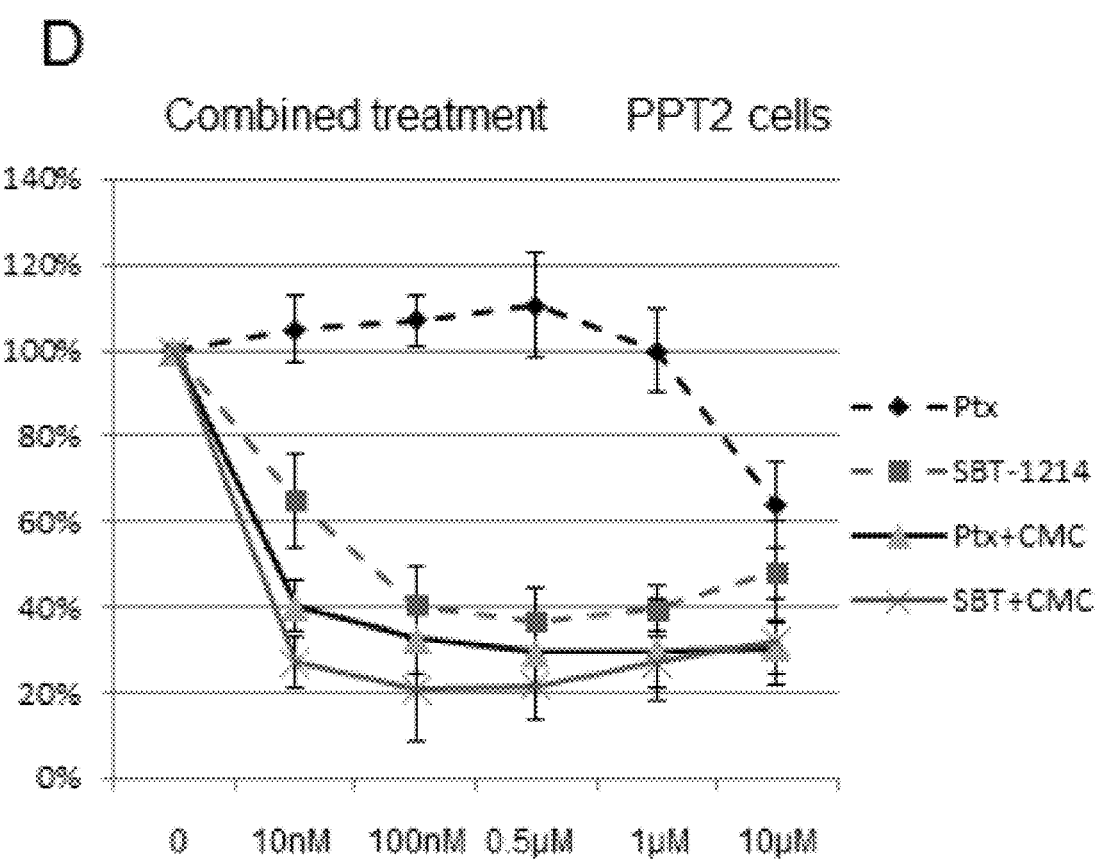
FIG. 11D: A combination of the two agents induced more significant cell death of the CD133$^+$ PPT2 cells compared to each compound as a single agent. Data were obtained with standard MMT assay. Values are the means±SD of the three independent experiments with 4 repeats for each drug concentration.
Figure 11E:
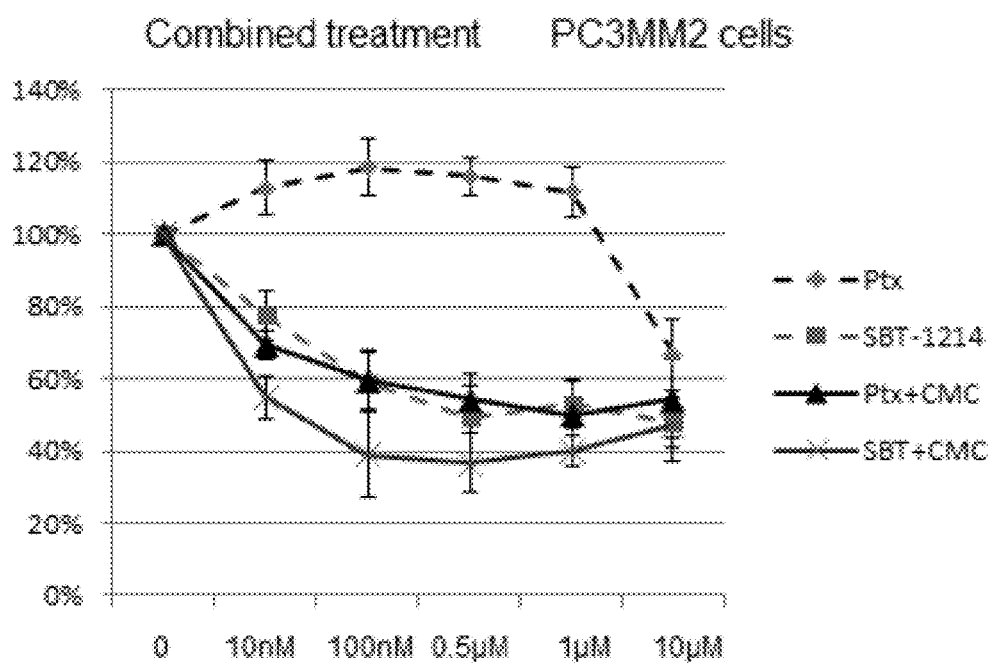
FIG. 11E: A combination of the two agents induced more significant cell death of the CD133$^+$ PC3MM2 cells compared to each compound as a single agent. Data were obtained with standard MMT assay. Values are the means±SD of the three independent experiments with 4 repeats for each drug concentration.

Example 7. Combination of SBT-1214 with CMC2.24 Increases its CSC-Targeted Cytotoxic and Stem Cell-Modulating Activities To study the potential interactions between SBT-1214 and Ptx with a novel synthetic curcuminoid, CMC2.24, the effectiveness of various drug concentrations and their combination with CMC2.24 was evaluated in the tumor-initiating fractions of the PPT2 and PC3MM2 cell lines. Cell viability was determined by the MTT assay and FACS analysis. We have found that the CMC2.24 (as well as curcumin) often exerted biphasic effects on prostate CD133$^+$ cells. Thus, treatment with low concentrations of CMC (up to 10 µM) for 72 hr stimulated cell proliferation, whereas higher doses (10-40 µM) were increasingly cytotoxic (FIG. 11A-B). FACS analysis revealed that in contrast to SBT-1214 and Ptx, CMC2.24 did not induce an increase in the ratios of cells with highest expression of CD133 (FIG. 11C; black dotted area), but led to a significant shift of the entire cell population toward differentiation (C; area with asterisk) and some increase in cells with highest expression of pan-keratin (C; gray dotted area adjacent to area with asterisk). These data indicate that low concentrations of CMC2.24 increase proliferation of the non-stem progenitors rather than CSCs. Importantly, the combination of 30 µM CMC2.24 (which is not toxic even at much higher doses (Zhang, Y. 2012) with low concentrations of SBT-1214 or Ptx (10 nM-1 µM) exerted more profound death of the CD133$^+$ cells than each compound as a single agent (FIG. 11D-E). After temporary post-treatment accumulation of the large multinucleated cells, they lost the ability to induce floating 3D spheroids and underwent profound cell death similarly to the SBT-1214-treated cells shown on FIG. 3.

Figure 4A:
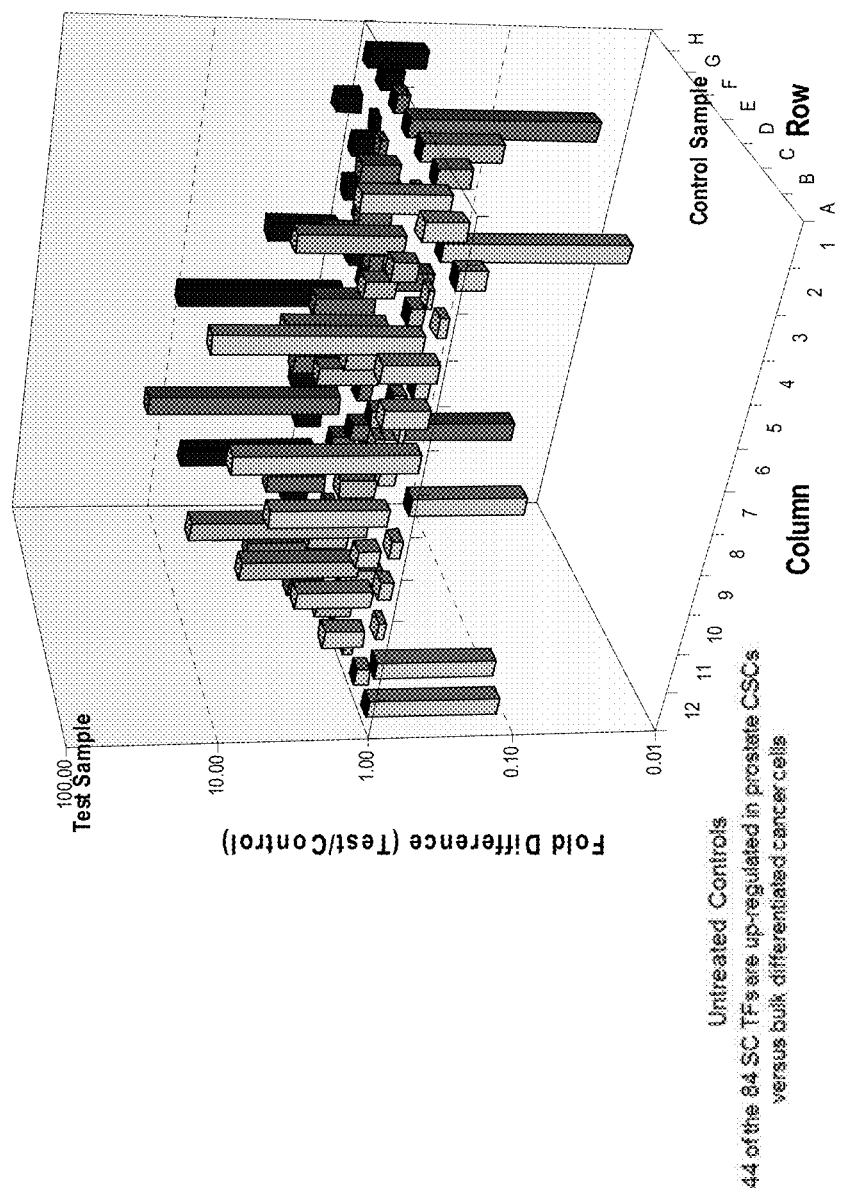
FIG. 4A: PCR Array of Stem Cell-Related TFs. Prostate Cancer patient-derived CD133$^+$ cells. Untreated control (CSCs CD133$^+$ vs. differentiated) (SABiosciences; PAHS-501).
Figure 4B:
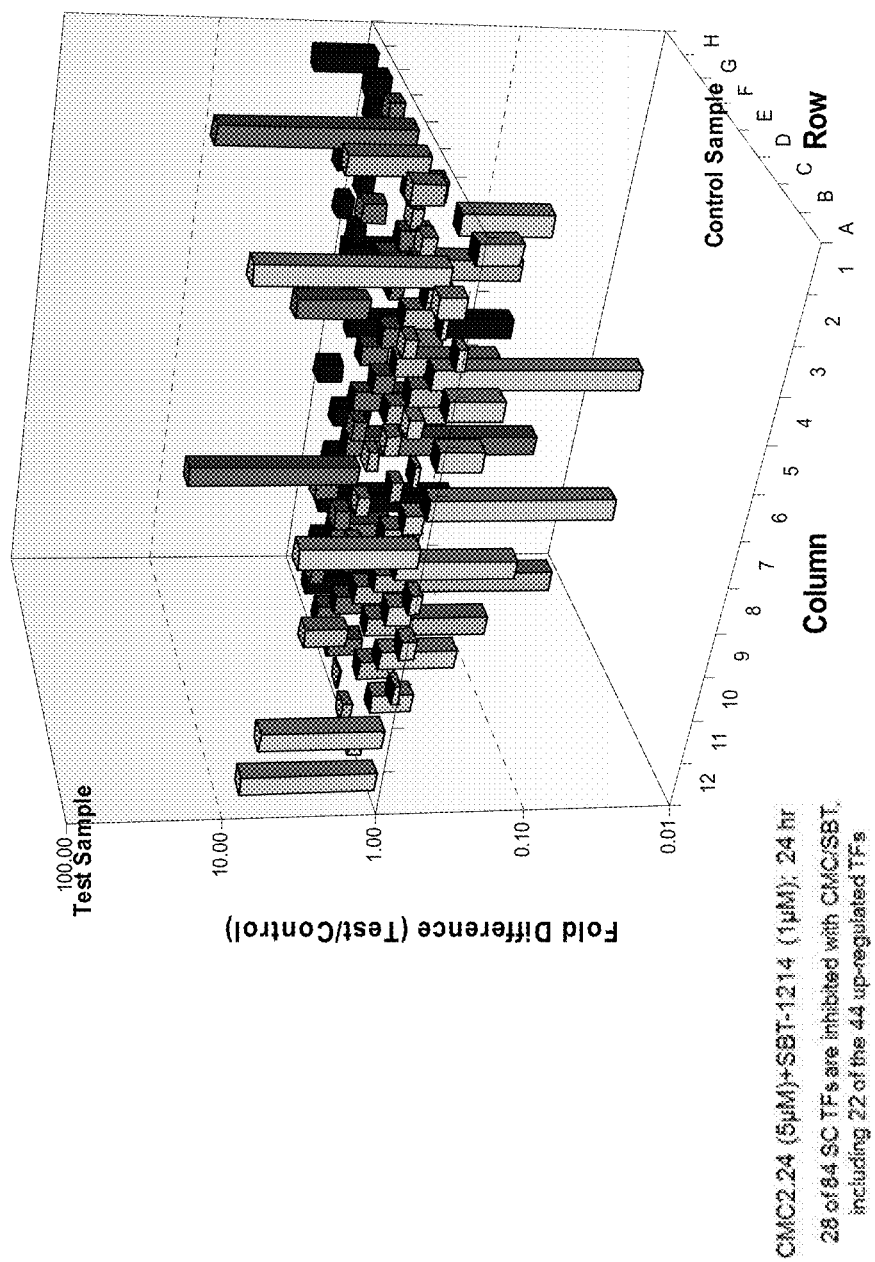
FIG. 4B: PCR Array of Stem-Cell-Related TFs. Prostate cancer patient-derived CD133$^+$ cells. Treated (Combination of CMC2.24 (5 μM)/SB-1214 (1 μM vs. untreated) (SABiosciences; PAHS-501). Post-treatment down-regulation of the over-represented prostate stemness-relevant, transcription-relevant, transcription factors after administration of SB-1214 (1 μM)/CMC2.24 (5 μM) combination for 24 hrs.
Figure 5A:
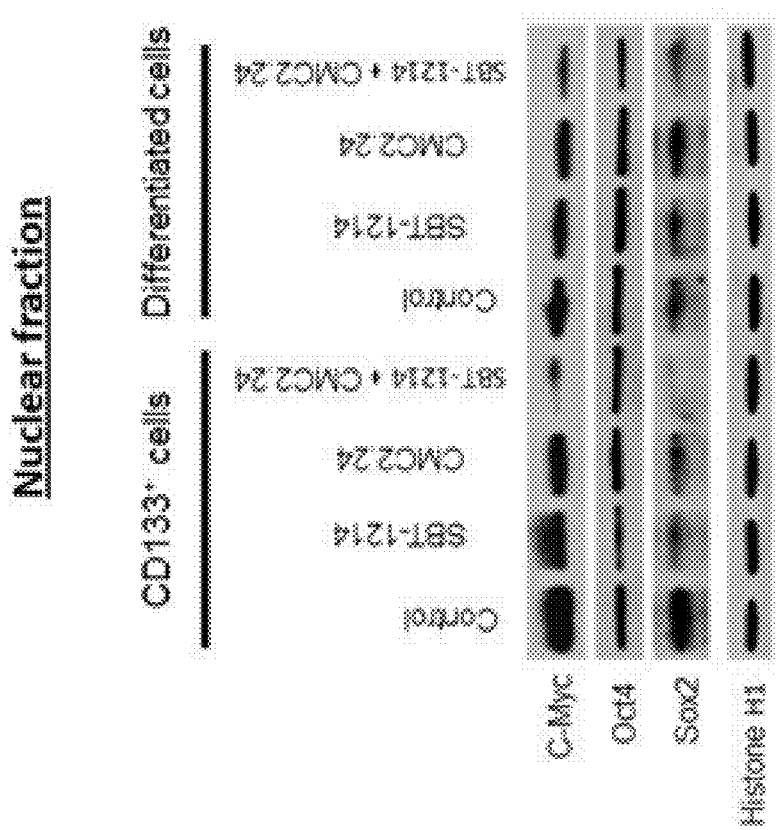
FIG. 5A: CMC2.24 and the CMC2.24/SBT-1214 combination down-regulates expression of key TFs, c-Myc, Sox-2 and Oct4 in the nuclear fraction of CSCs and their differentiated counterparts (western blot analysis).
Figure 5B:
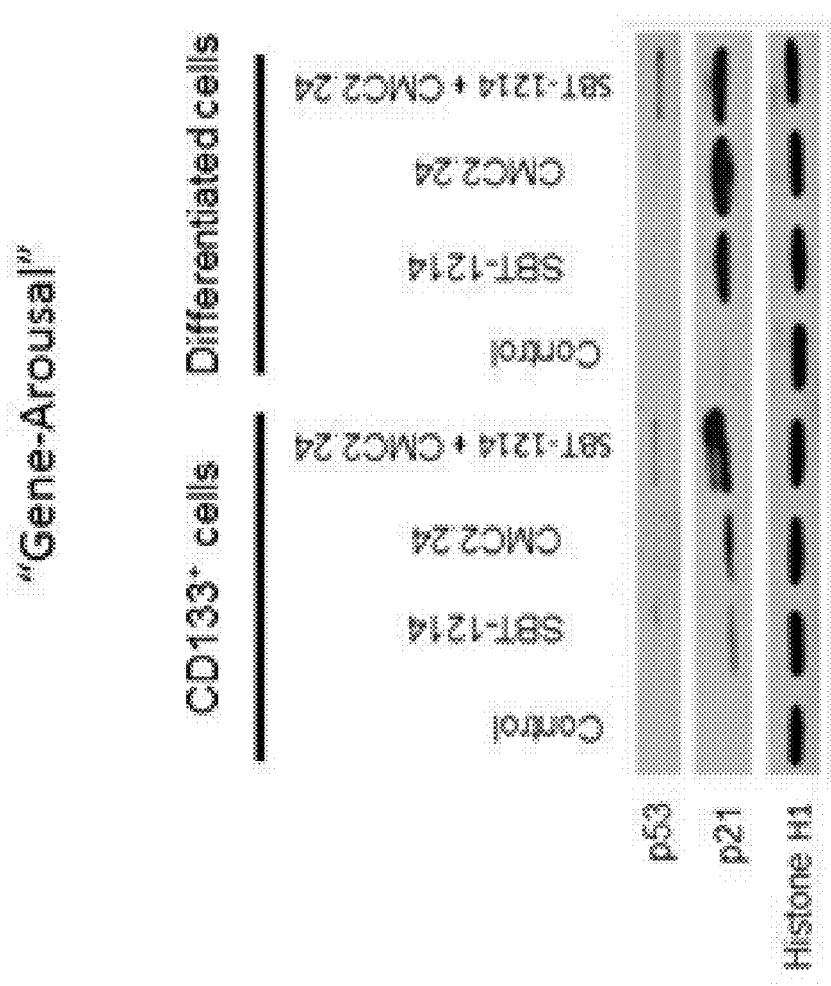
FIG. 5B: "Gene-arousal": CMC2.24/SBT-1214 combination can induce expression of the two important regulators of apoptosis, p53 and p21, which are lacking in untreated CSCs.
Figure 12:
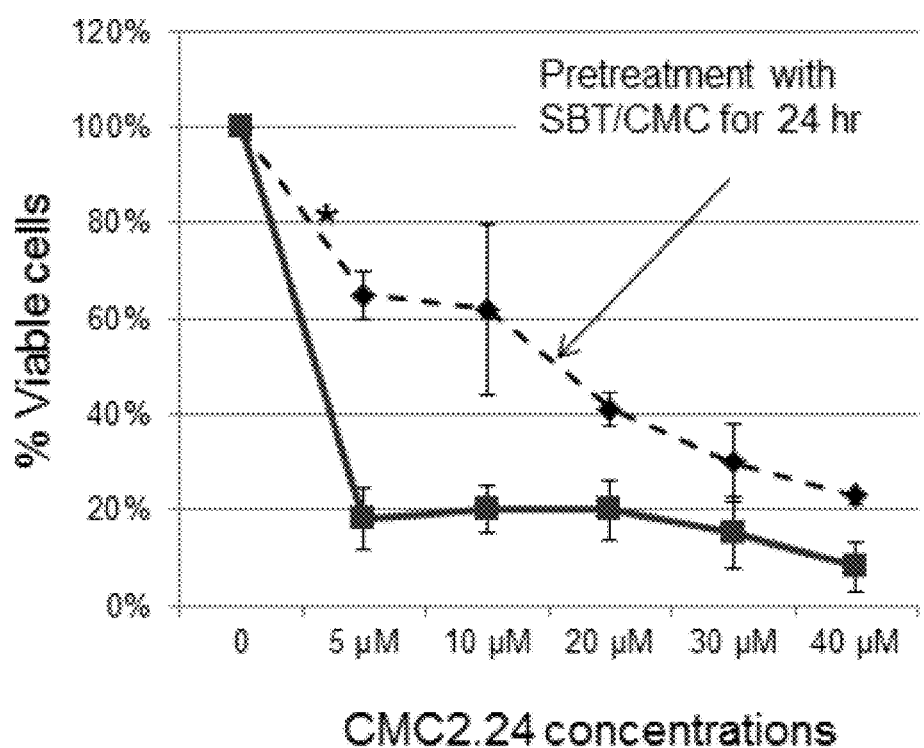
FIG. 12: The p53/p21 "gene-wake-up" induced by SBT-1214/CMC2.24 combination. Previously absent pro-apoptotic/tumor suppressor proteins, p21 and p53 were induced by single treatment with SBT-1214/CMC2.24 combination for 24 hr in both CD133$^+$ and bulk PPT2 cells. Such "gene wake-up" led to significant increase in the sensitivity of the CD133$^+$ cells to this drug combination. Pre-treatment [SBT-1214 (1 μM)+CMC2.24 (10 μM)]; second treatment [SBT-1214 (1 μM)+CMC2.24 variable]. Data were obtained with standard MMT assay.

Example 8. SBT-1214-Induced Alterations in the Stemness-Related Gene Expression Profile Using genome-wide and pathway-specific gene expression profiling, it was found that the tumorigenic cell populations isolated from the established prostate and colon cancer cell lines expressed upregulated levels of the anti-apoptotic genes, ABC transporters and the majority of stem cell-related genes (Botchkina, G. I. 2010; Rowehl, R H; Botchkina, I. L. 2009). The proteomics study on the CSC-enriched versus differentiated PC3MM2 cells revealed 198 differentially expressed proteins out of 600 analyzed ones. Among them were many proteins involved in stem cell function, cell motility, invasion, metastasis and poor prognosis, including vimentin, nestin, S100, heat shock proteins HS90A and HS90B, moesin, galectin and many others. To determine possible drug-induced alterations in stemness gene expression, CD133+ PPT2 cells were analyzed before and after treatment with the SBT-1214/CMC 2.24 combination. Using PCR array assay (PAHS 501; SABiosciences) with filtering criteria of a 1.5- or greater-fold change in expression, it was found that about 50% of the analyzed 84 stem cell-related transcription factors (TFs) were upregulated in CD133+ versus differentiated PrC cells (FIG. 4A). Among them were CDX2, DLX2, DNMT3B, EGR, FOXP3, GLI2, HOX family TFs, IRX4, JUN, KLF2, NFATC1, NR2F2, PCNA, PITX3, POU4F1, SIX2, SOX2, SOX9, TERT, WT1 and others. Single treatment with SB-1214 (1 μM) and CMC2.24 (10 μM) for 24 hours induced significant down-regulation of these over-expressed genes (FIG. 4B). Western blot analysis has shown that SBT-1214 and CMC2.24 as single agents induced moderate down-regulation of c-Myc and Sox2 in nuclear extracts of both CD133+ and bulk PPT2 cells, whereas combined drug administration led to practically complete inhibition of their expression (FIG. 5A). Importantly, nuclear fractions of both CD133+ and bulk PPT2 cells did not express the two tumor suppressors/regulators of apoptosis, p53 and p21 (FIG. 5B), which partially can explain their extreme resistance to anti-cancer drugs. Both SBT-1214 and CMC2.24, and especially their combination induced expression of p21 and p53. Such "gene wake-up" induced by pretreatment with the drug combination (SB-1214; 1 μM and CMC2.24; 10 μM) for 24 hours dramatically increased further sensitivity of these highly drug-resistant cells to the second treatment, leading to virtually complete death of the CSC-enriched cells (FIG. 5B; FIG. 12).

Example 9. CMC2.24 in Combination with Various Chemotherapeutic and Cytotoxic Agents CMC2.24, in combination with the chemotherapeutic and cytotoxic agents described herein, have analogous activity to inhibit growth of CSCs, inhibit CSC-relevant TFs, and down-regulate CSC-relevant genes as the combination of CMC2.24 and SBT-1214 described herein.

Example 10. CMC2.24 Derivatives

An additional aspect of the invention provides analogues of CMC2.24 that may be used to inhibit growth of CSCs, inhibit CSC-relevant TFs, and down-regulate CSC-relevant genes. The analogs of CMC2.24, which are described by formula (1) are structurally similar to CMC2.24 and have analogous activity to CMC2.24. The analogs of CMC2.24, in combination with a chemotherapeutic agent, have analogous activity to the combination of CMC2.24 and SBT-1214 described herein.

Example 11. Analogs of CMC2.24

Additional compounds (Scheme 1) have been manufactured as described in PCT International Application WO 2010/132815 A9. The analogs of CMC2.24 shown below in Scheme 1 have analogous activity to CMC2.24.

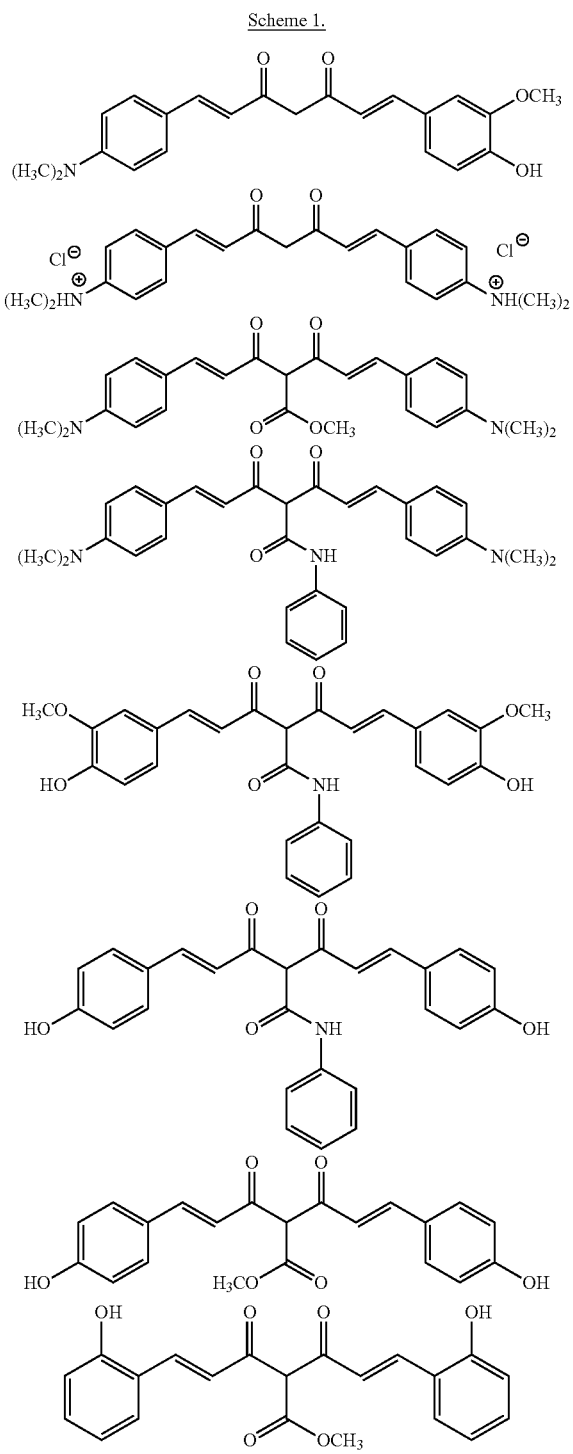

Scheme 1.

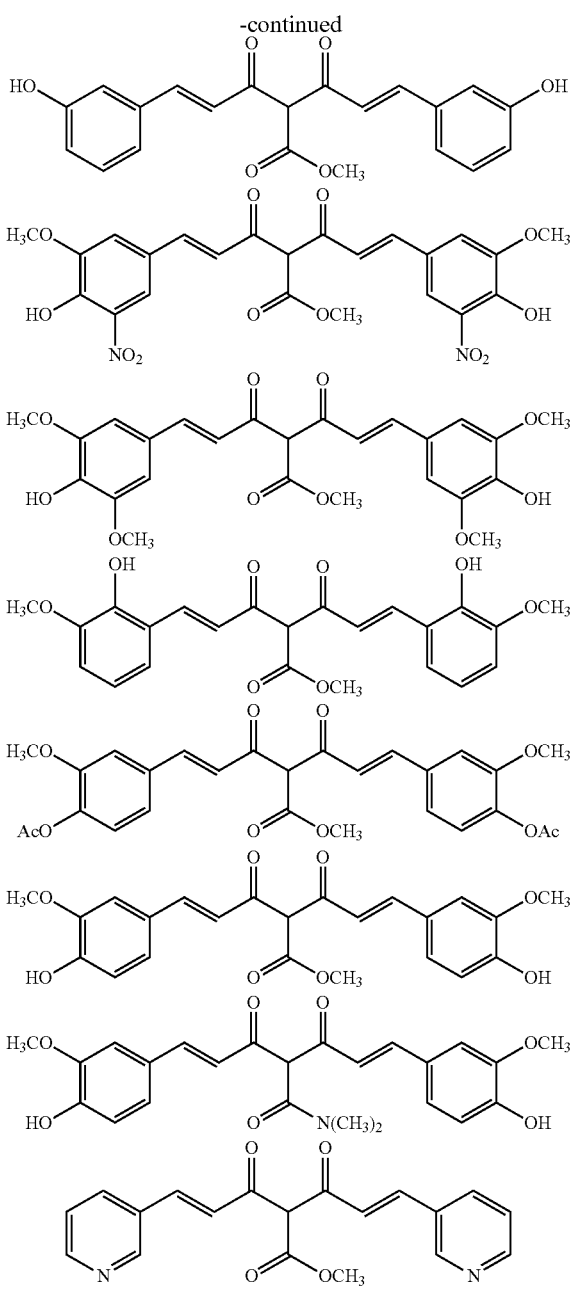

Discussion

It has been shown that the new-generation taxoid, SBT-1214 exhibits high efficiency against colon cancer in vivo, inducing complete regression of drug-resistant colon tumor xenografts in all surviving mice with tumor growth delay up to 201 days (Kuznetsova et al., 2006). Such promising antitumor activity of SBT-1214 led us to suggest that this compound can specifically target tumor-specific CSCs by inhibiting some sternness-related signaling pathways and/or promoting their differentiation.

Since CSC-enriched CD 133+ and CD44+ cell populations are more resistant to conventional therapies than other more differentiated cells, the cytotoxic effects of SBT-1214 were tested against such cell populations in colon (Botchkina et al., 2010) and prostate (FIG. 5) cancers. The genomic differences were determined between two types of prostate and colon cancer cells, i.e. CSC-enriched $CD133^{high}/CD44^{high}$ cell phenotypes and $CD133^{high}/CD44^{high}$-induced floating spheroids grown under sternness-promoting SBT-1214 conditions, and CSC-specific alterations induced by taxoid SBT-1214 were evaluated. Thus, using a stem cell-specific PCR array assay (SABiosciences) it was found that a single treatment of the 3D spheroids induced by $CD133^{high}/CD44^{high}$ cell populations with relatively low concentrations of the SBT-1214 resulted not only in significant down-regulation of the majority of stem cell-related genes, but more importantly, led to a dramatic reduction of their sphere-forming capacity. In addition, the expression of several key regulators of pluripotency of the embryonic stem cells, Oct-4, Sox-2, Nanog, Lin-28 and c-Myc, was also significantly inhibited after single treatment with 0.01 µg/ml of SBT-1214.

Anti-cancer effects of curcumin (diferuloylmethane) have been demonstrated in a large number of studies (e.g. overview of these studies is reported by Mimeault & Batra, 2011). Of great therapeutic interest, curcumin has been reported to inhibit the clonogenic capacity and induce the anti-proliferative and apoptotic effects on drug-resistant cells expressing stem cell markers (Yu et al., 2009; Fong et al., 2010; Kakarala et al., 2010; Bao et al., 2011). It also can improve the cytotoxic effects induced by diverse chemotherapeutic drugs on these immature cancer cells.

Recent data suggest that the anti-carcinogenic effects induced by curcumin are mediated via the modulation of multiple oncogenic signaling transduction elements. Potential mechanisms of its anti-cancer activity include the down-regulation of the epidermal growth factor receptor (EGFR) family members (EGFR/erbBI and erbB2/HER2), insulin-like growth factor type-1 receptor (IGF-IR), sonic hedgehog (SHH/GLIs) and Wnt/β-catenin and their downstream signaling effectors, inhibition of the signal transducers and activators of transcription (STATs), c-jun/activator protein-1 (AP-1), phosphatidylinositol-3'-kinase (PI3K)/Akt, nuclear factor-kappaB (NF-κB) and its targeted genes such as interleukin-6 (IL-6), cyelooxygenase-2 (COX-2) and matrix metalloproteinases, MMPs.

Other signaling components modulated through curcumin include the up-regulation of $p21^{WAP1}$ and $p27^{KIP1}$ cyclin-dependent kinase inhibitors and down-regulation of anti-apoptotic Bcl-2, Bel-xL, survivin and glyoxalase 1, as well as the up-regulation of pro-apoptotic Bax, Bad and caspase cascade-induced apoptosis. Curcumin and its major metabolite tetrahydrocurcumin have also been reported to down-regulate the expression and/or activity of multiple ABC multi-drug transporters, including ABCG2, MDR-1 encoding P-glycoprotein, ABCB1 and multidrug resistance protein-1, MRP-1, ABCC1 (rev. Mimeault & Batra, 2011). However, the insolubility and the high metabolic instability coupled with poor systemic bio-availability of curcumin, limit its therapeutic efficacy in human therapy.

CMC2.24 has a much higher bioavailability and activity compared to curcumin, and possesses profound anti-inflammatory, antioxidant and anti-cancer activities against highly metastatic prostate and colon CSCs ($CD44^{hi}/CD133^{hi}/CXCR4^{hi}$ cell phenotype). These effects also include the induction of the pro-apototic proteins P21 and P53 (FIG. 5B), normally absent in CSCs.

Transcription Factors (TFs) represent the largest family of human proteins (approximately 2600), and approximately 10% of genes in the genome code for TFs, reflecting the extreme importance of these proteins (Babu et al., 2004). The TFs participate at the termination points of all known signal transduction pathways, and a majority of the oncogenic signaling pathways converge on sets of TFs that ultimately control gene expression patterns resulting in tumor formation, progression and metastasis. Cancer development and progression to aggressive and metastatic stages, as well as treatment resistance and disease relapse are associated with the deregulation and sustained activation of multiple tumorigenic pathways (Kesmodel & Spitz, 2003; Mimeault et al., 2007; 2008; 2010; Nautiyal et al., 2011).

Particular genes require the cooperative action of several different transcription factors for efficient expression, and the combinatorial use of such a large number of the human TFs allows for the unique and precise regulation of each gene in the human genome (Brivanlou & Darnell, 2002). Under normal physiological conditions many TFs are inactive, and their expression and activities are tightly regulated. However, in cancer, aberrant activation of the TFs leads to the deregulated expression of multiple gene sets associated with tumor development and progression (Libermann & Zerbini, 2006). Because the majority of oncogenic signaling pathways converge on sets of TFs that ultimately control gene expression patterns resulting in tumor formation, progression and metastasis, both CSCs and CSC relevant TFs represent a critically important and logical target for therapeutic intervention.

Several attempts to inhibit different TFs have been reported, however, chemical intractability of TFs has limited the discovery of effective synthetic compounds. Direct inhibition of transcription factor complexes remains a central challenge because these proteins lack surface involutions suitable for high-affinity binding by small molecules. Recently, progress has been made on the Notch pathway after demonstration of direct, high-affinity binding of the hydrocarbon-stapled peptide SAHM1, which prevented assembly of the active transcriptional complex (Moellering et al., 2009). Therefore, development of the therapeutic strategies which can affect multiple deregulated gene products may represent a potentially better strategy than the targeting of one specific oncogenic product. In this context, compound CMC 2.24 (related to the known nontoxic anti-inflammatory drug curcumin) has a high potential for the treatment of human cancer, either as a single CSC-targeted anti-cancer substance or in combination with a second anti-tumor agent. Although a number of TFs, have been identified as playing key roles in promoting oncogenesis, tumor growth and metastasis, only limited information exists on the TF profiling in homogeneous, purified CSCs. Up to now, large-scale TF expression profiling has not been reported for human prostate or colon CSCs.

CSCs represent a critically important and logical target for therapeutic intervention. It was demonstrated the synergistic activity of the SBT-1214/CMC2.24 combination against highly tumorigenic and highly drug-resistant prostate and colon CSCs, which express a large number of genes and transcription factors involved in stem cell regulation and functioning, cancer development and progression, drug resistance and metastasis.

Microtubule stabilizers such as paclitaxel (Taxol) and docetaxel can be initially effective in treating patients with androgen-independent prostate cancer, but the cancer almost invariably recurs in a more aggressive form (Jemal, A. 2011; Zivi, A. 2010; Reya, T. 2001). Previously we have shown that the new-generation taxoid SBT-1214 induced complete regression of drug-resistant colon tumor xenografts in all surviving mice with unusually long-term tumor growth delay (>167 days) (Kuznetsova, L. 2006). Later, we have found that this drug molecule induced significant down-regulation of multiple stemness-related genes, including several key transcription factors involved in the regulation of stem cells, cancer development and progression (Botchkina, GI 2010). Of note, it was shown that docetaxel, which is the standard first-line therapy in metastatic castration-resistant prostate cancer, can promote drug resistance and de-differentiation (epithelial to mesenchymal transition; EMT) of the DU-145 and PC-3 cells via TGF-beta mechanism (Marin-Aguilera, M. 2012). Cytotoxicity against prostate cancer cells can be significantly reduced with a combination of Paclitaxel and cyclopamine, a natural steroidal alkaloid that inhibits the Hedgehog pathway (Singh, S. 2012). The anti-cancer effects of another natural phytochemical, curcumin (diferuloylmethane) were recently demonstrated in a large number of studies. Of great therapeutic interest, curcumin has been reported to induce the anti-proliferative and apoptotic effects on drug-resistant stem-like cells, and to improve the cytotoxic effects induced by diverse chemotherapeutic drugs (Yu, Y. 2009; Fong, D. 2010; Kakarala, M. 2010; Bao, B. 2011). However, the poor systemic bioavailability of curcumin and its high metabolic instability limit its therapeutic efficacy. Therefore, it was of great clinical significance to test the efficacy of CMC2.24, which has no systemic toxicity and has much higher bioavailability and activity compared to curcumin (Zhang, Y. 2012).

It was determined that a combination of the relatively low concentrations of SBT-1214 (0.1-1 µM) with CMC2.24 (30-40 µM) induced up to 80-90% death of the highly tumorigenic and highly drug-resistant prostate CD133$^+$ cells maintained under sternness-promoting culture conditions. In addition, the significant up-regulation of the previously absent expression of the pro-apoptotic proteins, p53 and p21 ("gene wake-up" effect), and as a result, a dramatic increase in sensitivity to the following treatment implies that this drug combination reverses sensitivity to other anti-cancer drugs. Similar effects were reported for curcumin, which has been shown to activate p21 in breast (Aggarwal, BB 2007), prostate (Hour, TC 2002) and colon (Su, CC 2006) cancer cell lines. In earlier studies, the reduced expression of p21 in prostate cancer was associated with poor survival outcome (Matsushima, H. 1998; Cheng, L. 2000). The fact that the SBT-1214/CMC2.24 combination exerted high direct cytotoxicity and down-regulated the sternness state of highly tumorigenic and clonogenic patient-derived CD133$^+$ PPT2 cells is highly promising, because it can also be effective against other patient-derived prostate CSC populations.

The data described herein indicates that the anti-cancer efficacy of SBT-1214 in vitro and in vivo is most likely due to the down-regulation of multiple stem cell-related genes in the tumorigenic cell population (in addition to its known efficacy as a mitotic poison against proliferating cancer cells). It has also been demonstrated herein that a combination of SBT-1214 with CMC2.24 exerts more profound pleiotropic, pan-inhibitory effects on a large number of sternness genes and transcription factors. In particular, modulation of multiple stem cell-relevant transcription factors and the pro-apoptotic p21 and p53 "gene wake-up" mechanism can potentially reverse resistance of CSCs to anti-cancer treatment and improve clinical outcome. The two compounds exert pleiotropic CSC-targeted activities against primary patient-derived, spontaneously immortalized, low passage, highly tumorigenic and clonogenic prostate cancer cells with CD133$^{+/high}$/CD44$^{+/high}$/CD49f$^{+/high}$/EpCAM$^{+/high}$ phenotype.

The data described herein provides a strong basis for the claim that CMC2.24 and its congeners, either alone or in combination with a traditional chemotherapeutic or cytoxic agent, possesses selective activity against highly tumorigenic and highly drug-resistant prostate and colon CSCs and against CSC-relevant genes and TFs. This likely represents a new and viable approach to the treatment of mammalian cancer at both the initial and the metastatic phase of the disease.

REFERENCES

Aggarwal B B, Sundaram C, Malani N, Ichikawa H. (2007) Curcumin: the Indian solid gold. Adv Exp Med Biol 595:1-75.

Aktas B, Tewes M, Fehm T, Hauch S, Kimmig R, Kasimir-Bauer S. Stem cell and epithelial-mesenchymal transition markers are frequently overexpressed in circulating tumor cells of metastatic breast cancer patients. Breast Cancer Res; 11(4):R46, 2009.

Babu M M, Luscombe N M, Aravind L, Gerstein M, Teichmann S A. "Structure and evolution of transcriptional regulatory networks". Curr. Opin. Struct. Biol. 14 (3): 283-91, 2004.

Balic M, Lin H, Young L, Hawes D, Giuliano A, McNamara G, Datar R H, Cote R J. Most early disseminated cancer cells detected in bone marrow of breast cancer patients have a putative breast cancer stem cell phenotype. Clin Cancer Res; 12(19):5615-5621, 2006.

Bao S, Wu Q, McLendon R E, Hao Y, Shi Q, Hjelmelad A B, Dewhirst M W, Bigner D D and Rich J N. Glioma stem cells promote radioresistance by preferential activation of the DNA damage response. Nature 444:756-760, 2006.

Bao B, Ali S, Kong D, Sarkar S H, Wang Z, Banerjee S, Aboukameel A, Padhye S, Philip P A and Sarkar F H. Anti-Tumor Activity of a Novel Compound-CDF Is Mediated by Regulating miR-21, miR-200, and PTEN in Pancreatic Cancer. PLoS One; 6(3): e17850, 2011.

Baretton G B, Valina C, Vogt T, Schneiderbanger K, Diebold J and Löhrs U. (1994) Interphase cytogenetic analysis of prostate carcinomas by use of nonisotopic in situ hybridization. Cancer Res 54: 4472-4480.

Bleau A M, Hambardzumyan D, Ozawa T, Fomchenko E I, Huse J T, Brennan C W, Holland E C. PTEN/PI3K/Akt pathway regulates the side population phenotype and ABCG2 activity in glioma tumor stem-like cells. Cell Stem Cell. 4(3):226-35, 2009.

Botchkina I L, Rowehl R A, Rivadeneira D E, Karpeh M S Jr, Crawford H, Dufour A, Ju J, Weng Y, Leyfman Y, and Botchkina G I. Phenotypic Subpopulations of Metastatic Colon Cancer Stem Cells: Genomic Analysis. Cancer Genomics Proteomics, 6(1): 19-30, 2009.

Botchkina G I, Wang Y, Savitt A G, Rowehl R A, Leyfman L, Wang H, Zhu S, Ju J and Ojima I. New-generation taxoid SB-T-1214 inhibits stem cell-related gene expression in three-dimensional cancer spheroids induced by two phenotypic subpopulations of colon tumor-initiating cells. Molecular Cancer, 9: 192-204, 2010.

Botchkina G I & Ojima I. Prostate and colon cancer stem cells as a target for anti-cancer drug development. Book chapter in Stem Cells, INTECH, Vienna, Austria, ISBN: 978-953-307-225-8, 2011.

Brabletz T, Jung A, Spaderna S, Hlubek F, Kirchner T. Opinion: migrating cancer stem cells—an integrated concept of malignant tumour progression. Nat Rev Cancer.; 5(9):744-749, 2005.

Brekelmans C T, et al. Tumour characteristics, survival and prognostic factors of hereditary breast cancer from BRCA2-, BRCA1- and non-BRCA1/2 families as compared to sporadic breast cancer cases. Eur J Cancer.; 43(5):867-76, 2007.

Brivanlou A H, and J. E. Darnell, Signal transduction and the control of gene expression. Science 295 (2002) 813-818.

Cheng L, Lloyd R V, Weaver A L, Pisansky T M, Cheville J C, Ramnani D M, Leibovich B C, Blute M L, Zincke H, Bostwick D G. (2000) The cell cycle inhibitors p21WAF1 and p27KIP1 are associated with survival in patients treated by salvage prostatectomy after radiation therapy. Clin Cancer Res 6:1896-1899.

Clarke M F, and M. Fuller, Stem cells and cancer: Two faces of eve. Cell 124 (2006) 1111-1115.

Collins A T, Berry P A, Hyde C, Stower M J, Maitland N J. Prospective identification of tumorigenic prostate cancer stem cells. Cancer Res, 65: 10946-10951, 2005.

Dirks P B. Cancer: Stem cells and brain tumours. Nature 444, 687-688, 2006.

Dylla S J, Beviglia L, Park I K, Chartier C, Raval J, Ngan L, Pickell K, Aguilar J, Lazetic S, Smith-Berdan S, et al. (2008) Colorectal cancer stem cells are enriched in xenogeneic tumors following chemotherapy. PLoS One 3:e2428.

Eramo A, et al. Chemotherapy resistance of glioblastoma stem cells Cell Death and Differentiation 13, 1238-1241, 2006.

Fong D, Yeh A, Naftalovich R, Choi T H, Chan M M: Curcumin inhibits the side population (SP) phenotype of the rat C6 glioma cell line: towards targeting of cancer stem cells with phytochemicals. *Cancer Lett*, 293:65-72, 2010.

Hermann P C, Huber S L, Herrler T, Aicher A, Ellwart J W, Guba M, Bruns C J, and Heeschen C. (2007) Distinct Populations of Cancer Stem Cells Determine Tumor Growth and Metastatic Activity in Human Pancreatic Cancer. Cell Stem Cell 1:313-323.

Hermann P C, Bhaskar S, Cioffi M, Heeschen C. Cancer stem cells in solid tumors. Semin Cancer Biol.; 20:77-84, 2010.

Hour T C, Chen J, Huang C Y, Guan J Y, Lu S H, Pu Y S. (2002) Curcumin enhances cytotoxicity of chemotherapeutic agents in prostate cancer cells by inducing p21 (WAF1/CIP1) and C/EBPbeta expressions and suppressing NF-kappaB activation. Prostate 51:211-218.

Hutchinson E. Stem cells: Tumour stem cells generate vasculature. Nature Reviews Cancer 11, 4, 2011.

Hynes P G and Kelly K. Prostate cancer stem cells: The case for model systems. J Carcinog. 2012; 11: 6.

Jemal A, Bray F, Center M M, Ferlay J, Ward E, Forman D. Global Cancer Statistics. CA Cancer J Clin; 61:69-90, 2011.

Kakarala M, et al. Targeting breast stem cells with the cancer preventive compounds curcumin and piperine. *Breast Cancer Res Treat*, 122:777-785, 2010.

Kelly K and Yin J J. Prostate cancer and metastasis initiating stem cells. Cell Research, 18:528-537, 2008.

Kesmodel S B, Spitz F R: Gene therapy for cancer and metastatic disease. Expert Rev Mol Med; 5:1-18, 2003.

Klarmann G J, et al. Invasive prostate cancer cells are tumor initiating cells that have a stem cell-like genomic signature. Clin Exp Metastasis, 26(5):433-46, 2009.

Koivisto P, Hyytinen E, Palmberg C, Tammela T, Visakorpi T, Isola J, Kallioniemi O P. (1995) Analysis of geneic changes underlying local recurrence of prostate carcinoma during androgen deprivation therapy. Am J Pathology 147:1608-1614.

Kuznetsova L, Chen C, Sun L, Wu X, Pepe A, Veith J M, Pera P, Bernacki R J, Ojima I. (2006) Syntheses and evaluation of novel fatty acid-second-generation taxoid conjugates a promising anticancer agents. Bioorg Med Chem Lett 16:974-977.

Kwabi-Addo B, Ozen M and Ittmann M. The role of fibroblast growth factors and their receptors in prostate cancer. Endocr Relat Cancer December 1, 11 709-724, 2004.

Libermann T A, Zerbini L F. Curr Gene Ther. Targeting transcription factors for cancer gene therapy. February; 6(1):17-33, 2006.

Marin-Aguilera M, Codony-Servat J, Kalko S G, Fernández P L, Bermudo R, Buxo E, Ribal M J, Gascón P, Mellado B. (2012) Identification of docetaxel resistance genes in castration-resistant prostate cancer. Mol Cancer Ther 11(2):329-39.

Matsushima H, Sasaki T, Goto T, Hosaka Y, Homma Y, Kitamura T, Kawabe K, Sakamoto A, Murakami T, Machinami R. (1998) Immunohistochemical study of p21WAF1 and p53 proteins in prostatic cancer and their prognostic significance. Hum Pathol 29:778-783.

Miki J, Rhim J S. Prostate cell cultures as in vitro models for the study of normal stem cells and cancer stem cells. Prostate Cancer Prostatic Dis, 11(1):32-9, 2008.

Mimeault M, Hauke R, Mehra P P, Batra S K. Recent advances in cancer stem/progenitor cell research: therapeutic implications for overcoming resistance to the most aggressive cancers. J Cell Mol Med 11:981-1011, 2007.

Mimeault M, Batra S K: Targeting of cancer stem/progenitor cells plus stem cell-based therapies: the ultimate hope for treating and curing aggressive and recurrent cancers. Panminerva Med; 50:3-18, 2008.

Mimeault M, Batra S K: New promising drug targets in cancer- and metastasisinitiating cells. Drug Discov Today; 15:354-364, 2010.

Mimeault M, and S. K. Batra, Potential applications of curcumin and its novel synthetic analogs and nanotechnology-based formulations in cancer prevention and therapy. Chinese Medicine 6 (2011) 31.

Mimeault M, and S. K. Batra S K. (2010) New advances on critical implications of tumor- and metastasis-initiating cells in cancer progression, treatment resistance and disease recurrence. Histol. Histopathol 25 1057-1073.

Moellering R E, Cornejo M, Davis T N, Del Bianco C, Aster J C, Blacklow S C, Kung A L, Gilliland D G, Verdine G L, Bradner J. Direct inhibition of the NOTCH transcription factor complex". Nature 462 (7270): 182-8, 2009.

Miyoshi Y, Uemura H, Fujinami K, Mikata K, Harada M, Kitamura H, Koizumi Y, Kubota Y. (2000) Fluorescence in situ hybridization evaluation of c-myc and androgen receptor gene amplification and chromosomal anomalies in prostate cancer in Japanese patients. Prostate 43: 225-232.

Nautiyal J, Du J, Yu Y, Kanwar S S, Levi E, Majumdar A P. EGFR regulation of colon cancer stem-like cells during aging and in response to the colonic carcinogen dimethylhydrazine. Am J Physiol Gastrointest Liver Physiol. Jan. 26. 2012, 302(7):G655-63.

O'Brien C A, A. Pollett, S. Gallinger, and J. Dick, A human colon cancer cell capable of initiating tumor growth in immunodeficient mice. Nature 445 (2007) 106-110.

Patrawala L, Calhoun T, Schneider-Broussard R, Li H, Bhatia B, Tang S et al. Highly purified CD44(+) prostate cancer cells from xenograft human tumors are enriched in tumorigenic and metastatic progenitor cells. Oncogene, 25: 1696-1708, 2006.

Reya T, S. J. Morrison, M. F. Clarke, and I. L. Weissman, Stem cells, cancer, and cancer stem cells. Nature 414 (2001) 105-111.

Ricci-Vitiani L, D. G. Lombardi, E. Pilozzi, M. Biffoni, M. Todaro, C. Peschle, and R. De Maria, Identification and expansion of human colon-cancer-initiating cells. Nature 445 (2007) 111-115.

Rowehl R H, Crawford H, Dufour A, Leyfman Y, Ju J, and Botchkina G I. Genomic Analysis of Prostate Cancer Stem Cells Isolated from Highly Metastatic Cell Line. Cancer Genomics and Proteomics. 5(6):301-309, 2008.

Shen M M and Abate-Shen C. Molecular genetics of prostate cancer: new prospects for old challenges. Genes Dev, 24(18):1967-2000, 2010.

Singh S, Chitkara D, Mehrazin R, Behrman S W, Wake R W, Mahato R I. (2012) C hemoresistance in Prostate Cancer Cells Is Regulated by miRNAs and Hedgehog Pathway. PLoS One 7:e40021.

Su C C, Lin J G, Li T M, Chung J G, Yang J S, Ip S W, Lin W C, Chen G W. (2006) Curcumin-induced apoptosis of human colon cancer colo 205 cells through the production of ROS, Ca2+ and the activation of caspase-3. Anticancer Res 26:4379-4389.

Todaro M, et al. Colon cancer stem cells dictate tumor growth and resist cell death by production of interleukin-4. Cell Stem Cell, 1:389-402, 2007.

Tortoreto M, et al. Highly tumorigenic lung cancer CD133+ cells display stem-like features and are spared by cisplatin treatment. Proc Natl Acad Sci USA, 106(38):16281-6, 2009.

van Brussel J P, Mickisch G H. Multidrug resistance in prostate cancer. Onkologie 26 (2003) 175-181.

Visvader J E, and G. J. Lindeman, Cancer stem cells in solid tumours: accumulating evidence and unresolved questions. Nat. Rev. Cancer 8 (2008) 755-768.

Woodward W A, Chen M S, Behbod F, Alfaro M P, Buchholz T A, Rosen J M. (2007) WNT/beta-catenin mediates radiation resistance of mouse mammary progenitor cells. Proc Natl Acad Sci USA 104:618-623.

Yu Y, G. Ramena, and R. C. Elble, The role of cancer stem cells in relapse of solid tumors. Front Biosci (Elite Ed) 4 (2012) 1528-1541.

Yu Y, Kanwar S S, Patel B B, Nautiyal J, Sarkar F H, Majumdar A P. (2009) Elimination of Colon Cancer Stem-Like Cells by the Combination of Curcumin and FOLFOX. Transl Oncol 2:321-328.

Zhang Y, Gu Y, Hsi-Meng Lee E, Hambardjieva K, Vrankova L, Golub M, Johnson F. (2012) Design, synthesis and biological activity of new polyenolic inhibitors of matrix metalloproteinases: a focus on chemically-modified curcumins. Curr Med Chem 19(25):4348-58.

What is claimed is:

1. A method of inhibiting the growth of or promoting differentiation of cancer stem cells (CSCs) or down-regulating cancer stem cell-relevant transcription factors in a patient in need thereof comprising contacting the cancer stem cells in the patient with a compound having the structure:

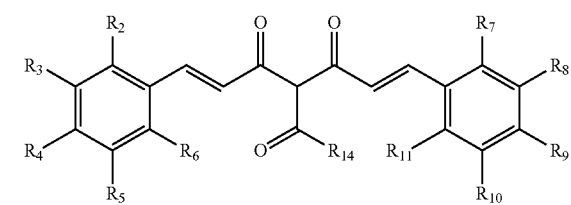

wherein $R_{14}$ is $C_{2-10}$ alkyl, $C_{2-10}$ alkenyl, $C_{2-10}$ alkynyl, heteroaryl, heterocyclyl, methoxy, —$OR_n$, —$NR_{16}R_{17}$, or

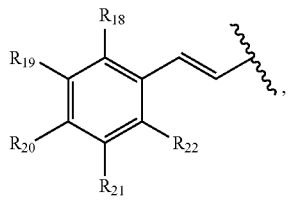

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-40}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, or $C_{2-10}$ alkynyl; and wherein each occurrence of alkyl, alkenyl, or alkynyl is branched or unbranched, unsubstituted or substituted; and or a salt thereof, so as to thereby inhibit the growth of or promote differentiation of the cancer stem cells (CSCs) or down-regulate cancer stem cell-relevant transcription factors.

2. The method of claim 1, further comprising contacting the cancer stem cell with a chemotherapeutic agent.

3. The method of claim 1, wherein the cancer stem cell-relevant transcription factors are at least five (5) transcription factors selected from the group consisting of CDX2, DLX2, EGR3, FOXP3, GLI2, HOXA2, HOXA7, HOXB3, HOXB8, HOXC10, HOXC9, HOXC6, HOXC4, HOXC5, IRX4, JUN, KLF2, NFATC1, NR2F2, PITX3, POU5F1, RUNX1, WT1, c-MYC, and SOX-2.

4. A method of inhibiting the growth of a tumor comprising cancer stem cells (CSCs) in a patient diagnosed to be suffering from cancer by contacting the tumor in the patient with a compound having the structure:

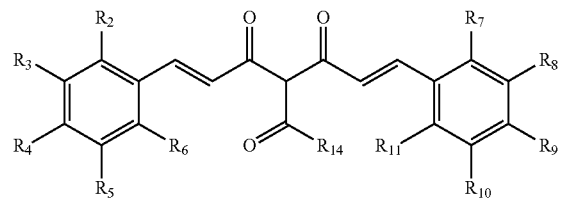

wherein $R_{14}$ is $C_{2-10}$ alkyl, $C_{2-10}$ alkenyl, $C_{2-10}$ alkynyl, heteroaryl, heterocyclyl, methoxy, —$OR_{15}$, —$NR_{16}R_{17}$, or

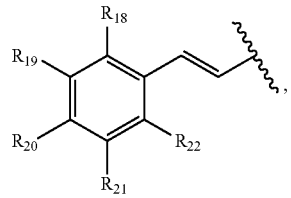

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{2-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, or $C_{2-10}$ alkynyl; and wherein each occurrence of alkyl, alkenyl, or alkynyl is branched or unbranched, unsubstituted or substituted; and or a salt thereof, so as to thereby inhibit the growth of the tumor comprising cancer stem cells (CSCs).

5. The method of claim 4, wherein the compound inhibits the growth of cancer stem cells, promotes the differentiation of cancer stem cells or inhibits cancer stem cell-relevant transcription factors.

6. The method of claim 4, further comprising contacting the tumor with a chemotherapeutic agent.

7. The method of claim 6, wherein the growth of cancer stem cells is not inhibited by, or the differentiation of cancer stem cells is not promoted by, or the cancer stem cell-relevant transcription factors are not inhibited by, the chemotherapeutic agent.

8. The method of claim 6, wherein the tumor is resistant to a chemotherapeutic agent due to the presence of cancer stem cells in the tumor.

9. The method of claim 2, wherein the chemotherapeutic agent is SBT-1214, abraxane, afinitor, erlotinib hydrochloride, gemcitabine hydrochloride, irinotecan hydrochloride, mitomycin C, sunitinib malate, taxol, taxotere, paclitaxel, cis-platin, or oxaliplatin.

10. The method of claim 6, wherein the chemotherapeutic agent is SBT-1214, abraxane, afinitor, erlotinib hydrochloride, gemcitabine hydrochloride, irinotecan hydrochloride, mitomycin C, sunitinib malate, taxol, taxotere, paclitaxel, cis-platin, or oxaliplatin.

11. A method of treating a patient diagnosed to be suffering from cancer comprising administering to the patient a compound having the structure:

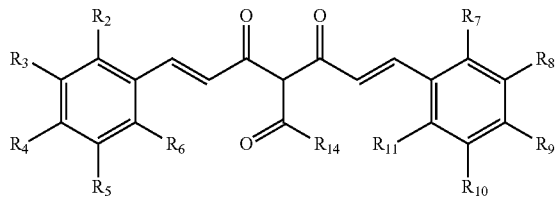

wherein $R_{14}$ is $C_{2-10}$ alkyl, $C_{2-10}$ alkenyl, $C_{2-10}$ alkynyl, heteroaryl, heterocyclyl, methoxy, —$OR_n$, —$NR_{16}R_{17}$, or

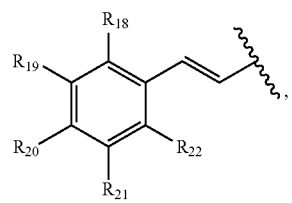

wherein $R_{15}$ is H, $C_{3-10}$ alkyl, $C_{2-10}$ alkenyl, $C_{2-10}$ alkynyl;

$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;

$R_{18}$, $R_{19}$, $R_{21}$, and $R_{22}$ are each independently H, halogen, —$NO_2$, —CN, —$NR_{23}R_{24}$, —$SR_{23}$, —$SO_2R_{23}$, —$CO_2R_{23}$, —$OR_{25}$, $CF_3$, $C_{1-10}$ alkyl, $C_{2-10}$ alkenyl, $C_{2-10}$ alkynyl, aryl, heteroaryl, or heterocyclyl;

wherein $R_{23}$, $R_{24}$, and $R_{25}$ are each, independently, H, $C_{1-10}$ alkyl, $C_{2-10}$ alkenyl, $C_{2-10}$ alkynyl, aryl, heteroaryl, or heterocyclyl;

$R_{20}$ is halogen, —$NO_2$, —CN, —$NR_{26}R_{27}$, $CF_3$, $C_{1-10}$ alkyl, $C_{2-10}$ alkenyl, $C_{2-10}$ alkynyl, aryl, heteroaryl, or heterocyclyl;

wherein $R_{26}$ and $R_{27}$ are each, independently, H, $C_{1-10}$ alkyl, $C_{2-10}$ alkenyl, $C_{2-10}$ alkynyl, aryl, heteroaryl, or heterocyclyl;

$R_2$, $R_3$, $R_4$, $R_5$, $R_6$, $R_7$, $R_8$, $R_9$, $R_{10}$, and $R_{11}$ are each independently, H, halogen, —$NO_2$, —CN, —$NR_{28}R_{29}$, —$SR_{28}$, —$SO_2R_{28}$, —$OR_{28}$, —$CO_2R_{28}$, $CF_3$, $C_{1-10}$ alkyl, $C_{2-10}$ alkenyl, $C_{2-10}$ alkynyl, aryl, heteroaryl, or heterocyclyl;

wherein $R_{28}$ and $R_{29}$ are each, H, $CF_3$, $C_{1-10}$ alkyl, $C_{2-10}$ alkenyl, or $C_{2-10}$ alkynyl; and wherein each occurrence of alkyl, alkenyl, or alkynyl is branched or unbranched, unsubstituted or substituted; and or a salt thereof, so as to thereby treat the patient diagnosed to be suffering from cancer.

12. The method of claim 11, further comprising administering to the patient a chemotherapeutic agent.

13. The method of claim 12, wherein the chemotherapeutic agent is SBT-1214, abraxane, afinitor, erlotinib hydrochloride, gemcitabine hydrochloride, irinotecan hydrochloride, mitomycin C, sunitinib malate, taxol, taxotere, paclitaxel, cis-platin, or oxaliplatin.

14. The method of claim 11, wherein at least one of $R_2$, $R_3$, $R_4$, $R_5$, and $R_6$ and at least one of $R_7$, $R_8$, $R_9$, $R_{10}$, and $R_{11}$, are each, independently, —$OR_{28}$.

15. The method of claim 11,
wherein
$R_{14}$ is methoxy, —$OR_{15}$ or —$NR_{16}R_{17}$;
$R_{15}$ is H, $C_{3-10}$ alkyl, $C_{2-10}$ alkenyl, or $C_{2-10}$ alkynyl;
$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;
or a salt thereof.

16. The method of claim 11,
wherein
$R_{14}$ is methoxy or —$NR_{16}R_{17}$;
$R_{16}$ and $R_{17}$ are each, independently, H, $C_{1-10}$ alkyl, $C_{2-10}$ alkenyl, $C_{2-10}$ alkynyl, aryl, heteroaryl, or heterocyclyl;
or a salt thereof.

17. The method of claim 11,
wherein
$R_{14}$ is —$OR_{15}$,
$R_{15}$ is H, $C_{3-10}$ alkyl, $C_{2-10}$ alkenyl, or $C_{2-10}$ alkynyl;
or a salt thereof.

18. The method of claim 11,
wherein
$R_{14}$ is —$NR_{16}R_{17}$,
wherein $R_{16}$ and $R_{17}$ are each, independently, H or aryl;
$R_2$, $R_3$, $R_4$, $R_5$, $R_6$, $R_7$, $R_8$, $R_9$, $R_{10}$, and $R_{11}$ are each independently, H, —$NR_{28}R_{29}$, or —$OR_{28}$,
wherein $R_{28}$ and $R_{29}$ are each, H or $C_{1-10}$ alkyl;
or a salt thereof.

19. The method of claim 11,
wherein
$R_{14}$ is —NH-phenyl;
$R_2$, $R_5$, $R_6$, $R_7$, $R_{10}$, and $R_{11}$ are each H;
$R_3$, $R_4$, $R_8$, and $R_9$ are each, independently, H, —OH, or —$OCH_3$;
or a salt thereof.

20. The method of claim 11, wherein the compound has the structure

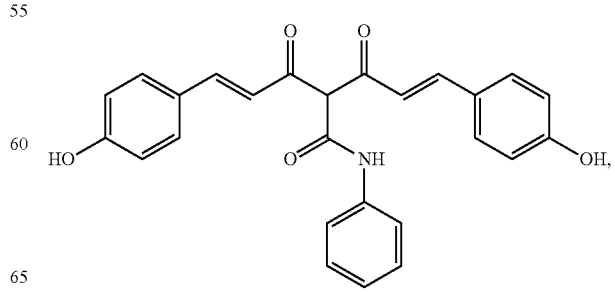

and the chemotherapeutic agent is SBT-1214, abraxane, afinitor, erlotinib hydrochloride, gemcitabine hydrochloride, irinotecan hydrochloride, mitomycin C, sunitinib malate, taxol, taxotere, paclitaxel, cis-platin, or oxaliplatin.

* * * * *